United States Patent [19]

Roberts et al.

[11] Patent Number: 5,807,698
[45] Date of Patent: *Sep. 15, 1998

[54] HUMAN CYCLIN E

[75] Inventors: James M. Roberts; Motoaki Ohtsubo; Andrew C. Koff, all of Seattle, Wash.; Frederick Cross, New York, N.Y.

[73] Assignee: Fred Hutchinson Cancer Research Center, Seattle, Wash.

[*] Notice: The term of this patent shall not extend beyond the expiration date of Pat. No. 5,449,755.

[21] Appl. No.: 488,382

[22] Filed: Jun. 7, 1995

Related U.S. Application Data

[63] Continuation of Ser. No. 947,311, Sep. 16, 1992, Pat. No. 5,449,755, which is a continuation-in-part of Ser. No. 764,309, Sep. 20, 1991, abandoned.

[51] Int. Cl.$^6$ .......................... C12N 15/00; C12N 15/63; C12N 15/85; C12Q 1/68; C07H 21/04
[52] U.S. Cl. .......................... 435/69.1; 435/6; 435/320.1; 435/326; 435/172.3; 536/23.5; 536/24.31; 536/24.33; 935/77; 935/78
[58] Field of Search .................. 536/23.5, 24.31, 536/24.33; 435/6, 69.1, 320.1, 91.2, 272.3, 326

[56] References Cited

U.S. PATENT DOCUMENTS 5,449,755  9/1995  Roberts et al. ................. 536/23.5

FOREIGN PATENT DOCUMENTS

WO 94/17414  4/1994  WIPO .

OTHER PUBLICATIONS

Arion, D., Meijer, L., Brizuela, L., and Beach, D. (1988). cdc2 is a component of the M phase–specific histone H1 kinase: evidence for identity with MPF. Cell 55, 371–378.

Cross, F. (1988). DAF1, a mutant gene affecting size control, pheromone arrest, and cell cycle kinetics of *Saccharomyces cerevisiae*. Mol. Cell. Biol. 8, 4675–4684.

Cross, F. (1990). Cell cycle arrest caused by CLN gene deficiency in *Saccharomyces cerevisiae* resembles Start–1 arrest and is independent of the mating–pheromone signalling pathway. Molec. Cell. Biol. 10, 6482–6490.

Draetta, G., and Beach, D. (1988). Activation of cdc2 protein kinase during mitosis in human cells: cell cycle–dependent phosphorylation and subunit rearrangement. Cell 54, 17–26.

Draetta, G., Luca, F., Westendorf, J., Brizuela, L. Ruderman, J., and Beach, D. (1989). cdc2 protein kinase is complexed with both cyclin A and B: evidence for proteolytic inactivation of MPF. Cell 56, 829–838.

Dunphy, W.G., Brizuela, L., Beach, D., and Newport, J. (1988). The Xenopus cdc2 protein is a component of MPF, a cytoplasmic regulator of mitosis. Cell 54, 423–431.

D'Urso, G., Marraccino, R.L., Marshak, D.R., and Roberts, J.M. (1990). Cell cycle control of DNA replication by a homologue from human cells of the p34$^{cdc2}$ protein kinase. Science 250, 786–791.

Evans, T., Rosenthal, E.T., Youngblom, J., Disten, D., and Hunt, T. (1983). Cyclin: a protein specified by maternal mRNA in sea urchin egg that is destroyed at each cleavage division. Cell 33, 389–296.

Furukawa, Y., Piwnica–Worms, H., Ernst, T.J., Kanakura, Y., and Griffin, J.D. (1990). cdc2 gene expression of the $G_1$ to S transition in human T lymphocytes. Science 250, 805–808.

Gautier, J., Norbury, C., Lohka, M., Nurse, P., and Maller, J.L. (1988) Purified maturation–promoting factor contains the product of a Xenopus homolog of the fission yeast cell cycle control gene cdc2$^+$. Cell 54, 433–439.

Gautier, J., Minshull, J., Lohka, M., Glotzer, M., Hunt, T., and Maller, J.L. (1990). Cyclin is a component of maturation–promoting factor from Xenopus. Cell 60, 487–494.

Hadwiger, J.A., Wittenberg, C., Richardson, H.E., Lopes, M. dB., and Reed, S.I. (1989). A family of cyclin homologs that control the $G_1$ phase in yeast. Proc. Natl. Acad. Sci. USA 86, 6255–6259.

Hunt, T. (1989). Maturation promoting factor, cyclin and the control of M–phase. Curr. Opin. Cell Biol. 1, 268–274.

Labbe, J.C., Lee, M.G., Nurse, P., Picard, A., and Doree, M. (1988). Activation at M–phase of a protein kinase encoded by a starfish homologue of the cell cycle gene cdc2. Nature 335, 251–254.

Labbe, J.C., Capony, J.P., Caput, D., Cavadore, J.C., Derancourt, J., Kaghad, M., Lelias, J.M., Picard, A., and Doree, M. (1989a). MPF from starfish oocytes at first meiotic metaphase is a heterodimer containing one molecule of cdc2 and one molecule of cyclin B. EMBO J. 8, 3053–3058.

Labbe, J.C., Picard, A., Peaucellier, G., Cavadore, J.C., Nurse, P., and Doree, M. (1989b). Purification of MPF from starfish: identification as the H1 histone kinase p34$^{cdc2}$ and a possible mechanism for its periodic activation. Cell 57, 253–263.

Lee, M.G., and Nurse, P. (1987). Complementation used to clone a human homologue of the fission yeast cell cycle control gene cdc2. Nature 327, 31–35.

Meijer, I., Arion, D., Golsteyn, R., Pines, J., Brizuela, L., Hunt, T., and Beach, D. (1989). Cyclin is a component of the sea urchin egg M–phase specific histone H1 kinase. EMBO J. 8, 2275–2282.

Minshull, J., Blow, J.J., and Hunt, T. (1989). Translation of cyclin mRNA is necessary for extracts of activated Xenopus eggs to enter mitosis. Cell 56, 947–956.

(List continued on next page.)

*Primary Examiner*—Lisa B. Arthur
*Attorney, Agent, or Firm*—Christensen O'Connor Johnson & Kindness PLLC

[57] ABSTRACT

Nucleic acid molecules capable of hybridizing under stringent conditions to the nucleotide sequence residing between positions 1 and 1185 of the human cyclin E cDNA sequence shown in FIG. 2. Polypeptides encoded by such nucleic acid molecules, and immunologic binding partners directed to such polypeptides.

12 Claims, 28 Drawing Sheets

OTHER PUBLICATIONS

Murray, A.W., and Kirschner, M.W. (1989). Cyclin synthesis drives the early embryonic cell cycle. Nature 339, 275–280.

Nash, R., Tokiwa, G., Anand, S., Erickson, K., and Futcher, A.B. (1988). The WH1 gene of *Saccharomyces cerivisiae* tethers cell division to cell size and is a cyclin homolog. EMBO J. 7, 4335–4346.

Nurse, P. (1990). Universal control mechanism regulating onset of M–phase. Nature 344, 503–508.

Nurse, P. and Bisset, Y. (1981). Gene required in G1 for commitment to cell cycle and in G2 for control of mitosis in fission yeast. Nature 292, 558–560.

Pardee, A.B. (1989). G1 events and regulation of cell proliferation. Science 246, 603–608.

Piggot, J.R., Rai, R., and Carter, B.L.A. (1982). A bifunctional gene product involved in two phases of the yeast cell cycle. Nature 298, 391–393.

Pines, J., and Hunter, T. (1989). Isolation of a human cyclin cDNA: evidence for cyclin mRNA and protein regulation in the cell cycle and for interaction with $p34^{cdc2}$. Cell 58, 833–846.

Rao, P.N., and Johnson, R.T. (1970). Mammalian cell fushion: studies on the regulation of DNA synthesis and mitosis. Nature 225, 159–164.

Reed, S.I., and Wittenberg, C. (1990). Mitotic role for the Cdc28 protein kinase of *Saccharomyces cerevisiae*. Proc. Natl. Acad. Sci. USA 87, 5697–5701.

Riabowol, K., Draetta, G., Brizuela, L., Vandre, D., and Beach, D. (1989). The cdc2 kinase is a nuclear protein that is essential for mitosis in mammalian cells. Cell 57, 393–401.

Richardson, H.E., Wittenberg, C., Cross, F., and Reed, S.I. (1989). An essential G1 function for cyclin–like proteins in yeast. Cell 59, 1127–1133.

Rosenthal, E.T., Hunt, T., and Ruderman, J.V. (1980). Selective translation of mRNA controls the pattern of protein synthesis during early development of the surf clam, *Spisula solidissima*. Cell 20, 487–494.

Soloman, M., Glotzer, M., Lee, T.H., Phillippe, M., and Kirschner, M.W. (1990). Cyclin activation of $p34^{cdc2}$. Cell 63, 1013–1024.

Sudbery, P.E., Goodey, A.R., and Carter, B.L. (1980). Genes which control cell proliferation in the yeast *Saccharomyces cerevisiae*. Nature (London) 288, 401–404.

Swenson, K.I., Farrell, K.M., and Ruderman, J.V. (1986). The clam embryo protein cyclin A induces entry into M phase and the resumption of meiosis in *Xenopus oocytes*. Cell 47, 861–870.

Wittenberg, C., and Reed, S.I. (1989). Conservation of function and regulation within the Cdc28/cd2 protein kinase family. Characterization of the human Cdc2HS protein kinase in *Saccharomyces cerevisiae*. Mol. Cell Biol. 4064–4068.

Wittenberg, C., Sugimoto, K., and Reed, S.I. (1990). G1–Specific cyclins of *S. cerevisiae*: cell cycle periodicity, regulation by mating pheromone, and association with the $p34^{CDC28}$ protein kinase. Cell 62, 225–237.

Zetterberg, A. (1990). Control of mammalian cell proliferation. Curr. Opin. Cell Biol. 2, 296–300.

Zetterberg, A., and Larson, O. (1985). Kinetic analysis of regulatory events in G1 leading to proliferation of quiescence of Swiss 3T3 cells. Proc. Natl. Acad. Sci. USA 82, 5365–5369.

Nasmyth, K.A. (1990). FAR–reaching discoveries about the regulation of Start. Cell 63, 1117–1120.

Roberts, J. (1991). Assembly of cyclin/CDC2 complexes during the G1 phase of the cell cycle and their role in activating DNA synthesis. Cold Spring Harbor Laboratory , p. 126.

Beach, D., Durkacz, B., and Nurse, P. (1982). Functionally homologous cell cycle control genes in fission yeast and budding yeast. Nature 300, 706–709.

Blow, J.J., and Nurse, P. (1990). A cdc2–like protein is involved in the initiation of DNA replication in Xenopus egg extracts. Cell 62, 855–862.

Booher, R., and Beach, D. (1987). Interaction between $cdc13^+$ and cdc2 in the control of mitosis in fission yeast; dissociation of $G_1$ and $G_2$ roles of the $cdc2^+$ protein kinase. EMBO J. 6, 3441–3447.

Broek, D., Bartlett, R., Crawford, K., and Nurse, P. (1990). Involvement of $p34^{cdc2}$ in establishing the dependency of S phase on mitosis. Nature 349, 388–393.

Giordano, A., Whyte, P., Harlow, E., Franza, Jr., B.R., Beach, D., and Draetta, G. (1989). A 60 kDa cdc2–associated polypeptide complexes with the E1A proteins in adenovirus–infected cells. Cell 58, 981–990.

Glotzer, M., Murray, A.W., and Kirschner, M.W. (1991). Cyclin is degraded by the ubiquitin pathway. Nature 349, 132–138.

Gould, K.L., and Nurse, P. (1989). Tyrosine phosphorylation of the fission yeast $cdc2^+$ protein kinase regulates entry into mitosis. Nature 342, 39–45.

Hartwell, L.J., Mortimer, R.K., Culotti, J., and Culotti, M. (1973). Genetic control of the cell division cycle in yeast. V. Genetic analysis of cdc mutants. Genetics 74, 267–286.

Hartwell, L.H., Culotti, J., Pringle, J.R., and Reid, B.J. (1974). Genetic control of the cell division cycle in yeast. Science 183, 46–51.

Krek, W., and Nigg, E.A. (1991). Differential phosphorylation of vetebrate $p34^{cdc2}$ kinase at the G1/S and G2/M transitions of the cell cycle: identification of major phosphorylation sites. EMBO J. 10, 305–316.

Lee, M.G., Norbury, C.J., Spurr, N.K., and Nurse, P. (1988). Regulated expression and phosphorylation of a possible mammalian cell–cycle control protein. Nature 333, 676–678.

Lew, D.J., Dulic, V., Reed, S.I. (1991). Isolation of three novel human cyclins by rescue of G1 cyclin (Cln) function in yeast. Cell 66:1197–1206.

Lorincz, A.T., and Reed, S.I. (1984). Primary structure homology between the product of the yeast cell cycle control gene CDC28 and vertebrate oncogenes. Nature 307, 183–185.

Matsushime, H., Roussel, M.F., Ashumun, R.A., and Sherr, C.J. (1991). Colony–stimulating factor 1 regulates novel cyclins during the G1 phase of the cell cycle. Cell 65, 701–713.

Motokura, T., Bloom, T., Kim, H.G., Juppner, H., Ruderman, J.V., Kronenberg, H.M., and Arnold, A. (1991). A BCL1–linked candidate oncogene which is rearranged in parathyroid tumors encodes a novel cyclin. Nature 350, 512–515.

Pardee, A.B. (1974). A restriction point of control of normal animal cell proliferation. Proc. Natl. Acad. Sci. USA 71, 1286–1290.

Paris, S., Le Guellec, R., Couturier, A., Le Guellec, K., Omilli, F., Camonis, J., MacNeill, S., and Philippe, M. (1991). Cloning by differential screening of a Xenopus cDNA coding for a protein highly homologous to cdc2. Proc. Natl. Acad. Sci. USA 88, 1029–1043.

Pines, J., and Hunter, T. (1990). Human cyclin A is adenovirus E1A–associated protein p60 and behaves differently from cyclin B. Nature 346, 760–763.

Rogers, S., Wells, R., and Rechsteiner, M. (1986). Amino acid sequences common to rapidly degraded proteins: the PEST hypothesis. Science 234, 364–368.

Simanis, V., and Nurse, P. (1986). The cell cycle control gene cdc2$^+$ of fission yeast encodes a protein kinase potentially regulated by phosphorylation. Cell 45, 261–268.

Th'ng, J.P.H., Wright, P.S., Hamaguchi, J., Lee, M.G., Norbury, C.J., Nurse, P., and Bradbury, E.M. (1990). The FT210 cell line is a mouse G2 phase mutant with a temperature–sensitive CDC2 gene product. Cell 63, 313–324.

Wang, J., Chenivesse, X., Henglein, B., and Brechot, C. (1990). Hepatitis B virus integration in a cyclin A gene is a hepatocellular carcinoma. Nature 343, 555–557.

Xiong, Y., Connolly, T., Futcher, B., and Beach, D. (1991). Human D–type cyclin. Cell 65, 691–699.

Brooks, R. (1977). Continuous protein synthesis is required to maintain the probability of entry into S phase. Cell 12:311–317.

Chang, F., and Herskowitz, I. (1990). Identification of a gene necessary for cell cycle arrest by a negative growth factor of yeast: FAR1 is an inhibitor of a G1 cyclin, CLN2. Cell 63:999–1011.

Cross, F., Roberts, J., and Weintraub, J. (1989). Simple and complex cell cycles. Ann. Rev. Cell Biol. 5:341–395.

Dirick, L., and Nasmyth, K. (1991). Positive feedback in the activation of G1 cyclins in yeast. Nature 351:754–757.

Desai, D., Gu, Y., and Morgan, D. (1992). Activation of human cyclin–dependent kinases in vitro. Molec. Biol. of the Cell, in press.

DeVoto, S., Mudryj, M., Pines, J., Hunter, T., and Nevins, J. (1992). A cyclin A–protein kinase complex possesses sequence–specific DNA binding activity: p33 CDK2 is a component of the E2F–cyclin A complex. Cell 68:167–176.

Elledge, S.J., and Spottswood, M.R. (1991). A new human p34 protein kinase, CDK2, identified by complementation of a CDC28 mutation in *S. cerevisiae*, is a homology of Xenopus Eg 1. EMBO J 10:2653–2659.

Elledge, S., Richman, R., Hall, F., Williams, F., Lodgson, N., and Harper, W. (1992). CDK2 encodes a 33–kDaa cyclin A–associated protein kinase and is expressed before CDC2 in the cell cycle. Proc. Natl. Acad. Sci. USA, in press.

Fang, F., and Newport, J. (1991). Evidence that the G1–S and G2–M transitions are controlled by different CDC2 proteins in higher eukaryotes. Cell 66:731–742.

Giordano, A., Lee, J., Scheppler, J., Hermann, C., Harlow, E., Deuschle, U., Beach, D., and Franza, R. (1991). Cell cycle regulation of histone H1 kinase activity associated with the adenoviral protein E1A. Science 253:1271–1275.

Hartwell, L. (1991). Twenty–five years of cell cycle genetics. Genetics 129:975–980.

Hunter, T., and Pines, J. (1991). Cyclins and Cancer. Cell 66:1071–1074.

Lamb, N., Fernandez, A., Watrin, A., Labbe, J., and Cavadore, J. (1990). Microinjection of the p34 CDC2 kinase induces marked changes in cell shape, cytoskeletal organization and chromatin structure in mammalian fibroblasts. Cell 60:151–165.

Marraccino, R., Firpo, E., and Roberts, J. (1992). Activation of the p34 CDC2 protein kinase at the start of S phase in the human cell cycle. Molec. Biol. of the Cell 3: 389–401.

Pardee, A., Medrano, E., and Rossow, P. (1981). A labile protein model for growth control of mammalian cells. In: *The biology of normal human growth,* Ritzen et al., eds. Raven Press.

Rosenblatt, J., Gu, Y., and Morgan, D. (1992). Human cyclin dependent kinase 2 (CDK2) is activated during the S and G2 phases of the cell cycle and associates with cyclin A. Proc. Nat. Acad. Sci. USA, in press.

Rossow, P., Riddle, B., and Pardee, A. (1979). Synthesis of labile, serum–dependent protein in early G1 controls animal cell growth. Proc. Nat. Acad. Sci. USA, 76:4446–4450.

Schneiderman, M., Dewey, W., and Highfield, D. (1971). Inhibition of DNA synthesis in synchronized Chinese hamster cells treated in G1 with cycloheximide. Exp. Cell Re. 67:147–155.

Shirodkar, S., Ewen, M., DeCaprio, J., Morgan, J., Livingston, D., and Chittenden, T. (1992). The transcription factor E2F interacts with the retinoblastoma product and a p107–cyclin A complex in a cell cycle regulated manner. Cell 68:157–166.

Solomon, M., Lee, T., and Kirschner, M. (1992). Role of phosphorylation in p34 CDC2 activation: identification of an activating kinase. Molec. Biol. of the Cell 3:13–27.

Tsai, L., Harlow, E., and Meyerson, M. (1991). Isolation of the human CDK2 gene that encodes the cyclin–A and adenovirus E1A–associated p33 kinase. Nature 353:174–177.

Wynford–Thomas, D., LaMontagne, A., Marin, G., and Prescott, D. (1985). Location of the isoleucine arrest point in CHO and 3T3 cells. Exp. Cell. Res. 158, 525–532.

Koff, A., et al., Cell 66:1212–1228, Sep. 20, 1991.

Nugent et al., J. Cell Science 99:669–674, 1991.

Nasmyth, K., and Dirick, L. (1991). The role of SW14 and SW15 in the activity of G1 cyclins in yeast. Cell 66:995–1013.

Lahue, E.E., Smith, A.V. and Orr–Weaver, T.L. (1991). A novel cyclin gene from Drosophila complements CLN function in yeast. Genes & Development 5:2153–2362.

Rempel et al., J. Biol. Chem. (Mar. 24, 1995) 270(12): 6843–6855.

Damjanov, I. et al., Biochem. Biophys. Res. Comm. (Jun. 1994) 201(2): 994–1000.

Sewing, A. et al., J. Cell Sci. (1994) 107: 581–588.

Ohtsubo, M. et al. Mol. Cell. Biol. (May 1995) 15(5): 2612–2624.

Geng, Y. et al. Oncogene (1996) 12: 1173–1180.

Sgambato, A. et al. Can. Res (1996) 56: 1389–1399.

Bortner, D. et al. Mol. Cell. Biol. (1997) 17(1): 453–459.

McCarthy, T. et al. Nature (1990) 343: 562–564.

Fig. 2A

```
         GTGCTCACCCGGCCGGAGTCGGCTCGCTCCAGGAAGAGGGCAAACGTGGACACC

0   ATG AAG GAG GAC GGC
      MET LYS GLU ASP GLY

61   ACC GTT TTT CAG TTG CAG GAT CCA GAT GAA ATG GCC AAA ATC GCC AGG ACG AAG AAC GAC
      THR VAL PHE GLN LEU GLN ASP PRO ASP GLU MET ALA LYS ILE ALA ARG THR ARG ASN ASP

121   CAG TGT GGG AGC CAG CCT TGG GAC AAT GAC AAT GCA GTC GCA CCC GAC TGC TCC CTG ATC
      GLN CYS GLY SER GLN PRO TRP ASP ASN ASP ASN ALA VAL ALA PRO ASP CYS SER LEU ILE

181   CCC ACA CCT GAC AAA GAT GAT GAT GAT CGG GTT TAC CCA AAC TCA ACG TGC CCT AAG CCT CGG
      PRO THR PRO ASP LYS ASP ASP ASP ASP ARG VAL TYR PRO ASN SER THR CYS PRO LYS PRO ARG

241   ATT GCA CCA GCA TCC AGA GGC CTG CCT CTA GTA CCA TCA AAC AGC GCA GAG GAG
      ILE ALA PRO ALA PRO ARG GLY LEU PRO LEU VAL PRO SER ASN SER ALA GLU GLU GLU GLU

301   GTC TGG AAA ATC ATG TTA AAC AAC TAC TYR ATT CGA GCA ACC TTT CAC GAT TGG CTT CGG
      VAL TRP LYS ILE MET LEU ASN ASN TYR TYR ILE ARG ALA THR PHE HIS ASP TRP LEU PHE GLU

361   CAA CAC CCT CTT CTG CAG CCA ATG CGA GCA ACC TTT CTT ATT TGG CTT ATG GAG GTG
      GLN HIS PRO LEU LEU GLN PRO MET ARG ALA THR PHE LEU ILE TRP LEU MET GLU VAL

421   TGT GAA GTC TAT GTC GAG AGG CAC TTG GCA CAA CTT TTT GAC TTC GAC CGG
      CYS GLU VAL TYR VAL GLU ARG HIS LEU ALA GLN LEU PHE ASP PHE ASP ARG

481   TAT ATG GCG ACA CAA AAT GTT GAA AAT CTT CTT ATT GGG ATT TCA TCT
      TYR MET ALA THR GLN ASN VAL GLU ASN LEU LEU ILE GLY ILE SER SER

541   TTA TTT ATT GCA GCC AAA CTT GAG GAA ATC TAT CCT CCA AAG TTG CAC CAG TTT GCG TAT
      LEU PHE ILE ALA ALA LYS LEU GLU GLU ILE TYR PRO PRO LYS LEU HIS GLN PHE ALA TYR
```

Fig. 2B.

```
601  GTG ACA GAT GGA GCT TGT TCA GGA GAT GAA ATT CTC ACC ATG GAA TTA ATG ATT ATG AAG
     Val Thr Asp Gly Ala Cys Ser Gly Asp Glu Ile Leu Thr Met Glu Leu Met Ile Met Lys

661  GCC CTT AAG TGG CGT TTA AGT CCC CTG ACT ATT GTG TCC TGG AAT GTA TAC ATG CAG
     Ala Leu Lys Trp Arg Leu Ser Pro Leu Thr Ile Val Ser Trp Asn Val Tyr Met Gln

721  GTT GCA TAT CTA AAT GAC TTA CAT GAA GTG CTA CTG CCG CAG TAT CCC CAA ATC TTT
     Val Ala Tyr Leu Asn Asp Leu His Glu Val Leu Leu Pro Gln Tyr Pro Gln Ile Phe

781  ATA CAG ATT GCA GAG CTG TTG GAT CTC TGT GTT CTT GAA TTT CCT
     Ile Gln Ile Ala Glu Leu Leu Asp Leu Cys Val Leu Glu Phe Pro

841  TAT GGT ATA CTT GCT GCT TCG GCC TAT CAT TTC TCA GTT ATG CAA AAG
     Tyr Gly Ile Leu Ala Ala Ser Ala Tyr His Phe Ser Val Met Gln Lys

901  GTT TCA GGG TAT CAG TGG TGC GAC ATA GAG AAC TGT GTC AAG TTT GCC
     Val Ser Gly Tyr Gln Trp Cys Asp Ile Glu Asn Cys Val Lys Phe Ala

961  ATG GTT ATA AGG GAG ACG GGG AGC ATA CAA AGA GAC CAC TTC GAT GAT GAA
     Met Val Ile Arg Glu Thr Gly Ser Ile Gln Arg Asp His Phe Asp Asp Glu

1021 GAT GCA CAC AAC ATA CAG ACC CAC AGA GAC AAA GCC CGA GTC GCT GAT GCA
     Asp Ala His Asn Ile Gln Thr His Arg Asp Lys Ala Arg Val Ala Asp Ala

1081 AAG AAA GCC ATG TTG TCT GAA CAA AAT AGG GCT TCT CCT AGT GGG CTC CTC ACC
     Lys Lys Ala Met Leu Ser Glu Gln Asn Arg Ala Ser Pro Ser Gly Leu Leu Thr

1141 CCG CCA CAG AGC AGC GGT AAG AAG CAG AGC AGC GGG CCG GAA ATG GCG TGA CCACCCATCCTTCT
     Pro Pro Gln Ser Ser Gly Lys Lys Gln Ser Ser Gly Pro Glu Met Ala
```

```
CCACCAAAGACAGTTGCGCGCCTGCTCCACGTTCTCTTCTGTCTGTTGCAGCGGAGGCGTGCGTTTGCTTTTACAGATA
TCTGAATGGAAGAGTGTTTCTTCCACAACAGAAGTATTTCTGTGGATGGCATCAAACAGGGCAAAGTGTTTTTATTGA
ATGCTTATAGGTTTTTTTAAATAAGTGGGTCAAGTACACCAGCCACCTCCAGACACCAGTGCGTGCTCCCGATGCTGC
TATGGAAGGTGCTACTTGACCTAAAGGACTCCCACAACAACAAAAGCTTGAAGCTGTGGAGGCCACGGTGGCGTGGCT
CTCCTCGCAGGTGTTCTCGGCTCCGTTGTACCAAGTGGAGCAGGTGGTTGCGGGCAAGCGTTGTGCAGAGCCCATAGCC
AGCTGGGCAGGGGGCTGCCCCTCTCC
```

Fig. 2c.

```
CYCLIN E
CYCLIN A    MLGNSAPGPA  TREAGSALLA  LQQTALQEDQ  ENINPEKAAP
CYCLIN B            MALRV  TRNSKINAEN  KAKINMAGAK  RVPTAPAATS

MKED
CYCLIN E    VQQPRTRAAL  AVLKSGNPRG  LAQQQ RPKT   RRVAPLKDLP   VNDE
CYCLIN A                             E
CYCLIN B    KPGLRPRTAL  GDIGNKVSEQ  LQAKMPMKKE   AKPSATGKV    IDK

CYCLIN E    GGAEFSARSR  KRKA NVTVF  LQDPDEEMAK   ID RTAR DQ
CYCLIN A    HVTVPPWKAN  SKQP AFTIH  VDEAEKEAQK   KPAESQKIER
CYCLIN B    KLPKPLEKVP  MLVPVPVSEP  VPEPEPEPEP   EPVKEEKLSP

CYCLIN E    CGSQPWDNNA  VCADPCSLIP  TPDKEDDDRV   YPNSTCKPRI   IAPS
CYCLIN A    EDALAFNSAI  SLPGPRKPLV  PLDYPMDGSF   ESPHTMDMSI   VLED
CYCLIN B    EPILVDTASP  SPMETSGCAP  AEEQLC QAF   SDVILAVNDV   DAED

CYCLIN E    RGSPLPVLSW  ANREEV  WK  IMLNKEKTYL   RDQHFLEQHP
CYCLIN A    EKPVSVNENP  DYHEDIHTYL  R  EMEVKCK   PKVGYMKKQP
CYCLIN B    GADPNLCS    EYBKDIYAYL  RQLEEEQAVR   PK   YL LBR

MRAIL   DWL V            L  ET        DR
CYCLIN E    LLQPKMRAIL  LDWLMEVCEV  YKLHRETFYL   AQDFEFDRYM
CYCLIN A    DITNSMRAIL  VDWLVEVGEE  YKLQNETLHL   AVNYIDREFL
CYCLIN B    EVTGNMRAIL  IDWLVQVQMK  FRLLQETMYM   TVSIIDREM
```

```
            V            LQL G        A K EE YP P    E    T
CYCLIN E  ATQENVVKTL  LQLIGISSLF  IAAKLEEIYP  PKLHQFAYVT
CYCLIN A  SSM SVLRGK  LQLVGTAAML  LASKFEEIYP  PEVAEFVYIT
CYCLIN B  QNN CVFKKM  LQLVGVTAMF  IASKYEEFYP  PEIGDFAFVT

D            ME    L        L         L
CYCLIN E  DGACSGDEIL  TMELMIMKAL  KWRLSPLTIV  SWLNVYMQ
CYCLIN A  DDTYTKKQVL  RMEHLVLKVL  TFDLAAPTVN  QFLTQYFL
CYCLIN B  DNTYTKHQIR  QMEMKILRAL  NFGLGRPLPL  HFLRRASK

L
CYCLIN E  VAYLNDLHEV  LLPQYPQQIF  IQIAELLDLC  VLDVDCLEFP
CYCLIN A  HQQPANCKVE  SLAMFLGELS  LIDADPY LK  YLPSVIAGAA
CYCLIN B  IGEV KVEQH  TLAKYLMELT  MLDYDM  VH  FPPSQIAAGA

LA                        Y
CYCLIN E  YGILAASALY  HFSSSELMQK  VSGYQWCDIE  NCVKWMVPFA
CYCLIN A  F HLALYTVT  GQSWPESLIR  KTGYTLESLK  PCLMDLHQTY
CYCLIN B  F CLALKILD  NGEWTPTLQH  YLSYTEESLL  PVMQHLAKNV

CYCLIN E  MVIRETGSSK  LK HFRGVAD  EDAHNIQTHR  DSLDLLDKA
CYCLIN A  LKAPQHAQQS  IREDYKNSKY  HGVSLLNPP   ETLNL
CYCLIN B  VMVNQGLTKH  MTVKNKYATS  KHAKISTLPQ  LNSALVQDLA

CYCLIN E  RAKKAMLSEQ  NRASPLPSGL  LTPPQSGKKQ  SSGPEMA
CYCLIN B  KAVAKV
```

| Plasmid | CDC28 | cdc28-13 |
|---|---|---|
| pADNS | $<10^{-4}$ | $<10^{-4}$ |
| pADANS | $<10^{-4}$ | $<10^{-4}$ |
| pADNS-CYC E | 0.26 | 0.0034 |
| pADANS-CYC E | 1.0 | 0.035 |
| pADANS-CYC B | 0.23 | 0.3 |

Fig. 4.

| Plasmid | 30 | 38 |
|---|---|---|
| pMAC-CYC E | $<2\times10^{-4}$ | $<2\times10^{-4}$ |
| pADNS-CDC2-HS | $<2\times10^{-4}$ | $<2\times10^{-4}$ |
| pADNS-CDK2-HS | $<2\times10^{-4}$ | $<2\times10^{-4}$ |
| pMAC-CYC E + pADNS-CDC2-HS | 0.56 | 0.24 |
| pMAC-CYC E + pADNS-CDK2-HS | 0.10 | $<2\times10^{-4}$ |

Fig. 5.

|  | G1/S | | | | G2/M | | |
| --- | --- | --- | --- | --- | --- | --- | --- |
|  | galactose | glucose | galactose | glucose | galactose | glucose | |
|  | CLN/cdc28-13 | CYCE/cdc28-13 | | CLN/cdc28-13 | CLB/cdc28-13 | CLB/cdc28-13 | |
| 30°C | + | − | | + | + | + | |
| 38°C | − | − | | − | − | − | | fig. 6.

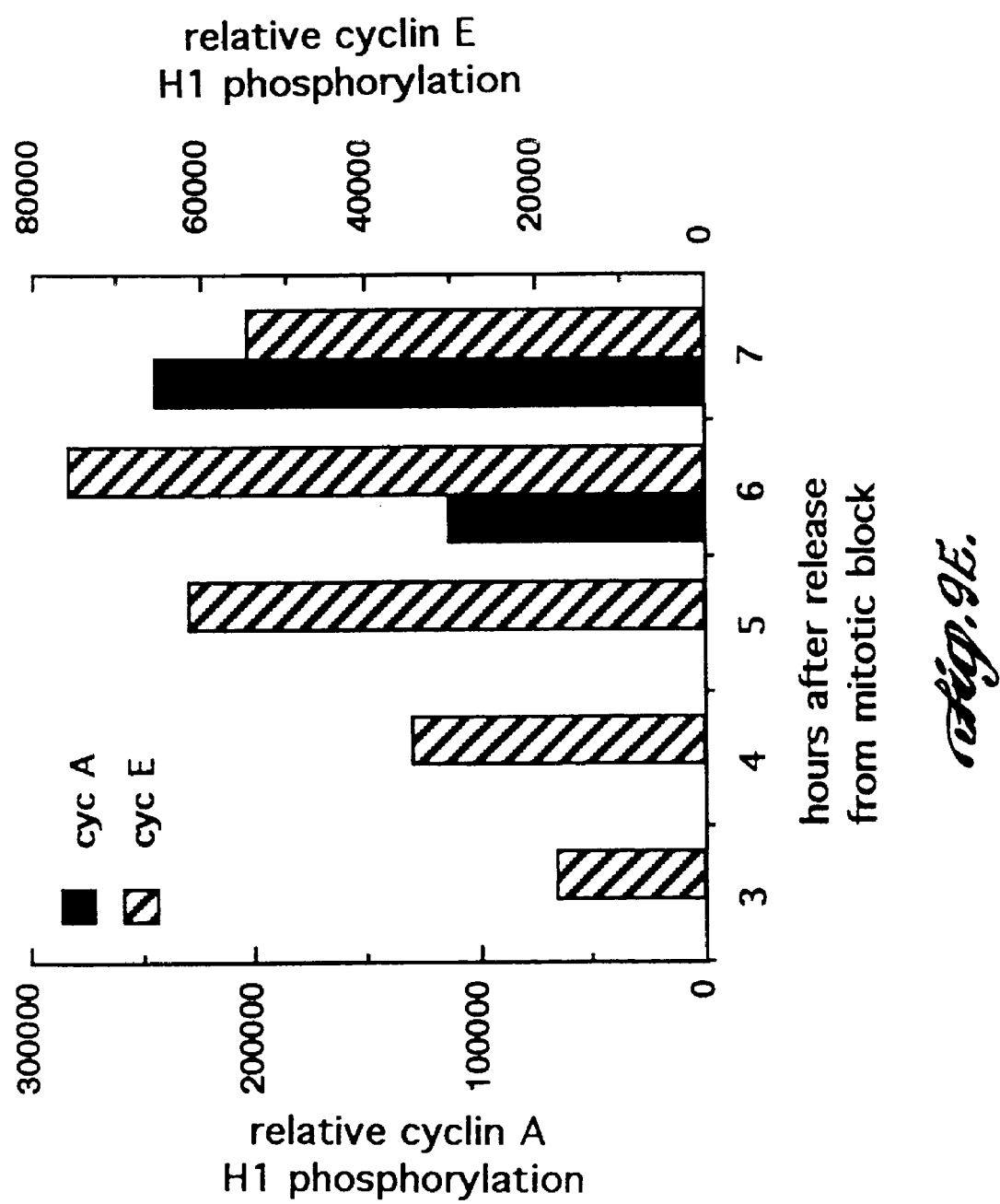

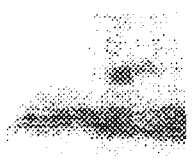 
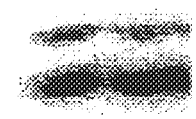
Fig. 11A.    Fig. 11B.

cdk2 cycE

SEQUENCE LISTING ( 1 ) GENERAL INFORMATION:

( i i i ) NUMBER OF SEQUENCES:8

( 2 ) INFORMATION FOR SEQ ID NO:1:

( i ) SEQUENCE CHARACTERISTICS:
( A ) LENGTH:1680 base pairs
( B ) TYPE:nucleic acid
( C ) STRANDEDNESS:single
( D ) TOPOLOGY:linear ( i i ) MOLECULE TYPE:cDNA
( A ) DESCRIPTION:Cyclin E cDNA sequence; Figure 2

( i x ) SEQUENCE DESCRIPTION: SEQ ID NO:1:

```
GTGCTCACCC  GGCCCGGTGC  CACCCGGGTC  CACAGGGATG  CGAAGGAGCG  GGACACCATG    60
AAGGAGGACG  GCGGCGCGGA  GTTCTCGGCT  CGCTCCAGGA  AGAGGAAGGC  AAACGTGACC   120
GTTTTTTTGC  AGGATCCAGA  TGAAGAAATG  GCCAAAATCG  ACAGGACGGC  GAGGGACCAG   180
TGTGGGAGCC  AGCCTTGGGA  CAATAATGCA  GTCTGTGCAG  ACCCCTGCTC  CCTGATCCCC   240
ACACCTGACA  AAGAAGATGA  TGACCGGGTT  TACCCAAACT  CAACGTGCAA  GCCTCGGATT   300
ATTGCACCAT  CCAGAGGCTC  CCCGCTGCCT  GTACTGAGCT  GGGCAAATAG  AGAGGAAGTC   360
TGGAAAATCA  TGTTAAACAA  GGAAAAGACA  TACTTAAGGG  ATCAGCACTT  TCTTGAGCAA   420
CACCCTCTTC  TGCAGCCAAA  AATGCGAGCA  ATTCTTCTGG  ATTGGTTAAT  GGAGGTGTGT   480
GAAGTCTATA  AACTTCACAG  GGAGACCTTT  TACTTGGCAC  AAGATTTCTT  TGACCGGTAT   540
ATGGCGACAC  AAGAAAATGT  TGTAAAAACT  CTTTTACAGC  TTATTGGGAT  TTCATCTTTA   600
TTTATTGCAG  CCAAACTTGA  GGAAATCTAT  CCTCCAAAGT  TGCACCAGTT  TGCGTATGTG   660
ACAGATGGAG  CTTGTTCAGG  AGATGAAATT  CTCACCATGG  AATTAATGAT  TATGAAGGCC   720
CTTAAGTGGC  GTTTAAGTCC  CCTGACTATT  GTGTCCTGGC  TGAATGTATA  CATGCAGGTT   780
GCATATCTAA  ATGACTTACA  TGAAGTGCTA  CTGCCGCAGT  ATCCCCAGCA  AATCTTTATA   840
CAGATTGCAG  AGCTGTTGGA  TCTCTGTGTC  CTGGATGTTG  ACTGCCTTGA  ATTTCCTTAT   900
GGTATACTTG  CTGCTTCGGC  CTTGTATCAT  TTCTCGTCAT  CTGAATTGAT  GCAAAAGGTT   960
TCAGGGTATC  AGTGGTGCGA  CATAGAGAAC  TGTGTCAAGT  GGATGGTTCC  ATTTGCCATG  1020
GTTATAAGGG  AGACGGGGAG  CTCAAAACTG  AAGCACTTCA  GGGGCGTCGC  TGATGAAGAT  1080
GCACACAACA  TACAGACCCA  CAGAGACAGC  TTGGATTTGC  TGGACAAAGC  CCGAGCAAAG  1140
AAAGCCATGT  TGTCTGAACA  AAATAGGGCT  TCTCCTCTCC  CCAGTGGGCT  CCTCACCCCG  1200
CCACAGAGCG  GTAAGAAGCA  GAGCAGCGGG  CCGGAAATGG  CGTGACCACC  CCATCCTTCT  1260
CCACCAAAGA  CAGTTGCGCG  CCTGCTCCAC  GTTCTCTTCT  GTCTGTTGCA  GCGGAGGCGT  1320
```

```
GCGTTTGCTT  TTACAGATAT  CTGAATGGAA  GAGTGTTTCT  TCCACAACAG  AAGTATTTCT      1380

GTGGATGGCA  TCAAACAGGG  CAAAGTGTTT  TTTATTGAAT  GCTTATAGGT  TTTTTTTAAA      1440

TAAGTGGGTC  AAGTACACCA  GCCACCTCCA  GACACCAGTG  CGTGCTCCCG  ATGCTGCTAT      1500

GGAAGGTGCT  ACTTGACCTA  AAGGACTCCC  ACAACAACAA  AAGCTTGAAG  CTGTGGAGGG      1560

CCACGGTGGC  GTGGCTCTCC  TCGCAGGTGT  TCTGGGCTCC  GTTGTACCAA  GTGGAGCAGG      1620

TGGTTGCGGG  CAAGCGTTGT  GCAGAGCCCA  TAGCCAGCTG  GGCAGGGGGC  TGCCCTCTCC      1680
```

( 2 ) INFORMATION FOR SEQ ID NO:2:

( i ) SEQUENCE CHARACTERISTICS:
        ( A ) LENGTH:395 amino acids
        ( B ) TYPE:amino acid
        ( D ) TOPOLOGY:linear ( i i ) MOLECULE TYPE:polypeptide
        ( A ) DESCRIPTION:Cyclin E amino acid sequence; Figure 2

( v i ) ORIGINAL SOURCE:
        ( A ) ORGANISM:

( v i i ) IMMEDIATE SOURCE:

( i x ) SEQUENCE DESCRIPTION: SEQ ID NO:2:

```
Met  Lys  Glu  Asp  Gly  Gly  Ala  Glu  Phe  Ser  Ala  Arg  Ser  Arg  Lys
 1              5                        10                       15

Arg  Lys  Ala  Asn  Val  Thr  Val  Phe  Leu  Gln  Asp  Pro  Asp  Glu  Glu
                 20                       25                       30

Met  Ala  Lys  Ile  Asp  Arg  Thr  Ala  Arg  Asp  Gln  Cys  Gly  Ser  Gln
                     35                       40                       45

Pro  Trp  Asp  Asn  Asn  Ala  Val  Cys  Ala  Asp  Pro  Cys  Ser  Leu  Ile
                         50                       55                       60

Pro  Thr  Pro  Asp  Lys  Glu  Asp  Asp  Asp  Arg  Val  Tyr  Pro  Asn  Ser
                         65                       70                       75

Thr  Cys  Lys  Pro  Arg  Ile  Ile  Ala  Pro  Ser  Arg  Gly  Ser  Pro  Leu
                         80                       85                       90

Pro  Val  Leu  Ser  Trp  Ala  Asn  Arg  Glu  Glu  Val  Trp  Lys  Ile  Met
                         95                      100                      105

Leu  Asn  Lys  Glu  Lys  Thr  Tyr  Leu  Arg  Asp  Gln  His  Phe  Leu  Glu
                        110                      115                      120

Gln  His  Pro  Leu  Leu  Gln  Pro  Lys  Met  Arg  Ala  Ile  Leu  Leu  Asp
                        125                      130                      135

Trp  Leu  Met  Glu  Val  Cys  Glu  Val  Tyr  Lys  Leu  His  Arg  Glu  Thr
                        140                      145                      150

Phe  Tyr  Leu  Ala  Gln  Asp  Phe  Phe  Asp  Arg  Tyr  Met  Ala  Thr  Gln
                        155                      160                      165

Glu  Asn  Val  Val  Lys  Thr  Leu  Leu  Gln  Leu  Ile  Gly  Ile  Ser  Ser
                        170                      175                      180

Leu  Phe  Ile  Ala  Ala  Lys  Leu  Glu  Glu  Ile  Tyr  Pro  Pro  Lys  Leu
                        185                      190                      195

His  Gln  Phe  Ala  Tyr  Val  Thr  Asp  Gly  Ala  Cys  Ser  Gly  Asp  Glu
                        200                      205                      210

Ile  Leu  Thr  Met  Glu  Leu  Met  Ile  Met  Lys  Ala  Leu  Lys  Trp  Arg
                        215                      220                      225

Leu  Ser  Pro  Leu  Thr  Ile  Val  Ser  Trp  Leu  Asn  Val  Tyr  Met  Gln
                        230                      235                      240

Val  Ala  Tyr  Leu  Asn  Asp  Leu  His  Glu  Val  Leu  Leu  Pro  Gln  Tyr
                        245                      250                      255
```

| Pro | Gln | Gln | Ile | Phe<br>260 | Ile | Gln | Ile | Ala | Glu<br>265 | Leu | Leu | Asp | Leu | Cys<br>270 |
|---|---|---|---|---|---|---|---|---|---|---|---|---|---|---|
| Val | Leu | Asp | Val | Asp<br>275 | Cys | Leu | Glu | Phe | Pro<br>280 | Tyr | Gly | Ile | Leu | Ala<br>285 |
| Ala | Ser | Ala | Leu | Tyr<br>290 | His | Phe | Ser | Ser | Ser<br>295 | Glu | Leu | Met | Gln | Lys<br>300 |
| Val | Ser | Gly | Tyr | Gln<br>305 | Trp | Cys | Asp | Ile | Glu<br>310 | Asn | Cys | Val | Lys | Trp<br>315 |
| Met | Val | Pro | Phe | Ala<br>320 | Met | Val | Ile | Arg | Glu<br>325 | Thr | Gly | Ser | Ser | Lys<br>330 |
| Leu | Lys | His | Phe | Arg<br>335 | Gly | Val | Ala | Asp | Glu<br>340 | Asp | Ala | His | Asn | Ile<br>345 |
| Gln | Thr | His | Arg | Asp<br>350 | Ser | Leu | Asp | Leu | Leu<br>355 | Asp | Lys | Ala | Arg | Ala<br>360 |
| Lys | Lys | Ala | Met | Leu<br>365 | Ser | Glu | Gln | Asn | Arg<br>370 | Ala | Ser | Pro | Leu | Pro<br>375 |
| Ser | Gly | Leu | Leu | Thr<br>380 | Pro | Pro | Gln | Ser | Gly<br>385 | Lys | Lys | Gln | Ser | Ser<br>390 |
| Gly | Pro | Glu | Met | Ala<br>395 | | | | | | | | | | |

(2) INFORMATION FOR SEQ ID NO:3:

(i) SEQUENCE CHARACTERISTICS:
        (A) LENGTH:9 amino acids
        (B) TYPE:amino acid
        (D) TOPOLOGY:linear (ii) MOLECULE TYPE:peptide
        (A) DESCRIPTION:Peptide corresponding to C terminus of human
            CDC2

(vi) ORIGINAL SOURCE:
        (A) ORGANISM:Homo sapiens (ix) SEQUENCE DESCRIPTION: SEQ ID NO:3:

| Tyr | Leu | Asp | Asn | Gln | Ile | Lys | Lys | Met |
|---|---|---|---|---|---|---|---|---|
| 1 | | | | 5 | | | | 9 |

(2) INFORMATION FOR SEQ ID NO:4:

(i) SEQUENCE CHARACTERISTICS:
        (A) LENGTH:17 amino acids
        (B) TYPE:amino acid
        (D) TOPOLOGY:linear (ii) MOLECULE TYPE:peptide
        (A) DESCRIPTION:Peptide from conserved "PSTAIRE"domain of
            CDC2 gene family (vi) ORIGINAL SOURCE:
        (A) ORGANISM:Homo Sapiens (ix) SEQUENCE DESCRIPTION: SEQ ID NO:4:

| Cys | Glu | Gly | Val | Pro | Ser | Thr | Ala | Ile | Arg | Glu | Ile | Ser | Leu | Leu |
|---|---|---|---|---|---|---|---|---|---|---|---|---|---|---|
| 1 | | | | 5 | | | | | 10 | | | | | 15 |
| Lys | Glu | | | | | | | | | | | | | |
| | 17 | | | | | | | | | | | | | |

(2) INFORMATION FOR SEQ ID NO:5:

(i) SEQUENCE CHARACTERISTICS:
        (A) LENGTH:21 amino acids
        (B) TYPE:amino acid -continued (D) TOPOLOGY:linear (ii) MOLECULE TYPE:peptide
    (A) DESCRIPTION:Peptide corresponding to residues 104-123
        of Human cyclin A (vi) ORIGINAL SOURCE:
    (A) ORGANISM:

(ix) SEQUENCE DESCRIPTION: SEQ ID NO:5:

```
Tyr Asp Glu Ala Glu Lys Glu Ala Gln Lys Lys Pro Ala Glu Ser
1               5                   10                  15
Gln Lys Ile Glu Arg Glu
                20
```

(2) INFORMATION FOR SEQ ID NO:6:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: protein
        (A) DESCRIPTION:Sequences conserved among cyclins E, A, and
          B; Figure 3

(vi) ORIGINAL SOURCE:
        (A) ORGANISM:Homo Sapiens (ix) SEQUENCE DESCRIPTION: SEQ ID NO:6:

```
Met Arg Ala Ile Leu
1               5
```

(2) INFORMATION FOR SEQ ID NO:7:

(i) SEQUENCE CHARACTERISTICS:
        (A) LENGTH: 433 amino acids
        (B) TYPE: amino acid
        (C) STRANDEDNESS: single
        (D) TOPOLOGY: linear (ii) MOLECULE TYPE: protein
        (A) DESCRIPTION:Cyclin A polypeptide sequence; Figure 3

(vi) ORIGINAL SOURCE:
        (A) ORGANISM:Homo Sapiens (xi) SEQUENCE DESCRIPTION: SEQ ID NO:7:

```
Met Ala Leu Arg Val Thr Arg Asn Ser Lys Ile Asn Ala Glu Asn Lys
1               5                   10                  15
Ala Lys Ile Asn Met Ala Gly Ala Lys Arg Val Pro Thr Ala Pro Ala
                20                  25                  30
Ala Thr Ser Lys Pro Gly Leu Arg Pro Arg Thr Ala Leu Gly Asp Ile
                35              40                  45
Gly Asn Lys Val Ser Glu Gln Leu Gln Ala Lys Met Pro Met Lys Lys
        50                  55                  60
Glu Ala Lys Pro Ser Ala Thr Gly Lys Val Ile Asp Lys Lys Leu Pro
65                  70                  75                  80
Lys Pro Leu Glu Lys Val Pro Met Leu Val Pro Val Pro Val Ser Glu
                85                  90                  95
Pro Val Pro Glu Pro Glu Pro Glu Pro Glu Pro Glu Pro Val Lys Glu
                100                 105                 110
Glu Lys Leu Ser Pro Glu Pro Ile Leu Val Asp Thr Ala Ser Pro Ser
                115                 120                 125
Pro Met Glu Thr Ser Gly Cys Ala Pro Ala Glu Glu Gln Leu Cys Gln
```

130                           135                              140
Ala  Phe  Ser  Asp  Val  Ile  Leu  Ala  Val  Asn  Asp  Val  Asp  Ala  Glu  Asp
145                      150                      155                          160

Gly  Ala  Asp  Pro  Asn  Leu  Cys  Ser  Glu  Tyr  Asx  Lys  Asp  Ile  Tyr  Ala
                    165                      170                     175

Tyr  Leu  Arg  Gln  Leu  Glu  Glu  Glu  Gln  Ala  Val  Arg  Pro  Lys  Tyr  Leu
               180                      185                      190

Leu  Asx  Arg  Glu  Val  Thr  Gly  Asn  Met  Arg  Ala  Ile  Leu  Ile  Asp  Trp
          195                      200                     205

Leu  Val  Gln  Val  Gln  Met  Lys  Phe  Arg  Leu  Leu  Gln  Glu  Thr  Met  Tyr
     210                      215                     220

Met  Thr  Val  Ser  Ile  Ile  Asp  Arg  Phe  Met  Gln  Asn  Asn  Cys  Val  Phe
225                      230                     235                          240

Lys  Lys  Met  Leu  Gln  Leu  Val  Gly  Val  Thr  Ala  Met  Phe  Ile  Ala  Ser
                    245                     250                     255

Lys  Tyr  Glu  Glu  Phe  Tyr  Pro  Pro  Glu  Ile  Gly  Asp  Phe  Ala  Phe  Val
               260                      265                     270

Thr  Asp  Asn  Thr  Tyr  Thr  Lys  His  Gln  Ile  Arg  Gln  Met  Glu  Met  Lys
          275                      280                     285

Ile  Leu  Arg  Ala  Leu  Asn  Phe  Gly  Leu  Gly  Arg  Pro  Leu  Pro  Leu  His
     290                      295                     300

Phe  Leu  Arg  Arg  Ala  Ser  Lys  Ile  Gly  Glu  Val  Lys  Val  Glu  Gln  His
305                      310                     315                          320

Thr  Leu  Ala  Lys  Tyr  Leu  Met  Glu  Leu  Thr  Met  Leu  Asp  Tyr  Asp  Met
                    325                     330                     335

Val  His  Phe  Pro  Pro  Ser  Gln  Ile  Ala  Ala  Gly  Ala  Phe  Cys  Leu  Ala
               340                      345                     350

Leu  Lys  Ile  Leu  Asp  Asn  Gly  Glu  Trp  Thr  Pro  Thr  Leu  Gln  His  Tyr
          355                      360                     365

Leu  Ser  Tyr  Thr  Glu  Glu  Ser  Leu  Leu  Pro  Val  Met  Gln  His  Leu  Ala
     370                      375                     380

Lys  Asn  Val  Val  Met  Val  Asn  Gln  Gly  Leu  Thr  Lys  His  Met  Thr  Val
385                      390                     395                          400

Lys  Asn  Lys  Tyr  Ala  Thr  Ser  Lys  His  Ala  Lys  Ile  Ser  Thr  Leu  Pro
               405                      410                     415

Gln  Leu  Asn  Ser  Ala  Leu  Val  Gln  Asp  Leu  Ala  Lys  Ala  Val  Ala  Lys
          420                      425                     430

Val ( 2 ) INFORMATION FOR SEQ ID NO:8:

( i ) SEQUENCE CHARACTERISTICS:
        ( A ) LENGTH: 432 amino acids
        ( B ) TYPE: amino acid
        ( C ) STRANDEDNESS: single
        ( D ) TOPOLOGY: linear ( i i ) MOLECULE TYPE: protein
        ( A ) DESCRIPTION:Cyclin B polypeptide sequence; Figure 3

( v i ) ORIGINAL SOURCE:
        ( A ) ORGANISM:Homo Sapiens ( x i ) SEQUENCE DESCRIPTION: SEQ ID NO:8:

Met  Leu  Gly  Asn  Ser  Ala  Pro  Gly  Pro  Ala  Thr  Arg  Glu  Ala  Gly  Ser
1                        5                       10                          15

Ala  Leu  Leu  Ala  Leu  Gln  Gln  Thr  Ala  Leu  Gln  Glu  Asp  Gln  Glu  Asn
                    20                      25                      30

```
Ile Asn Pro Glu Lys Ala Ala Pro Val Gln Gln Pro Arg Thr Arg Ala
         35                  40                  45
Ala Leu Ala Val Leu Lys Ser Gly Asn Pro Arg Gly Leu Ala Gln Gln
         50                  55                  60
Gln Arg Pro Lys Thr Arg Arg Val Ala Pro Leu Lys Asp Leu Pro Val
 65                  70                  75                  80
Asn Asp Glu His Val Thr Val Pro Pro Trp Lys Ala Asn Ser Lys Gln
                 85                  90                  95
Pro Ala Phe Thr Ile His Val Asp Glu Ala Glu Lys Glu Ala Gln Lys
            100                 105                 110
Lys Pro Ala Glu Ser Gln Lys Ile Glu Arg Glu Asp Ala Leu Ala Phe
            115                 120                 125
Asn Ser Ala Ile Ser Leu Pro Gly Pro Arg Lys Pro Leu Val Pro Leu
    130                 135                 140
Asp Tyr Pro Met Asp Gly Ser Phe Glu Ser Pro His Thr Met Asp Met
145                 150                 155                 160
Ser Ile Val Leu Glu Asp Glu Lys Pro Val Ser Val Asn Glu Asn Pro
                165                 170                 175
Asp Tyr His Glu Asp Ile His Thr Tyr Leu Arg Glu Met Glu Val Lys
            180                 185                 190
Cys Lys Pro Lys Val Gly Tyr Met Lys Lys Gln Pro Asp Ile Thr Asn
        195                 200                 205
Ser Met Arg Ala Ile Leu Val Asp Trp Leu Val Glu Val Gly Glu Glu
    210                 215                 220
Tyr Lys Leu Gln Asn Glu Thr Leu His Leu Ala Val Asn Tyr Ile Asp
225                 230                 235                 240
Arg Phe Leu Ser Ser Met Ser Val Leu Arg Gly Lys Leu Gln Leu Val
                245                 250                 255
Gly Thr Ala Ala Met Leu Leu Ala Ser Lys Phe Glu Glu Ile Tyr Pro
            260                 265                 270
Pro Glu Val Ala Glu Phe Val Tyr Ile Thr Asp Asp Thr Tyr Thr Lys
        275                 280                 285
Lys Gln Val Leu Arg Met Glu His Leu Val Leu Lys Val Leu Thr Phe
    290                 295                 300
Asp Leu Ala Ala Pro Thr Val Asn Gln Phe Leu Thr Gln Tyr Phe Leu
305                 310                 315                 320
His Gln Gln Pro Ala Asn Cys Lys Val Glu Ser Leu Ala Met Phe Leu
                325                 330                 335
Gly Glu Leu Ser Leu Ile Asp Ala Asp Pro Tyr Leu Lys Tyr Leu Pro
            340                 345                 350
Ser Val Ile Ala Gly Ala Ala Phe His Leu Ala Leu Tyr Thr Val Thr
        355                 360                 365
Gly Gln Ser Trp Pro Glu Ser Leu Ile Arg Lys Thr Gly Tyr Thr Leu
    370                 375                 380
Glu Ser Leu Lys Pro Cys Leu Met Asp Leu His Gln Thr Tyr Leu Lys
385                 390                 395                 400
Ala Pro Gln His Ala Gln Gln Ser Ile Arg Glu Asp Tyr Lys Asn Ser
                405                 410                 415
Lys Tyr His Gly Val Ser Leu Leu Asn Pro Pro Glu Thr Leu Asn Leu
            420                 425                 430
```

HUMAN CYCLIN E

This application is a continuation of Ser. No. 07/947,311, filed Sep. 16, 1992, now U.S. Pat. No. 5,449,755 which is a continuation-in-part of Ser. No. 07/764,309, filed Sep. 20, 1991, now abandoned.

This invention was made with government support under grant CA 48718 awarded by the National Institutes of Health. The government has certain rights in the invention.

1. Field of the Invention

This invention relates to genetic engineering involving recombinant DNA technology, and particularly to the identification of a nucleotide sequence encoding human cyclin E that controls the rate of cell growth by controlling progression at G1 phase of the cell cycle and entry into the S phase.

2. Background of the Invention

A major goal in studying the growth and differentiation of higher eukaryotic cells is to describe in biochemical terms the pathways, enzymes, and cofactors that regulate progression through the cell cycle, and in particular through the transitions from G1 phase into S phase, and from G2 phase into M phase. Proteins, now known as cyclins, were described in fertilized sea urchin and clam eggs as members of a small number of proteins whose synthesis was greatly stimulated following fertilization (in the appended Citations: Evans et. al., 1983) and whose levels decreased at each mitosis. Cyclin A (Swenson et al., 1986) and cyclin B (Pines and Hunt, 1987), were discovered to periodically accumulate in mitotic cells, and thus a role in the mitotic process was considered possible (Evans et al., 1983) even though the biochemical basis was unclear. Results of genetic and biochemical analysis now support a role for certain cyclins in meiosis and mitosis. Microinjection of clam or sea urchin cyclin B1 mRNA into Xenopus oocytes (Pines and Hunt, 1987); Westendorf et al., 1987) is reportedly sufficient to drive the cell through meiosis I and II, and cyclin B may be the only protein whose synthesis is required for each mitotic cycle in early Xenopus embryos (Murray and Kirschner, 1989). Conversely, destruction of cyclin B1 and B2 mRNA may cause fertilized Xenopus eggs to arrest after DNA replication but before mitosis (Minshull et al., 1989). Besides Xenopus, in the yeasts S. pombe and S. cerevisae cyclin B reportedly plays a role in regulating transit through mitosis (Hagan et al., 1988; Ghiara et al., 1991; Surana et al., 1991; Booher and Beach, 1987; Booher et al., 1989; Hagan et al., 1988; Ghiara et al., 1991; Surana et al., 1991) by exerting mitotic control over activation of a p34 CDC2 protein kinase (reviewed in Nurse, 1990; Cross et al., 1989). In the latter case, CDC2 kinase is reportedly not catalytically active as a monomer, but following binding to the cyclin B and a series of phosphorylations and dephosphorylation steps, the kinase activity is generated (Simanis and Nurse, 1986; Draetta and Beach, 1988; Pondaven et al., 1990; Solomon et al., 1990; Gould and Nurse, 1989; Enoch and Nurse, 1990; Solomon et al., 1992).

Cyclin B-dependent activation of a p34 CDC2 kinase may also be necessary to initiate mitosis in certain somatic cells (Nurse, 1990; Cross, 1989; Maller et al., 1991), but activation alone may not be the only event required (Lamb et al., 1990; Osmani et al., 1991; Amon et al., 1992; Sorger et al., 1992). S. cerevisiae apparently has a CDC2 homologue termed CDC28. The CDC2 and CDC28 gene products appear to be structurally similar (Lorincz & Reed, 1984; Hindley & Phear, 1984) and functionally homologous (Beach et al., 1982; Booher & Beach 1987). They encode a serine/threonine protein kinase that is the homolog of the 34 kDa protein kinase in vertebrate and invertebrate mitosis promoting factor (MPF; Lee & Nurse, 1987; Arion et al., 1988; Dunphy et al., 1988; Gautier et al., 1988; Labbe et al., 1988). CDC28 may require different cyclins for the cell cycle transitions at G2/M and at G1/S: namely, at G2/M CDC28 reportedly binds to and is activated by B-type cyclins (Ghiara et al., 1991; Surana et al., 1991), while at G1/S CDC28 is reportedly activated by CLN-type cyclins, (i.e., CLN1, CLN2 and CLN3; Sudbery et al., 1980; Nash et al., 1988; Cross, 1988, 1990; Hadwiger et al., 1989; Richardson et al., 1989; Wittenberg et al., 1990).

CLN1 and CLN2 cyclins are periodically expressed during the cell cycle, peaking in abundance at the G1/S transition point (Wittenberg et al., 1990; Cross and Tinkelenberg, 1991) and accumulation of the CLN proteins in yeast cells may be rate limiting for the transition from G1 into S phase of the cell cycle.

For the purposes of the present disclosure, the term "CDC protein kinase" is used synonymously with the recently adopted "cell division kinase (CDK)" nomenclature.

The p34 CDC2 kinase activity apparently oscillates during the cell cycle (Mendenhall et al., 1987; Draetta & Beach 1988; Labbe et al., 1989; Moreno et al., 1989; Pines & Hunter, 1990), and this oscillation of activity is not attributable to variations in the amount of the CDC2 gene product present in cells (Durkacz et al., 1986; Simanis & Nurse, 1986; Draetta & Beach, 1988). Rather, CDC2 kinase activity appears to be influenced by interactions of the kinase with other proteins, including (as discussed above) the cyclins (Rosenthal et al, 1980; Evans et al., 1983; Swenson et al., 1986; Draetta et al., 1989; Meijer et al., 1989; Minshull et al., 1989; Murray & Kirschner, 1989; Labbe et al., 1989; Soloman et al., 1990; Gautier et al., 1990; reviewed in Murray & Kirschner, 1989; Hunt, 1989). Apparently an association between a p34 CDC2 protein and a B-type cyclin is necessary for the activation of the p34 kinase at the onset of mitosis in a wide variety of organisms including yeast (Booher & Beach, 1987; Hagan et al., 1988; Moreno et al., 1989; Soloman et al., 1988; Booher et al., 1989; Surana et al., 1991; Ghiara et al., 1991) and humans (Draetta & Beach, 1988; Pines & Hunter, 1989; Riabowol et al., 1989).

In budding yeasts a major control decision point in cell proliferation reportedly occurs during G1, i.e., at a point termed START, where entry of cells into S phase is restricted until certain conditions have been satisfied (Hartwell, 1974). The START transition appears to require a CDC28 or cdc2 gene product (Hartwell et al., 1973, 1974; Nurse & Bisset, 1981), but the biochemical pathways that activate CDC28 at START are not completely understood. The latter pathways may involve the CLN1, CLN2 and CLN3 cyclins and activation of CDC28 because cells deficient in all three CLN proteins arrest at START; and although they continue to grow they are unable to enter S phase (Sudbery et al., 1980; Nash et al., 1988; Cross, 1988, 1990; Hadwiger et al., 1989; Richardson et al., 1989; Wittenberg et al., 1990). CLN2, and probably CLN1 and CLN3, may form complexes with CDC28 kinase prior to or at START (Wittenberg et al., 1990). The CLN1 and CLN2 oscillates during the cell cycle, but maximal levels are reportedly observed in late G1 (i.e., rather than late G2; Wittenberg et al., 1990).

Little is currently known about the biochemical pathways that control the start of DNA synthesis in higher eukaryotic cells or the extent to which these pathways resemble those in yeast. However, in human cells (as in budding yeast) the predominant mode of control of cell proliferation appears to occur during the G1 phase of the cell cycle (Zetterberg &

Larson, 1985; Zetterberg, 1990). The kinetics of passage through G1 in mammalian cells suggest a single decision point, termed the "restriction point", that regulates commitment of a cell to initiate DNA synthesis (Pardee, 1974). Prior to the restriction point, progress through G1 is sensitive to the growth state of the cell (e.g., reducing the rate of protein synthesis or removing a growth factor apparently may delay entry into S phase and can even cause cell cycle arrest), however, after the restriction point the cell cycle becomes substantially less responsive to these signals (reviewed in Pardee, 1989). Unlike yeasts, CDC2 cyclin appears to be diversified into a small protein family in mammalian cells (Paris et al, 1991; Elledge and Spotswood, 1991; Tsai et al., 1991; Koff et al., 1991) and CDC2/28 activities may also be split among several different kinase family members (Fang and Newport, 1991). Certain cyclins may have roles in G1 regulation in higher eukaryotes similar to those reported in yeast. For example, cyclin A synthesis reportedly begins late in G1 and it may activate both p34 CDC2 and certain related p33 CDK2 kinases (Giordano et al, 1989; Pines and Hunter, 1990; Marraccino et al., 1992; Tsai et al., 1991). Inhibition of cyclin A function may also reportedly block a START-like function of S phase in certain cells (Girard et al., 1991) and cyclin A reportedly is able to associate with certain transforming and growth suppressing factors (Hunter and Pines, 1991). However, despite these apparent results supporting a role for cyclin A in regulating a START-like function in higher eukaryotes, there are also some reasons to doubt that cyclin A is functionally homologous with budding yeast CLN proteins. Several laboratories have recently identified two novel cyclins in mammalian cells that are not present in yeasts, i.e., cyclin C and cyclin D. The cyclin D gene was reported as a gene induced by CSF-1 in murine macrophages in late G1 (Matshushime et al., 1991) and the gene may have a chromosomal location at a breakpoint subject to possible rearrangement in human parathyroid tumor (Motokura et al., 1991). Cyclin C, as well as cyclin D, have also been reportedly identified in human and Drosophila cDNA libraries by screening for genes capable of complementing mutations in *S. cerevisae* CLN genes (Laheu et al,. 1991; Lew et al., 1991; Leopold and O'Farrell, 1991; Xiong et al., 1991). While the results are consistent with G1 functions for cyclin C and cyclin D, cyclin B (a mitotic cyclin) was also found to be capable of rescuing the latter *S. cerevisae* CLN mutants, indicating that yeast complementation assays may not necessarily identify cyclins that perform similar functions in higher eukaryotic cells.

The similarities between the restriction point in mammalian cells and START in yeast has suggested a possible role for a p34 CDC2 kinase. In support of this hypothesis, a human CDC2 gene has been found that may be able to substitute for the activity of an *S. pombe* cdc2 gene in both its G1/S and G2/M roles (Lee & Nurse, 1987). Also, cell fusion experiments offer circumstantial evidence in support of the hypothesis (Rao & Johnson, 1970) since a diffusible trans-acting factor is reportedly involved in activation of DNA synthesis when S phase cells were fused to G1 cells. However, the relationship between the latter S phase activator and the p34 CDC2 kinase remains unclear. Recently cyclin-CDC2 complexes have reportedly been isolated from human S phase cells and shown to be active in inducing SV40-DNA replication when they were added to extracts of G1 cells (D'Urso et al., 1990). Antisense oligonucleotides directed against the human CDC2 mRNA are reportedly inhibitory for human PHA-activated T cells at entry to S phase (Furakawa et al., 1990). In other higher eukaryotic cells it has been reported that depletion of CDC2 protein from Xenopus extracts can block DNA replication (Blow & Nurse, 1990). Despite recent suggestive reports, the pathway that activates p34 kinase during the G1 phase of the human cell cycle is not currently understood.

By analogy with the CLN-dependent activation of CDC28 at START in yeast, it is possible that specific G1 cyclins may play a role in regulating the human p34 kinase during the G1 to S phase transition. To test this idea experiments were conducted herein to determine whether human cells contain specific cyclins that can replace the yeast *S. cerevisae* CLN proteins. This assay identified a new human cyclin, cyclin E.

SUMMARY OF THE INVENTION

The invention provides isolated nucleic acid molecules capable of hybridizing under stringent conditions to the nucleotide sequence residing between positions 1 and 1185 of the human cyclin E cDNA sequence shown in FIG. 2. Such nucleic acid molecules preferably encode cyclin E polypeptides capable of binding and activating a cell division kinase (e.g., CDC2, CDC28, CDK2-XL, CDC2-HS, and CDK2-HS). The cyclin E polypeptide is typically also capable of shortening the G1 phase of the cell cycle. The invention also provides polypeptides encoded by the aforesaid nucleic acid molecules, and immunologic binding partners capable of specifically binding the polypeptides.

Cyclin E functions specifically during the late G1 and early S phases of the cell cycle by binding and activating a CDC2 related protein kinase, CDK2. The levels of the cyclin E/CDK2 polypeptide complexes are cell cycle-regulated, and peak in abundance in late G1 phase of the cell cycle. Constitutive expression of cyclin E in cells is alone sufficient to shorten the G1 phase of the cell cycle and promote cell growth. Increasing or decreasing the levels of cyclin E in a cell increase or decreases cell growth, respectively. Detecting the levels of cyclin E in cells such as tumor cells may provide information on their rate of growth. Rearrangement of the location of cyclin E at chromosomal breakpoints may change the rate of cell proliferation.

BRIEF DESCRIPTION OF THE DRAWINGS

FIG. 2 (SEQ. ID. NOS. 1–2) shows the sequence of cyclin E: DNA and predicted protein sequence of the cyclin E cDNA that complemented the triple cln deletion.

FIG. 3 shows alignment of the protein sequences of human cyclins A, B, and E: Protein sequences of cyclins A, B, and E were aligned to maximize homology. Boxes indicate identical amino acids. Amino acid shared by all three cyclins are shown in bold type above the three sequences. The area highlighted by double bold lines is a domain highly conserved among all known cyclins (the "cyclin box"). The domain highlighted by single bold lines is the mitotic destruction motif shared by all A- and B-type cyclins.

FIG. 4 shows efficiency of rescue of the triple cln deficiency by human cyclins E and B in CDC28 or cdc28-13 strains: All strains tested were cln1–cln2–cln3–(pGAL-CLN3); these strains were transformed with the indicated vector plasmids, pADNS or pADANS, or the vector plasmids containing either human cyclin E or B by selecting for leucine prototrophy. The vector pADNS uses the yeast ADH promoter for expression of the cDNA. The vector pADANS is identical to pADNS except that the expressed protein is fused at its amino terminus to the first 10 amino acids of the ADH protein. No transformants could be obtained with the plasmid pADNS-CYC B, suggesting it was lethal. The number of viable colonies in an inoculum of stationary phase culture in galactose was determined by serial dilution followed by 4–5 days growth on both galactose- and glucose-containing medium at 30° C. The plating efficiency is defined as the number of glucose-viable colonies divided by the number of galactose-viable colonies. Only colonies resulting from plasmid bearing cells are used in the calculation. Both YC and YEP media were used with comparable results. The vector and pADNS-CYC E values were determined in four experiments using two different pairs of CDC+ and cdc28-13 strains (one CDC+ and one cdc28-13 strain tested in parallel in each experiment). The pADANS-CYC E values come from a single experiment. The cyclin B values were determined in two experiments, both with the same pair of CDC+ and cdc28-13 strains. All strains were isogenic. The ranges of values for the CDC+ strains were: for pADNS-CYC E, 0.12–0.4; for pADANS-CYC B, 0.19–0.33; for the cdc28-13 strain pADNS-CYC E, 0.0006–0.008; and for pADANS-CYC B, 0.2–0.4. With both cyclin E plasmids the colony sizes for cdc28-13 strains on glucose medium were significantly smaller than colony sizes for CDC+ strains; for the cyclin B plasmid the colony sizes were similar in the CDC+ and cdc28-13 strains.

FIG. 5 shows construction of a yeast strain in which CDC28 is defective for START but not G2/M: Yeast strain 1238-14C-cycE has the following relevant genotype: cln1$^-$cln2$^-$cln3$^-$cdc28$^{13}$ (pADH-cycE-TRP1,pGAL-CLN3-URA3). The putative cyclin-cdc28-13 complexes which control the G1/S and G2/M transitions in this strain are indicated. Shown are cyclin-cdc28-13 complexes that form on either galactose or glucose and the functional activity of those complexes at either 30° or 38° C. CLB is the nomenclature used to designate the S. cerevisae homologs of the B-type cyclins. On glucose at 30° C. this strain is defective for START but not G2/M.

FIG. 6 shows efficiency of rescue of the triple cln deficiency in a cdc28-13 strain by human cyclin E in conjunction with human CDC2 or human CDK2: A strain of genotype cln1$^-$cln2$^-$cln3$^-$cdc28-13 (pGAL-CLN1/URA3) was cotransformed with either pMAC-TRP1-CYC E and pADNS-LEU2-CDC2-HS or with pMAC-TRP1-CYC E and pADNS-LEU2-CDK2-HS. Transformants were selected for leucine, tryptophan, and uracil prototrophy on galactose. Two independent transformants were grown nonselectively overnight, and plasmid loss events were identified following colony purification. This resulted in the generation of isogenic sets of strains, either containing both cyclin E and CDC2-HS (or CDK2-HS) or either gene alone. Two such sets were generated for each cotransformation. The twelve strains were tested in the quantitative plating assay described above (see legend to FIG. 4) except that plating efficiencies were measured both at 30° and 38° C. Strains containing the same plasmid combinations behaved very similarly, and their data are pooled in the table. Note that unlike cyclin E plasmids used in the experiments in FIG. 4, the pMAC-TRP1-CYC E plasmid used in these experiments gives essentially no rescue of the cln1$^-$cln3$^-$cdc29-13 strain.

FIGS. 9A–9E shows differential levels of cyclin E-kinase complexes in different subpopulations of exponentially growing MANCA cells that were fractionated by centrifugal elutriation into different stages of the cell cycle, as described in Example 8.

FIG. 9A shows graphically the DNA content (ordinate) of exponentially growing MANCA cells measured cytofluorimetrically in different elutriated fractions (abscissa).

FIG. 9B shows graphically the level of cyclin E H1 histone kinase activity in the elutriated fractions of FIG. 9A.

FIG. 9C shows graphically the level of cyclin A H1 histone kinase activity in the elutriated fractions of cells of FIG. 9A.

FIG. 9D shows graphically the DNA content (ordinate) of MANCA cells in different elutriated cell fractions released into the G1 phase of the cell cycle for 3, 4, 5, 6, or 7 hours after nocodazole-induced metaphase.

FIG. 9E shows a bar graph depicting the levels of cyclin A and cyclin E associated H1 histone kinase activity.

FIG. 10A shows an autoradiogram of $^{32}$P-labeled H1 histone. The phosphorylation of H1 histone was catalyzed by immunoprecipitates of 208F cells grown in 10% or 0.1% calf serum. The level of cyclin E-associated kinase activity was markedly reduced in quiescent (0.1% CS) cells as compared to growing cells (10% CS).

FIG. 10B shows an autoradiogram of $^{32}$P-labeled H1 histone. The phosphorylation of H1 histone catalyzed by immunoprecipitates was determined for PC-12 cells grown in the presence or absence of nerve growth factor. The level of cyclin E-associated kinase activity was markedly reduced in differentiated (quiescent) cells (−NGF) as compare to rapidly proliferating cells (+NGF).

FIGS. 11A–11E, discussed in Example 9, shows the results of studies designed to investigate increased levels of constitutively expressed cyclin E in Rat-1 cells transduced with either a retroviral vector encoding cyclin E (LXSN-cyclin E), or the LXSN vector as a negative control.

FIG. 11A shows an autoradiograph of a Western immunoblot of Rat-1 cellular lysates transduced with either LXSN-cyclin E (lane 2) or, as a negative control, the LXSN vector alone (lane 1). Increased levels of cyclin E, as measured by histone H1 kinase activity, were visible in LXSN-Cyclin E transduced cells relative to the control.

FIG. 11B shows an autoradiogram of $^{32}$P-labeled histone H1 catalyzed by cyclin E-associated kinase in cellular immunoprecipitates of LXSN-cyclin E transduced Rat-1 cells (lane 2) or LXSN transduced control Rat-1 cells (lane 1). Increased cyclin E expression was visible in cellular immunoprecipitates of LXSN-cyclin E transduced Rat-1.

FIGS. 11C–11D graphically presents the results of flow cytometric measurement of nuclear DNA content in Rat-1 cells transduced with either LXSN (Rat-1/control) (FIG. 11C) or the LXSN-cyclin E retroviral vector (Rat-1/cyclin E) (FIG. 11D), as well as the calculated fraction of the cells in each cell subpopulation that was in the G1, S, or G2/M phases of the cell cycle.

FIG. 11E graphically presents the results of immunochemical detection of BrdU (5-bromodeoxyuridine) incorporation into nuclear DNA of Rat-1 cells transduced with LXSN-cyclin E (solid diamonds) or LXSN (open squares) as a function of time after removing a mitotic block. Only cells synthesizing DNA (S-phase cells) incorporate BrdU and score positive in this assay, and so the assay measures the rate at which cells transition from the conclusion of one mitosis into DNA synthesis for the next round of mitosis. The results show that LXSN-cyclin E transduced cells transition from mitosis into S-phase more rapidly than LXSN-transduced control cells.

FIG. 14A shows an immunoblot of purified cyclin E:CDC2 complexes separated into its two constituent proteins on SDS-PAGE and visualized by immunoblotting with antibodies specific for the C-terminus of human p34 CDC2. Lanes 1 and 8 were negative control samples prepared from an incubation of cell extracts with αPI; lanes 2 and 7 were negative controls from an incubation of cell extracts with Sepharose beads (SEPH); lanes 3 and 6 show cyclin E:CDC2 complexes purified by affinity chromatography or anti-p34 CDC2 Sepharose; lanes 4 and 5 show cyclin E:CDC2 complexes purified by affinity chromatography on anti-cyclin E-Sepharose; lanes 9–11 labeled "−−" are negative control samples prepared in a manner identical to lanes 1–8, but without cell extract.

FIG. 14B shows an immunoblot of purified cyclin E:CDK2 complex separated into its two constituent proteins and CDK2 visualized by immunoblotting with antibodies specific for the C-terminus of human CDK2. The abbreviations used are as indicated in FIG. 14A. The location on SDS-PAGE of CDK2 in nonaffinity-purified SDS-PAGE purified cell extract ("EX") from cells at the G1/S boundary is shown in lane 8.

FIG. 15A shows graphically the DNA content (ordinate) in various fractions of elutriated MANCA cells as determined by flow cytometry of propidium iodide stained nuclei.

FIG. 15B shows graphically the $^{125}$I-Protein A CPM bound by the CDK2 polypeptide bands immunoblotted in FIG. 15C.

FIG. 15C shows Western immunoblots measuring the level of expression of cyclin E in each elutriated subpopulation of cells (from FIG. 15A) as determined by immunoaffinity purification of cyclin E:CDK2 complexes with anti-cyclin E-Sepharose followed by SDS-PAGE, and visualization of the proteins in the complex by Western immunoblot analysis using anti-CDK2, $^{125}$I -Protein A, and autoradiography.

FIG. 15D shows graphically the $^{125}$I-Protein A CPM bound by the cyclin E ("cycE") polypeptide bands immunoblotted in FIG. 15E.

FIG. 15E shows Western immunoblots measuring the level of expression of cyclin E in elutriated subpopulations of cells from FIG. 15A by the methods described in FIG. 15C, but using anti-cyclin E and $^{125}$I-Protein A to visualize the level of cyclin E instead of anti-CDK2.

FIG. 15F shows graphically the level of $^{125}$I-Protein A bound by anti-cyclin E:cyclin E bands in Western immunoblots as a function of the amount of cellular extract (elutriated fraction 3 extract) used in the method of FIGS. 15B–15E. The results show that increasing the amount of cyclin E increased the amount of signal in the immunoassay for cyclin E.

FIG. 16A shows the results of experiments assaying phosphorylase kinase activity in cyclin E:CDK2 complexes immunoprecipitated with antibody specific for CDK2 (Anti-CDK2). The complexes were formed in the cell extracts of hydroxyurea-arrested cells (HU) and in extracts of G1 phase cells (G1 extract) in the absence (0) or presence of differing amounts (5,1,0.2) of recombinant cyclin E. Kinase activity in the immunoprecipitates was determined using histone H1 as a substrate, SDS-PAGE, and phosphor imaging of the $^{32}$P-labeled histone H1 bands in the gels. The results show that the addition of cyclin E to G1 cell extracts activated latent kinase activity in the extracts in a dose-dependent manner, i.e., the level of kinase activity measured was dependent upon the amount of cyclin E added.

FIG. 16B shows the results of experiments assaying phosphorylase kinase activity in cyclin E complexes. The experiments were conducted as described in FIG. 16A, above, but using antibodies specific for cyclin E (Anti-cyclin E) instead of Anti-CDK2. The results confirm those presented in FIG. 16A, above: namely, cyclin E activates a latent CDC kinase activity in extracts of G1 cells in a dose-dependent manner.

FIG. 16C shows the results of experiments designed to assay for the phosphorylase kinase activity in cyclin E:CDC2 complexes. The experiments were conducted as described in FIG. 16A, above, but using antibodies specific for CDC2 (Anti-CDC2). The results show minimal to no CDC2 kinase activity in G1 extracts of cells even when cyclin E was added.

FIG. 18A shows the results of experiments designed to evaluate the rate at which LXSN-cyclin E-transduced (RAT1/cyclin E) or LXSN-transduced (RAT1/LX) control cells initiate DNA synthesis following release of a nocodazole block. The results show that the cyclin E-transduced cells initiated DNA synthesis more than 2–3 hours earlier than control-transduced cells, and the rate of nuclear labeling (i.e., initiation of DNA synthesis) was also greater in the cyclin E-transduced cells (as evidenced by the differing slopes of the two curves).

FIG. 18B shows the results of experiments designed to evaluate the growth factor dependence for initiating DNA synthesis in LXSN-cyclin E-transduced and LXSN-transduced control cells. Both types of cells were cultured in medium containing either 1% or 0.1% bovine calf serum. The results show that a) LXSN-cyclin E-transduced cells initiated DNA synthesis more rapidly than control cells following release of the nocodazole block in either 1% or 0.1% serum, and b) cyclin E-transduced cells were less dependent on growth factors than LXSN-transduced control cells as evidenced by their more rapid initiation of DNA synthesis in low serum (i.e., the LXSN-cyclin E-transduced cells initiated DNA synthesis more than 6–8 hours earlier than LXSN-transduced cells in 0.1% serum), and the cyclin E-transduced cells also proliferated more rapidly in the low serum conditions than the control (i.e., as determined by comparing the slopes of the the two transduced cell types grown in 0.1% serum).

DETAILED DESCRIPTION OF THE PREFERRED EMBODIMENT

Figure 1A:
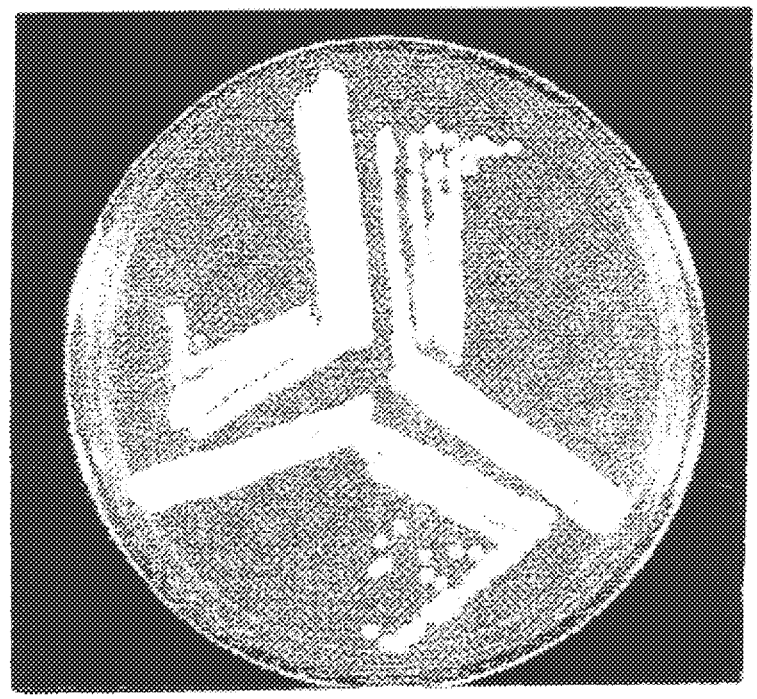
FIG. 1 shows complementation of the triple cln deletion by human cyclin E: *S. cerevisae* strain 589-5 contains deletions of the chromosomal CLN1, -2, and -3 genes and contains the GAL1-CLN3 gene on a multicopy episome. It was transformed with the pADNS expression vector or the pADNS vector containing a human cyclin E cDNA. Transformants, and the parental strain, were streaked on galactose and glucose and grown for 3 days at 30° C.

A new human cyclin, named cyclin E, was isolated by complementation of a triple cln deletion in S. cerevisae. Cyclin E showed genetic interactions with the CDC28 gene suggesting that it functioned at START by interacting with the CDC28 protein. Two human genes were identified that could interact with cyclin E to perform START in yeast containing a cdc28 mutation. One was cdc2-HS and the second was the human homolog of Xenopus CDK2. Cyclin E produced in E. coli, bound and activated the CDC2 protein in extracts from human G1 cells, and antibodies against cyclin E immunoprecipitated a histone H1 kinase from HeLa cells. The interactions between cyclin E and CDC2, or CDK2, may be important at the G1 to S transition in human cells.

The invention provides nucleic acid molecules capable of hybridizing under stringent conditions to the human cyclin E cDNA shown in FIG. 2 from position 1 to 1185. Although only a single (+) strand of the cDNA is shown in FIG. 2, those skilled in the art will recognize that its complementary (−) strand is thereby disclosed as well. By nucleic acid molecule is meant DNA, RNA, and/or synthetic nucleotide sequences such as oligonucleotides that are the same as, homologous with, or complementary to, at least one helical turn (about 10 to 15 nucleotides) of the illustrated cyclin E nucleotide sequence. The invention provides more than three cyclin E cDNAs resulting from alternative splicing of cyclin E mRNAs, genetic polymorphism, and translocation in tumorigenesis. Those skilled in the art will recognize that the members of this closely related group of cyclin E nucleic acids are readily identified by their ability to hybridize under stringent conditions with all or portions of the nucleotide sequence of FIG. 2 or its complementary (−) strand. By capable of hybridizing under stringent conditions is meant annealing of a nucleic acid molecule to at least a region of the disclosed cyclin E nucleic acid sequence (whether as cDNA, mRNA, or genomic DNA) or to its complementary strand under standard conditions, e.g., high temperature and/or low salt content, which tend to disfavor hybridization of noncomplementary nucleotide sequences. A suitable protocol (involving 0.1×SSC, 68° C. for 2 hours) is described in Maniatis, T., et al., *Molecular Cloning: A Laboratory Manual*, Cold Springs Harbor Laboratory, 1982, at pages 387–389. Such hybridizing nucleic acid molecules may be related to the disclosed sequence by deletion, point mutation, base substitution, frameshift, alternative ORFs, mRNA splicing and processing, or post-transcriptional modification (e.g., methylation and the like). For example, antisense nucleic acids are provided having nucleotide sequences complementary to the cyclin E sequence and characterized by the ability to inhibit expression of a cyclin E gene, e.g., by binding and inhibiting translation of a cyclin E mRNA. Antisense nucleic acids may be encoded within a host cell, e.g., following transduction or transfection of the cell with a vector DNA or RNA sequence encoding an antisense nucleic acid, or, alternatively, the antisense nucleic acids may be synthetic oligonucleotides. Such antisense oligonucleotides are introduced into cells by a variety of means, e.g., with retroviral vectors encoding antisense mRNA in the cell, or by fusing the cell with liposomes containing an antisense oligonucleotide and the like. The subject antisense nucleic acid molecules are characterized by their ability to hybridize under stringent conditions with the illustrated cyclin E nucleic acid, its complementary strand, 5' transcription regulatory regions of a cyclin E gene, or translation regulatory regions of a cyclin E mRNA.

The isolated nucleic acids of the invention preferably encode cyclin E polypeptides. Such polypeptides are not necessarily encoded by the aforesaid isolated nucleic acid molecules, since those skilled in the art will recognize that the disclosed cyclin E nucleotide sequence permits construction of a variety of synthetic polypeptides. Such synthetic polypeptides may vary in length (e.g., from about 5 amino acids to many hundreds of amino acids) and be constructed corresponding to selected regions of the encoded cyclin E polypeptide. The subject cyclin E polypeptides thus encompass isolated cyclin E polypeptides (i.e., found in normal cells), mutant polypeptides (e.g., resulting from mutagenesis, or found in tumor cells), and chemically modified polypeptides (e.g., having one or more chemically altered amino acids, in which case a designated amino acid can be converted into another amino acid, or chemically substituted or derivatized and the like). Functional sites in the cyclin E polypeptides are identified by constructing mutants of the cyclin E nucleic acid, e.g., and testing the constructs for expression products having altered functional properties such as failure to bind or activate a CDC protein kinase, or failure to advance the cell cycle. Particularly useful for constructing such mutants are regions of conserved nucleotide or amino acid sequence, e.g., conserved between cyclins A, B, C, D, and E, or conserved among the members of the cyclin E family. Conserved regions of cyclin E are functional and protein-structural regions of the polypeptide.

In an illustrative preferred aspect, expression of a cyclin E polypeptide in a cell allows levels of cyclin E in the cell to rise to a point where cyclin E binds and activates a CDC protein kinase, and eliminates certain growth factor and serum requirements for progression of the cell through the G1 phase of the cell cycle. As a result, the G1 phase of the cell cycle is shortened. The G1 phase commonly lasts about 8 to about 12 hours, and expression of a cyclin E polypeptide in a cell (or exposure of a cell to a cyclin E polypeptide) may shorten G1 phase by about 1 hour to many hours. That a cyclin of the invention shortens the G1 phase of the cell cycle can be readily determined by those skilled in the art by using a model test system such as that provided below in the Examples, e.g., by the "598-5" or "1238-14C" strains of yeast. Alternatively, a mammalian cell such as an NIH3T3 cell may be transfected or transduced with an expression vector containing a cyclin E-hybridizing nucleic acid and the length of the G1 phase of the 3T3 cell cycle can then be determined in kinetic cell cycle assays such as those illustrative examples provided below. For instance, those skilled in the art will recognize that progression of cells from M to S phase can be measured (i.e., in hours and minutes) by determining tritiated thymidine or bromodeoxyuridine (BrdU) incorporation. Cyclin E nucleic acid, when transfected or transduced into test cells, induces either a faster progression of the cells from the M phase to the S phase; or a progression of the cells from M to S without requiring exogenous stimulae, i.e., serum or growth factors and the like. In either case, introducing the subject cyclin into the test cell results in a shortening of the G1 phase and a more rapid progression from M to S.

Representative examples of CDC protein kinases to which cyclin E binds include CDC2, CDC28, CDCK2-XL, CDC2-HS, and CDK2-HS. (Note that in this terminology "HS" designates *Homo sapiens* and "XL", *Xenopus laevis*.) The invention also provides methods for identifying and cloning other CDC kinases that are bound and activated by cyclin E (see Example 10, below). Those skilled in the art will understand that synthetic cyclin E polypeptides may be readily constructed by modifying the disclosed amino acid sequence and testing for altered functional properties, i.e., altered binding, activation of a CDC protein kinase, and/or altered ability to shorten the G1 phase of the cell cycle. Such synthetic cyclin E polypeptides are useful competitive and noncompetitive inhibitors of a normal or mutant cyclin E (i.e., derived from a normal or mutant cell) or of its CDC protein kinase binding partner. Such synthetic polypeptides also include polypeptide antagonists or agonists useful for changing the functional properties of the cyclin E:CDC protein kinase complex, e.g., by increasing, decreasing, or otherwise modifying or modulating: a) the phosphorylase activity activated by the CDC protein kinase; b) the activity of the cyclin E, e.g., for activating the CDC protein kinase; c) the cell cycle promoting activity of the cyclin E:cell division kinase complex; and/or, d) transcriptional regulatory factors that bind the 5' region of the cyclin E gene.

Skilled artisans will further understand that the disclosure herein of recombinant cyclin E nucleic acids, cells, and in vitro assays provide opportunities to screen for compounds that modulate, or completely alter, the functional activity of a cyclin E protein or cyclin E nucleic acid in a cell. In this context "modulate" is intended to mean that the subject compound increases or decreases one or more functional activity of a cyclin E protein or nucleic acid, while "alter" is intended to mean that the subject compound completely changes the cyclin E protein or nucleic acid functional activity to a different functional activity. In this context, an example of a compound that "modulates" the activity of a cyclin E protein is an inhibitor capable of decreasing the level of CDC kinase activity following binding of a cyclin E to the CDC kinase; and, an example of a compound that "alters" the activity of a cyclin E protein is an agent that induces cyclin E to bind to CDC2 instead of to CDK2.

The screening assays illustrated in the Examples (below) include biochemical assays (e.g., measuring effects of cyclin E protein on CDC2 and CDK2 phosphorylase activity), and cellular in vitro assays (e.g., measuring the effects of cyclin E expression on cell proliferation). The illustrative biochemical assays may be particularly useful in screening for compounds modulating a cyclin E molecular activity, while the cellular assays may be particularly useful in screening for compounds altering a cyclin E activity in a cell. For example, in proliferating cells cyclin E participates with other cyclins, CDC kinases, growth factor second messengers, transcription regulatory factors and the like in controlling the proliferative response of a cell to its environment. Those skilled in the art will understand that binding of a ligand at a molecular binding site can be modulated in a direct manner (e.g., by blocking the site), as well as altered in an indirect manner (e.g., by conformational changes induced following binding of a second (different) ligand at a distant site). In this regard, it is likely that the binding site specificity of cyclin E for a particular CDC kinase (or some other cellular control factor, as discussed below), can be completely altered (i.e., to bind a different ligand) by agents that bind at distant sites in the cyclin E polypeptide. Examples of compounds that may be screened in the latter several assays include at least nucleic acids (e.g., DNA oligonucleotide aptamers that bind proteins and alter their functions), proteins, carbohydrates, lectins, organic chemicals, and the like. Such screening assays may be useful for identifying candidate therapeutic agents that may provide drugs useful in animals and humans.

It is still further understood that, due to the significance of cyclin E and the cyclin E:CDC protein kinase in the cell cycle, innate regulatory mechanisms exist in cells for regulating their activity by binding to cyclin E or to complexes containing cyclin E. Such regulatory factors can include, at least: a) cofactors that bind to the complex and exert regulatory action by destabilizing or stabilizing the complex; b) agents that modulate or alter the activity of the complex by inducing conformational changes in the CDC protein kinase and/or cyclin E polypeptides as they are bound together in the complex; c) enzymes that inactivate one or both members of the complex; and, d) cellular control factors (e.g., signal transduction second messengers, transcription regulatory factors, and the like) that bind cyclin E or cyclin E complexes and modulate or alter functional activity. Thus, artificial polypeptides can be constructed that control the activity of the cyclin E:CDC protein kinase kinase complexes in the cell by inhibiting or promoting the activities of such regulatory factors. Those skilled in the art will recognize that the functional regions of cyclin E represent particularly attractive targets for three-dimensional molecular modeling and for the construction of mimetic compounds, e.g., organic chemicals constructed to mimic the three-dimensional interactions between the cyclin E and its CDC protein kinase binding partner. In a particularly preferred embodiment, the invention provides isolated nucleic acid molecules that encode artificial cyclin E polypeptides that bind to, but do not activate, CDC protein kinases.

In other preferred embodiments of the invention, polypeptides are provided that are encoded by nucleic acids corresponding to the following regions of the cyclin E nucleotide sequence (i.e., regions that are conserved between cyclins A, B, and E): namely, a) a carboxy-terminal leucine repeat sequence (i.e., residing between positions 640 and 1185, and more particularly between positions 631 and 936, of the cyclin E cDNA shown in FIG. 2); b) an MRAIL sequence (i.e., residing between positions 385 and 645 of the cyclin E cDNA shown in FIG. 2); and c) a C-terminal sequence region (i.e., residing between positions 1048 and 1080 of the cyclin E cDNA shown in FIG. 2). The MRAIL sequence is necessary, but not sufficient, for binding to a cell division kinase.

It is further understood that mutant cyclin E nucleotide sequences may be constructed from the sequence shown in FIG. 2. The subject mutant cyclin E nucleotide sequences are recognized by their ability to encode mutant cyclin E polypeptides that may have binding affinity for a CDC kinase (e.g., CDK2) polypeptide that is higher or lower than that exhibited by a cyclin E polypeptide for a CDC kinase in a non-transformed mammalian cell. The subject mutant polypeptides also may alter (i.e., increase or decrease) the enzyme activity of the CDK2 kinase when the subject mutant cyclin E polypeptide and CDK2 are resident together in a complex. Illustrative examples of changed enzyme activity include: a) increased or decreased enzymatic activity (e.g., Km, Vmax, kcat, and the like); b) changed stability of the kinase in the complex (e.g., to time-dependent decay of the complex or the enzyme activity); c) changed susceptibility of the kinase to proteolytic inactivation; d) changed susceptibility of CDK2 to dissociate from the cyclin E:CDK2 complex in response to binding of regulatory factors (discussed above) by the complex; or e) changed sensitivity of the kinase in the complex to competitive or noncompetitive inhibitors. Skilled artisans will recognize a variety of methods by which the sequence in FIG. 2 may be mutated (e.g., with chemical agents or radiation), and by which clones of cells containing the mutated cyclin E nucleotide sequences may be identified and/or selected. The subject mutant cyclin E nucleotide sequences are useful for modulating or altering the activity of a cyclin E:CDK2 complex in a cell, e.g., in a tumor cell to decrease CDK2 kinase activity and slow cell proliferation, or in a terminally differentiated cell to increase CDK2 kinase and stimulate growth. The subject mutant cyclin E nucleotide sequences may be introduced using vectors such as the illustrative retroviral vectors in Example 9.

Artificial cyclin E polypeptides, organic chemical mimetics, antisense RNA and oligonucleotides, and the like find broad utility as selective inhibitors of cell proliferation triggered by growth factors, mitogens, cytokines, and like agents, without inhibiting ongoing reparative mitotic activity in a tissue. Thus, it will be appreciated that the synthetic polypeptides, mimetics, and antisense embodiments of the invention will preferably exhibit differential inhibitory activities; e.g., when the subject inhibitor is introduced into two cells, one triggered by a cytokine to proliferate, and a second undergoing mitosis, the first cell is inhibited but the second cell is not. The subject synthetic cyclin E polypeptides of the invention only inhibit cells that are transitioning from G1 to S, and not those cells that are already actively undergoing mitosis. Thus, those skilled in the art will recognize that representative examples of utility include inhibiting induction of immune responses; interrupting clonal expansion (i.e., either T or B lymphocyte) of an ongoing immune response; inhibiting growth factor-induced proliferation of tumor cells or metastatic cells that are transitioning from G1 to S; and inhibiting growth factor-induced tissue hypertrophy (e.g., vascular smooth muscle cell proliferation such as in atherosclerotic plaques, mesenchymal hypertrophy of fibroblasts and connective tissue cells such as in rheumatic joints, and the like). The subject selective inhibitors are conveniently recognized, for instance, by their ability: a) to either decrease (or increase) the levels of cyclin E polypeptide or mRNA in a test cell in vitro (i.e., compared to a control cell of the same type); b) to decrease (or increase) the level of cyclin E that can form a complex with CDK2; or c) to decrease (or increase) the binding affinity of cyclin E polypeptides for members of the CDK2 family of cell cycle dependent kinases in mammalian cells. Skilled artisans will recognize that measuring a decreased (or increased) activity of a subject selective inhibitor may be accomplished using asynchronized or synchronized cell cultures; e.g., in synchronized cultures of cells cyclin E levels and activities are examined during the G1 phase of the cell cycle.

Aspects of the invention include recombinant expression vectors such as viral vectors for mammalian cells (e.g., retroviruses similar to that illustrated in Example 9, vaccinia virus, adenoviruses, CMV, and the like), and plasmid or cosmid vectors useful for transfecting and transducing nucleic acid into prokaryotic and eukaryotic cells. Recombinant expression vectors of the invention are constructed for example by operably linking a cyclin E nucleic acid to suitable control sequences. Operably linking is used herein to mean ligating a cyclin E nucleic acid to an expression vector nucleic acid in a manner suitable for transcription and translation of cyclin E, preferably under a predetermined positive (or negative) regulatory control exerted by control sequences in the expression vector (i.e., containing regulatory sequences capable of driving expression, over-expression, and constitutive-expression of the cyclin E gene, e.g., promoter, enhancer, operator sequences, and the like). Selectable markers will generally be included in the expression vector. Representative examples of such selectable markers include enzymes, antigens, drug resistance markers, or markers satisfying the growth requirements of the cell. It will also be appreciated that in certain cells transfection or transduction with cyclin E nucleic acid will provide a selective proliferative/growth advantage that will serve as a type of selectable marker (e.g., in mutants blocked for progression of the cell cycle, such as the representative yeast strains "598-5" or "1238-14C " described below in the Examples). The subject expression vectors are useful for transfecting and transducing cells to produce cyclin E polypeptides, mutant cyclin E polypeptides, and antisense nucleic acids. For instance, aspects of the invention include methods for using the transfected and transduced cells to produce polypeptides that are able to activate a CDC protein kinase and advance the cell cycle at the restriction point from the G1 phase to the S phase. Several methods are available for determining that a polypeptide encoded by a cyclin E nucleic acid is capable of advancing the cell cycle. Representative examples involving yeast cells and mammalian cells are described in the Examples, below.

The invention also provides a cell type that has been transduced or transfected with a cyclin (e.g., cyclin E) expression vector. In one preferred embodiment a cell constitutively over-expressing cyclist E proliferates at a rate faster than its parent cell. Cyclin E-transduced human diploid fibroblasts illustrated in Example 14, below, were 20–50% smaller in length and width than control-transduced or normal cells. Skilled artisans will understand the advantages in gene therapy of small rapidly growing cells, e.g., cells that may be grown in a cost-efficient manner and that may undergo programmed senescence faster than their normal counterparts. It will also be understood that transgenic animals (e.g., experimental and domestic animals) may be constructed of such small rapidly growing cells. Skilled artisans will recognize that the advantages offered by the subject cells include: a) improved growth in tissue culture of terminally differentiated cell types that would normally be difficult or impossible to culture (e.g., stem cells); and b) lessened (or no) dependence on growth factors for cell growth (e.g., for cells that are difficult to propagate in vitro such as muscle or neural cells), allowing more rapid growth of cultures of mammalian cells in low-serum (or serum-free) medium (e.g., in production cultures of cells manufacturing biotherapeutic agents). The disclosure herein identifies the singular significance of a cyclin in determining the progression of the cell cycle at each of several decision points. The term "decision point" is well accepted in the art as meaning a point in the cell cycle where a cell may arrest its growth until such time as an appropriate signal is received to progress the cell cycle. The results presented in Example 14, below, illustrate the significance of cyclin E in activating a latent CDK2 kinase activity at a decision point in the G1 phase of the cell cycle. Several decision points exist during the different phases of the cell cycle. The disclosure herein indicates that a small number of cyclins may be operative in the cell cycle, i.e., one cyclin to advance the cell cycle at each decision point. Thus, over-expression of a relatively small number of cyclins in a cell may be sufficient to render the cell nearly completely independent of exogenous growth factors.

In other embodiments the invention provides immunologic binding partners for cyclin E polypeptides such as polyclonal and monoclonal antibody molecules, and various antigen-binding fragments thereof, capable of specifically binding the cyclin E polypeptide. Such immunologic binding partners may be produced by hybridoma or rDNA expression techniques and find utility in therapeutic, purification, and diagnostic applications. Therapeutic applications include binding partners that inhibit binding of a cyclin E to its CDC protein kinase; binding partners that modulate CDC protein kinase; and binding partners that alter regulatory control of cyclin E in a cell. Representative examples of purification applications include immunochemical methods and immunoaffinity chromatography. Representative examples of diagnostic applications include enzyme-linked and radioisotopic immunoassays, immunofluorescence, fluorescence immunoassay, time-resolved fluorescence immunoassay and the like. The specific binding partners used in these assays may be capable of distinguishing between free cyclin E polypeptide and cyclin E bound in complex with CDC protein kinases. Those skilled in the art will recognize that "neo" (new) antigens are acquired by conformationally altered polypeptides, and will further recognize that the binding between cyclin E and a CDC protein kinase induces such a conformational alteration in both polypeptides. The cyclin E-specific binding partners find general utility in diagnostic assays for detecting and quantitating levels (e.g., protein or antigen) and functional activities (e.g., phosphorylase kinase activation) of free cyclin E (or complex-associated cyclin E) in a cell such as a tumor cell. The subject diagnostic assays include assays for: a) detecting the absolute levels and activities of cyclin E in nonsynchronized cell populations (e.g., in tumor biopsy specimens); b) comparing the levels and activities of cyclin E in synchronized cell populations at different phases of the cell cycle (e.g., cell populations synchronized by thymidine-block); and c) assays for determining the levels and activities of cyclin E in biological fluids (i.e., blood, serum, plasma, mucus secretions, CNS fluid, cell extracts, and the like). The absolute levels and activities of cyclin E expressed in malignant biological fluids (e.g., tumor cell extracts, serum from cancer patients, and the like), as well as the levels and activities expressed in cell extracts prepared at different stages in the cell cycle, may provide information on the rate of cell growth. In this regard the assayed levels and activities of cyclin E may serve as diagnostic markers for:

a) staging tumors, since differentiated cells grow more slowly than transformed; express lower levels of cyclin E protein and activity than transformed cells; and (in contrast to transformed) differentiated cells express cyclin E only during G1 phase of the cell cycle;

b) determining prognosis, i.e., predicting patient survivability and time to recurrence of tumor, because rapidly growing malignant cells capable of metastasis may generally grow more rapidly than differentiated cells; exponentially growing cells may express higher absolute levels (or activities) of cyclin E, or alternatively, the higher levels (or activities) of cyclin E may be present during a particular phase of the cell cycle, e.g., during S, G1 or G2 phase; and/or c) predicting therapeutic success, i.e., of a particular therapeutic regimen, because more slowly growing cells may express lower levels (or activities) of cyclin E (i.e., than rapidly growing metastatic cells) and also be more responsive to less drastic and more prolonged therapeutic regimens.

The subject assays for determining the level (or activities) of cyclin E in cells may also indicate the responsiveness of a patient's tumor to a particular therapeutic agent exerting its affect on cells during the G1 phase of the cell cycle. Those skilled in the art will recognize that the potentially useful assays may provide results that are potentially useful to a physician in deciding how to stage a tumor, how to select an appropriate therapeutic regimen, how to evaluate the success of therapy, and how to evaluate patient risk or survivability.

In other embodiments, the invention provides diagnostic assays for measuring the absolute levels (or functional activities) of cyclin E:CDK 2 polypeptide complexes in asynchronous cells, and the levels (or activities) of the cyclin E:CDK 2 complexes at different stages in the cell cycle. In nontransformed cells the peak abundance of the cyclin E:CDK 2 complexes occurs late in the G1 phase of the cell cycle, e.g., with levels 4-fold to 6-fold higher than in other phases of the cell cycle. In transformed cells constitutive over-expression of cyclin E and/or CDK 2 may lead to differences in the levels of the cyclin E:CDK 2 complexes that are detectably different during the G1, G2, M, and S phase of the cell cycle. The subject assays that determine the levels of cyclin E/CDK 2 complexes in cells may be useful in assessing malignant cells from patients, e.g., as described above.

In other embodiments the invention provides diagnostic assays for determining chromosomal rearrangement of cyclin E and CDK2 genes in a cell. The chromosomal location of cyclin E and CDK2 genes is conveniently determined in chromosomal smears by in situ hybridization with oligonucleotide probes or cDNA and the like. Translocation of a cyclin E gene or CDK2 gene, i.e., from a chromosomal location found in a normal cell to a location found in a transformed cell, may contribute to a phenotype of uncontrolled cell growth by removing normal transcription regulatory control of either gene expression of a cyclin, e.g., cyclin E, or a CDC kinase, e.g., CDK2. The findings disclosed herein indicate heretofor unrecognized common junction points where second messenger signals from multiple growth factors converge at a small number of different cyclin:CDC kinase complexes. The outcome of the molecular interaction of the second messengers with the cyclin:CDC kinase complexes determines whether the cell progresses the cell cycle. Thus, rearrangement of a cyclin gene in a cell may have dramatic results. In the case where the rearrangement induces over-expression the cell may acquire a malignant (i.e., uncontrolled) growth phenotype, and in the case where the rearrangement induces under-expression the cell may undergo premature senescence. Screening cellular samples from individuals for the potential of cyclin E or CDK2 chromosomal rearrangement may indicate a relative risk factor for the possibility of developing cancer. In the event that such rearrangements are detected, restoring normal control of a cyclin gene (e.g., cyclin E) or a CDC kinase gene (e.g., CDK2) in a translocated chromosomal location may reverse the malignant phenotype of a transformed cell. For example, the cyclin E gene (of CDK2 gene) and its regulatory elements may serve as targets for gene therapy vectors designed to inactivate the rearranged gene, e.g., using in situ-directed recombination/ mutagenesis or targeted integration to disrupt the translocated gene.

The invention also provides transgenic strains of yeast cells that are engineered to contain a genome lacking in cln1, cln2, and cln3 genes required for cell cycle progression but having an episomal nucleic acid capable of encoding CLN3. A representative embodiment is yeast strain "589-5", which is useful to identify mammalian cyclin genes. Strain "589-5" has been deposited with the American Type Culture Collection, Rockville, Md., under accession No. 74098. When cyclin E nucleic acid is introduced into the transgenic yeast cells of this strain, the cells advance through the cell cycle from START into S phase. While others have shown previously that somewhat similar transgenic yeast constructions are useful for identifying and cloning yeast cdc genes, the subject strains are useful for identifying and cloning mammalian cyclin E cDNA, and also for identifying and cloning mammalian cdc protein kinase cDNAs.

The invention also provides other transgenic strains of yeast cell, having a cdc28-13 gene, an endogenous G1 CLN (e.g., CLN3) under control of a conditional promoter (e.g., GAL), a mitotic CLB cyclin (e.g., CBC), and a cyclin E gene, such as the representative yeast strain "1238-14C-cyclin E". In this case the conditional promoter drives expression of the G1 cyclin in the presence of a factor ("the condition") required for metabolism or growth. The G1 cyclin, in turn, binds and activates the cell division kinase encoded by the cdc28-13 gene, and activation of the CDK allows the cells to be grown and passaged. Strain "1238-14C-cyclin" has been deposited with the American Type Culture Collection, Rockville, Md., under accession No. 74099. The cell cycle is blocked in these cells until a cdc protein kinase nucleic acid is introduced. Thus, this strain of transgenic cells is useful for identifying and cloning cdc protein kinases that associate with a cyclin E and advance the cell cycle from G1 into S phase in a eukaryotic host cell.

The invention also provides methods for cloning regulatory agents such as polypeptides that bind to cyclin E:CDC protein kinase complexes and inhibit or promote the activity of the complex, or that change the half-life of the complex, and the like. Nucleic acids encoding such regulatory agents are identified by introducing a candidate nucleic acid molecule into a transgenic strain of yeast cell, or a mammalian cell, in which advance of the cell from G1 into S phase is dependent upon the activity of a cyclin E:CDC protein kinase. A representative example of a transgenic yeast strain useful in this manner is provided by strain 598-5 transfected or transduced with a cyclin E gene, such as strain HU4 described in greater detail in the Examples below. Nucleic acids encoding regulatory agents are recognized by their ability to inhibit progression of the cell from G1 into S. Thus, in the case of the described transgenic yeast strain, replicative screening techniques may be used for identifying clones of cells that fail to advance the cell cycle at START after they have been transfected or transduced with any candidate cDNA, e.g., mammalian, insect, avian, reptilian, amphibian, etc.

EXAMPLES

The data set forth below show that cyclin E substituted for the *S. cerevisae* CLN genes and interacted with CDC28 to perform START. At least two different members of the human CDC2 gene family could interact with cyclin E to regulate START in budding yeast, CDC2-HS and CDK2-HS. We have also shown that the cyclin E protein bound and activated the p34 CDC2 protein in extracts from human lymphoid G1 cells and that cyclin E was associated with an H1 kinase activity in HeLa cells. Others found that the cyclin E mRNA was specifically present during the late G1 phase of the HeLa cell cycle (Lew et al., 1991). Taken together these results argue that cyclin E may function as a regulator of the p34 CDC2 kinase at the G1 to S transition in the human cell cycle.

The interpretation of our result that cyclin E rescued the triple cln deletion was complicated by the fact that human cyclin B, which is a mitotic cyclin, also substituted for the yeast CLN genes. Regardless of the mechanism by which cyclin B functioned as a CLN protein, the fact that it played this role implied that our complementation assay did not specifically identify CLN-type cyclins. Therefore, a more complete understanding of the function of cyclin E must await analyses of the abundance of cyclin E protein and its association with CDC2, or CDC2-related proteins, during the cell cycle of normal human cells.

In yeast, and probably in most organisms, the CDC2 protein functions at least twice during the cell cycle: at G1/S and again at G2/M. At each point the CDC2 protein associates with a unique type of cyclin: the B-type cyclins at G2/M and the CLNs (at least in budding yeast) at G1/S. Therefore, it had been expected that the unique cyclin-CDC2 complex which assembled at each control point would impart the specificity required for the CDC2 kinase to activate either S phase or mitotic events. For example, the substrate specificity or subcellular localization of the CDC2 kinase would be determined by its particular cyclin partner. The ability of human cyclin B to substitute for the CLN proteins appears, on the surface, to contradict this simple hypothesis. As an alternative it is possible that the specificity of p34 CDC2 action at different points in the cell cycle might be determined, at least in part, by the CDC2 protein itself. This could be due to cell cycle-specific modification of the CDC2 protein (Simanis & Nurse, 1986; Lee et al., 1988; Gould & Nurse, 1989; Krek & Nigg, 1991) or, in higher eukaryotes, to the activation of different members of the CDC2 gene family at different points in the cell cycle (Paris et al., 1991; Pines & Hunter, 1990). Our observation that at least two different members of the CDC2 gene family can perform START in yeast is consistent with this idea. In this model periodic accumulation and destruction of the cyclin proteins would determine the timing of p34 kinase activation but not its specificity. A model similar to this has been proposed previously based upon the phenotypes of certain cdc2 mutants in S. pombe (Broek et al., 1991). An alternative is that the particular substrates necessary for CDC2 or CDC28 to induce the S or M state become accessible in a cell cycle-dependent manner. We point out, however, that the design of our experiments may not have permitted all the normal controls on cyclin specificity to be observed. For example, expression of human cyclin B from the strong ADH promoter might have overwhelmed certain regulatory processes that usually limit cyclin B-CDC28 activity to the G2/M transition.

Human cyclin E is more closely related to human cyclins A and B than to the budding yeast CLN proteins. Within the cyclin box the level of identity to CLN1 is 21% and to CLN3, 17%. This compares to 49% identity to human cyclin A and 44% to human cyclin B. Outside the cyclin box region cyclin E shows no extensive homology to either the human cyclins or yeast CLN proteins. On this basis cyclin E does not appear to be a direct homolog of the yeast CLN genes. This comparison must be made with caution, however, since the precise regions within the various cyclins that determine their functional differences have not been identified. In addition, the similarity among the human cyclins may reflect, to some extent, their co-evolution with common targets such as the human CDC2 protein.

Two other features of the cyclin E sequence should be noted. Our clone of cyclin E lacks an N-terminal sequence found in both cyclin A and B, which is thought to be a recognition motif for the ubiquitination enzyme that mediates their destruction in mitosis (Glotzer et al., 1991). Furthermore, cyclin E contains a C-terminal extension when compared to cyclins A and B. This C-terminal region is flanked by basic residues and is rich in P (Pro), E (Glu), S (Ser), and T (Thr) residues. Such "PEST" regions have been implicated in controlling protein turnover (Rogers et al., 1986). In fact, the stability of the yeast CLN proteins may be determined by their C-terminal domains which are also rich in P, E, S, and T residues (Nash et al., 1988; Cross, 1990; Hadwiger et al., 1989). These observations suggest that the stability of cyclin E during the cell cycle might be controlled differently than the mitotic cyclins.

In higher eukaryotes the role of the CDC2 protein during progression through the G1 phase of the cell cycle is not well understood. A number of independent observations suggest that the CDC2 protein has an essential function during this part of the cell cycle. Depletion of the CDC2 protein in vivo in human cells, using antisense oligonucleotides (Furakawa et al., 1990), or in vitro in Xenopus extracts, by immunoprecipitation (Blow & Nurse, 1990), can block the start of DNA synthesis. Addition of cyclin-CDC2 complexes from human S phase cells to extracts from G1 cells can activate DNA synthesis (D'Urso et al., 1990). However, a thermolabile mutation of the murine CDC2 gene blocks entry into mitosis but not S phase at the nonpermissive temperature (Th'ng et al., 1990). Also, microinjection of antibodies against the yeast CDC2 protein into human cells blocks the G2/M but not the G1/S transition (Riabowol et al., 1989). Our observation that at least two different members of the CDC2 gene family can regulate the G1/S transition in S. cerevisae may help clarify these apparently contradictory results. One of these, the human CDK2 gene, might preferentially work at G1/S as opposed to G2/M. Therefore, in higher eukaryotes, in contrast to the situation in yeast, multiple members of the CDC2 gene family may participate in G1/S regulation. Under some circumstances their roles might be redundant, while in other situations they may all be essential.

Activation of the CDC2 kinase during the G1 to S interval is likely to require its association with a cyclin. In S. cerevisae accumulation of a CLN-type cyclin is the rate-limiting step for transit through START (Nash et al., 1988; Cross, 1988; Hadwiger et al., 1989). In human cells activation of the p34 kinase at the start of S phase correlates with its assembly into a higher molecular weight complex (D'Urso et al., 1990; Marraccino et al., unpublished data), implying that association of p34 with a cyclin protein regulates its activity during this part of the cell cycle. We have also found that addition of purified recombinant clam cyclin A to a human G1 cell extract was sufficient to activate SV40 DNA replication, suggesting that accumulation of a cyclin is the limiting step for activation of the p34 kinase at the start of S phase.

At least four different human cyclins have been suggested to play roles during the G1 or S phases of the cell cycle. These include cyclins A (Giordano et al., 1989; Wang et al., 1990), C (Lew et al., 1991), D (or pradI; Motokura et al., 1991; Xiong et al., 1991; Matsushimi et al., 1991), and E (this disclosure; Lew et al., 1991). In yeast, human cyclin E can associate with either CDC2-HS or CDK2-HS to perform START. In vitro cyclin E can bind and activate CDC2-HS, but its ability to activate CDK2 from G1 cells has not yet been tested. Human cyclin A has also been found to associate with two different members of the CDC2 gene family, CDC2-HS and a 33 kDa protein which may be CDK2 (Giordano et al., 1989; Pines & Hunter, 1990; R. Marraccino & J. R., unpublished observations). In contrast, the mitotic cyclin B has been found in association only with p34 CDC2 (see Hunt, 1989).

Multiple cyclins and CDC2-like proteins may be required to convey the diverse array of intracellular and extracellular signals that contribute to G1 regulation. Different members of the CDC2 protein family may preferentially interact with particular cyclins (Pines & Hunter, 1990). Also, each cyclin-CDC2 complex may perform only a subset of the events necessary for START to occur. Finally, it is possible that the CDC2 family of proteins may function at more than one point during G1. The START decision in yeast is the only clearly defined execution point for CDC28 during the G1 phase of the cell cycle. START bears certain similarities to the restriction point in the cell cycle of higher eukaryotes; however, the restriction point can occur hours before the start of S phase. Our in vitro replication experiments indicate that the CDC2 kinase may directly activate DNA synthesis (D'Urso et al., 1990). Therefore, CDC2, or related proteins, may function twice during G1, first at the point of commitment to cell proliferation and again at the onset of DNA synthesis. Each control point may require a unique set of cyclin proteins; for example the CLN-type cyclins may function at the restriction point and other cyclins, such as cyclin E, could act at the G1/S transition.

Example 1

Complementation of a yeast strain lacking CLN1, -2 and -3 with a human cDNA library.

Figure 1B:
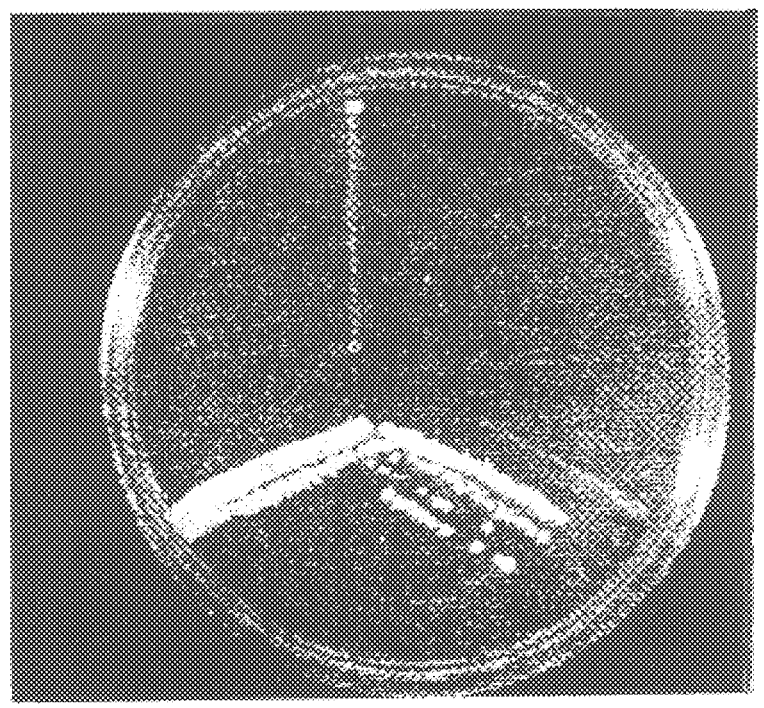

Our initial goal was to identify human cDNAs encoding proteins that could substitute for the yeast CLN proteins. A yeast strain, 589-5, was constructed in which all three chromosomal CLN genes were deleted and which contained the CLN3 gene under the control of the GAL1 promoter on an episome. As CLN protein is required for passage through START, this strain will grow on galactose, where the GAL1 promoter is induced; when this strain is grown on glucose the GAL1 promoter is repressed, no CLN3 protein is made, and the cells arrest at START (Cross, 1990). A cDNA library (a gift of J. Colicelli and M. Wigler), using mRNA prepared from the human glioblastoma cell line U118, was constructed in a S. cerevisae vector containing the constitutive yeast ADH promoter for expression of the human cDNAs (Colicelli et al., 1989). The library was transfected into strain 589-5, and $10^5$ independent transformants were screened, by replica plating, for their ability to grow on glucose. One transformant, HU4, was isolated whose growth on glucose was dependent upon expression of a human cDNA (FIG. 1). For further experimental details, see the appended Materials and Methods.

Example 2

HU4 encodes a new member of the cyclin protein family

The DNA sequence of the 1.7 kb HU4 cDNA is shown in FIG. 2, and its homology, at the protein level, to human cyclins A and B is illustrated in FIG. 3. The DNA sequence predicts a protein with 395 amino acids and a molecular weight of 45,120 daltons. Ii vitro transcription/translation of the HU4 cDNA yields a protein with the predicted molecular weight (see FIG. 8). All known cyclins have a highly conserved central domain of approximately 87 amino acids. HU4 is 49% identical to human cyclin A and 44% identical to human cyclin B within this domain. On this basis we placed the HU4 protein within the cyclin family. N-terminal to this conserved region the homology to cyclin A falls to 5% identity, and 4% identity to cyclin B. C-terminal to this domain the identity to cyclin A is 14%, and the identity to cyclin B is 10%. This low level of homology both N- and C-terminal to the central conserved domain suggests that HU4 represents a new class of cyclin proteins, and we have designated this class as cyclin E. We cannot be certain that our cyclin E cDNA clone contains the entire cyclin E protein coding sequence, as the open reading frame extends to the 5' end of the sequenced cDNA. However, a cyclin E cDNA clone obtained from a MANCA cell library showed a 5' end identical to the one described here.

Example 3

Human cyclin B complements the triple cln deletion

We compared the ability of human cyclin A, B, and E cDNAs to complement the triple cln deletion in strain 589-5. Full-length cDNA clones encoding human cyclins A (Pines & Hunter, 1990) and B 1 (Pines & Hunter, 1989) were cloned into the ADH expression vector used in construction of the library described above. The various cyclin E expression plasmids were transfected into yeast by selecting for leucine prototrophy. The transformants were picked, and the ability of the human cyclin to complement the absence of the CLN proteins tested by growth on glucose. No leucine prototrophs were obtained using the cyclin A vector, suggesting that expression of full-length human cyclin A in S. cerevisae was lethal. FIG. 4 depicts the relative plating efficiency of 589-5 on glucose versus galactose when containing either cyclin B or E expression plasmids. Surprisingly the mitotic cyclin B complemented the absence of the CLN proteins. This experiment demonstrated that complementation of CLN function was not restricted to CLN type cyclins.

Example 4

Interaction between cyclin E and CDC28

We compared the ability of cyclin E to rescue the triple cln deletion in isogenic strains containing either the CDC28 or the cdc28-13 allele at the permissive temperature of 30° C. FIG. 4 shows that cyclin E substituted for the CLN proteins significantly less well in the cdc28-13 background. This genetic interaction between the cyclin E and CDC28 genes suggested that the cyclin E protein performed its function by interacting with the CDC28 protein. Cyclin B was about as effective in cdc28-13 versus CDC28 strains, suggesting that cyclin B might interact with CDC28 differently than cyclin E.

Example 5

Human cyclin E and human CDC2 can perform START in S. cerevisae

Strains containing cdc28-13 and the endogenous G1 (CLN) and mitotic (CLB) cyclins are viable at 30° C. Therefore, the cdc28-13 protein must be capable of functional interactions with both types of cyclins. As described above, a cdc28-13 strain that contained cyclin E in place of the CLN genes did not grow at 30° C. We speculated that this strain was defective specifically for the START function of the CDC28 protein and not for its G2/M role, presumably because the cdc28-13 mutation diminished its ability to interact productively with cyclin E. These properties of the cyclin E-cdc28-13 strain are shown in FIG. 5. We used this strain as a host to screen for human genes that could interact with cyclin E to perform START. Unlike screens requiring human genes to completely substitute for CDC28, this screen may not require that the human genes function at G2/M. We transfected this strain with the human cDNA expression library described above, and $10^5$ independent colonies were tested for their ability to grow on glucose. We identified five yeast clones whose growth depended upon expression of both the human cDNAs (cyclin E and the new one) (FIG. 6). The human cDNA within each of these clones was restriction mapped (data not shown). Four of these (S2-6a2, S2-103, S2-112, S2-227) contained the CDC2-HS gene (Lee & Nurse, 1987). The S. pombe cdc$^+$ gene also performed START together with human cyclin E in this strain (F. C. & A. Tinkelenberg, unpublished observations). These results provide further evidence that the cyclin E protein controls START through its interaction with the CDC2 or CDC28 protein. The fact that the S. cerevisae CDC28 and CLN genes can be replaced simultaneously by human proteins also emphasizes the extent to which the basic cell cycle machinery has been conserved in evolution.

Example 6

Transit through START in yeast containing human cyclin E and human or Xenopus CDK2, a member of the CDC2 gene family The restriction map of the fifth clone, S2-124, did not match that of CD2-HS. Recently, the human homolog of the Xenopus CDK2 gene (formerly called Eg-1; Paris et al., 1991) was cloned (S. Elledge, personal communication), and the restriction map of S2-124 matched that of CDK2-HS. In addition we found that the Xenopus CDK2 gene also substituted for CDC28 and performed START in conjunction with cyclin E. Therefore, humans and Xenopus contain at least two members of the CDC2 gene family that can control the G1/S transition in yeast. In order to test whether the human CDC2 gene, or the CDC2 homolog CDK2, fully complemented cdc28-13, we grew these transformants at 38° C. (FIG. 5). At 38° C. cdc28-13 is defective compared to wild-type CDC28 for both G1/S and G2/M (Reed & Wittenberg, 1990). As expected (Wittenberg & Reed, 1989) cells containing the CDC2-HS gene grew equally well at 30° or 38° C., showing that the CDC2-HS gene was able to complement both the G1/S and G2/M functions of cdc28-13. Curiously, at 38° C. the strains containing the human or Xenopus CDK2 gene and human cyclin E failed to grow. Therefore, under these experimental conditions, the human or Xenopus CDK2 genes only partially substituted for CDC28. In addition, initial attempts to complement a GAL-CDC28 strain with CDK2-HS (on glucose) showed that complementation was extremely poor compared with complementation by CDC2-HS. The failure of CDK2-HS to fully complement either cdc28-13 or GAL-CDC28 is consistent with a previous report showing that the Xenopus CDK2 gene did not complement either cdc28 or cdc2 temperature-sensitive alleles (Paris et al., 1991). The explanation for the partial rescue of cdc28-13 by CDK2 is unclear, but one possibility is that the CDK2 protein can complement effectively the G1/S but not the G2/M function of CDC28. To address this issue definitively, it would be essential to determine the cell cycle arrest points of the strains described above. This has not been possible because the instability of the plasmids resulted in only a minority of the cells containing all three plasmids even on selective medium (data not shown).

Example 7

Activation of human p34 CDC2 by cyclin E

Mixing cyclin E protein with G1 cell extracts demonstrated directly that cyclin E could bind the human CDC2 protein in vitro and that this association led to activation of the CDC2 kinase. We have shown previously that human G1 cells contain no active p34 CDC2 kinase; all the P34 protein present in the cell is monomeric, unassociated with any cyclin (Draetta & Beach, 1988; D'Urso et al., 1990). G1 extracts were prepared from MANCA cells, a human Burkitt's lymphoma cell line. We confirmed that these G1 extracts contained no detectable CDC2 kinase. The extracts were mixed with a vast excess of p13-Sepharose relative to CDC2 protein, conditions that ensure quantitative binding of CDC2 protein to p13-Sepharose. No histone H1 kinase activity could be detected specifically associated with the p13-Sepharose beads (see FIG. 7B). Also, these G1 extracts were inactive in a kinase assay using a specific peptide substrate of the CDC2 kinase (Marshak et al., 1991).

Figures 7A, 7C:
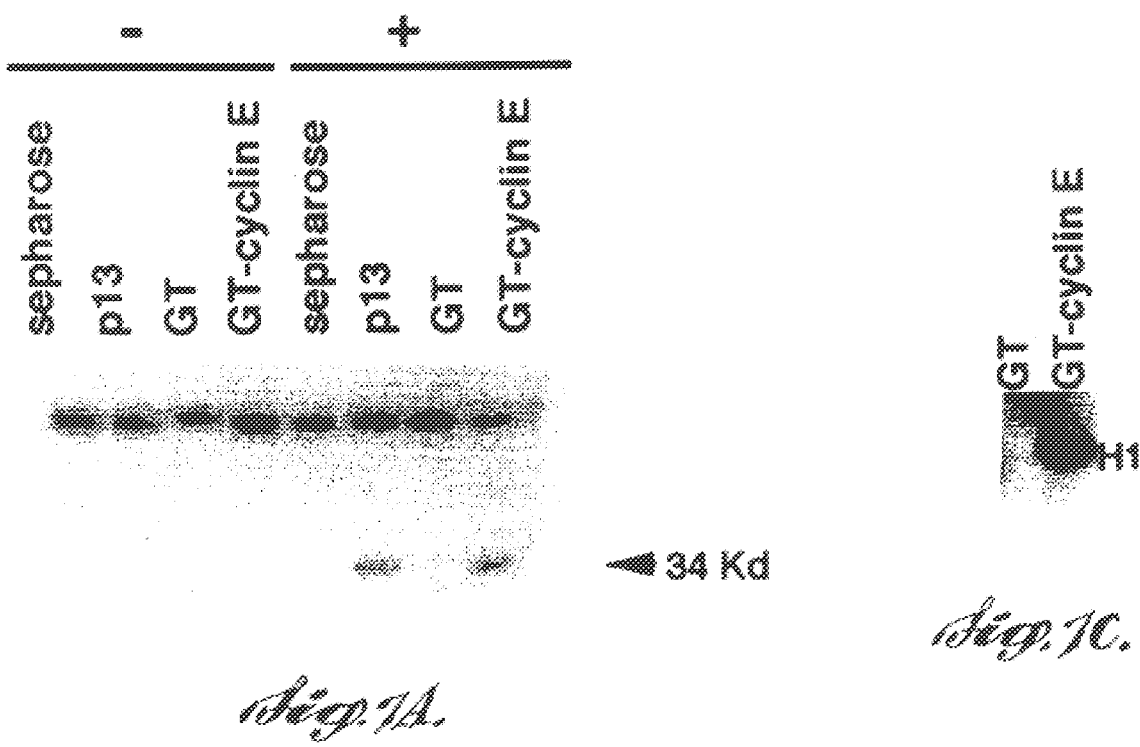
FIG. 7 shows cyclin E can bind and activate the p34 cdc2 kinase in extracts from human G1 cells: Extracts from newborn MANCA human G1 cells were mixed with GT-cyclin E-Sepharose beads, GT-Sepharose, p13-Sepharose, or blank Sepharose beads. In panel A, the bound proteins were immunoblotted with anti-peptide antiserum against the carboxy terminus of human CDC2. In lanes labeled "+" the Sepharose beads had been incubated with the human G1 extract. In lanes labeled "−" mock incubations with buffer were performed. The arrow indicates the bound 34 kDa protein that reacts with the C-terminal antibodies. In panel B, the beads were assayed for histone H1 kinase activity. Arrows indicate the mobility of histone H1 and GT-cyclin E fusion protein markers. In the lane labeled "cycE-IP" the proteins associated with the GT-cyclin E-Sepharose beads were released with free glutathione and immunoprecipitated with a cyclin E antiserum. In panel C, the proteins released from either the GT-Sepharose or GT-cyclin E-Sepharose by free glutathione were immunoprecipitated with an affinity-purified C-terminus-specific p34 CDC2 anti-peptide antiserum. The immunoprecipitates were tested for H1 kinase activity.

To study the interaction between cyclin E and CDC2, cyclin E was expressed in E. coli as a glutathione transferase fusion protein (GT-cyclin E) and purified by affinity chromatography on glutathione-Sepharose. We incubated the G1 cell extract with GT-cyclin E-Sepharose, GT-Sepharose, p13-Sepharose, and blank Sepharose beads. GT-cyclin E-Sepharose and p13-Sepharose bound equivalent amounts of p34 CDC2 protein, as detected by immunoblotting using a C-terminus-specific p34 CDC2 antiserum (FIG. 7A). We detected no binding of p34 CDC2 to GT-Sepharose or blank Sepharose.

Figure 7B:
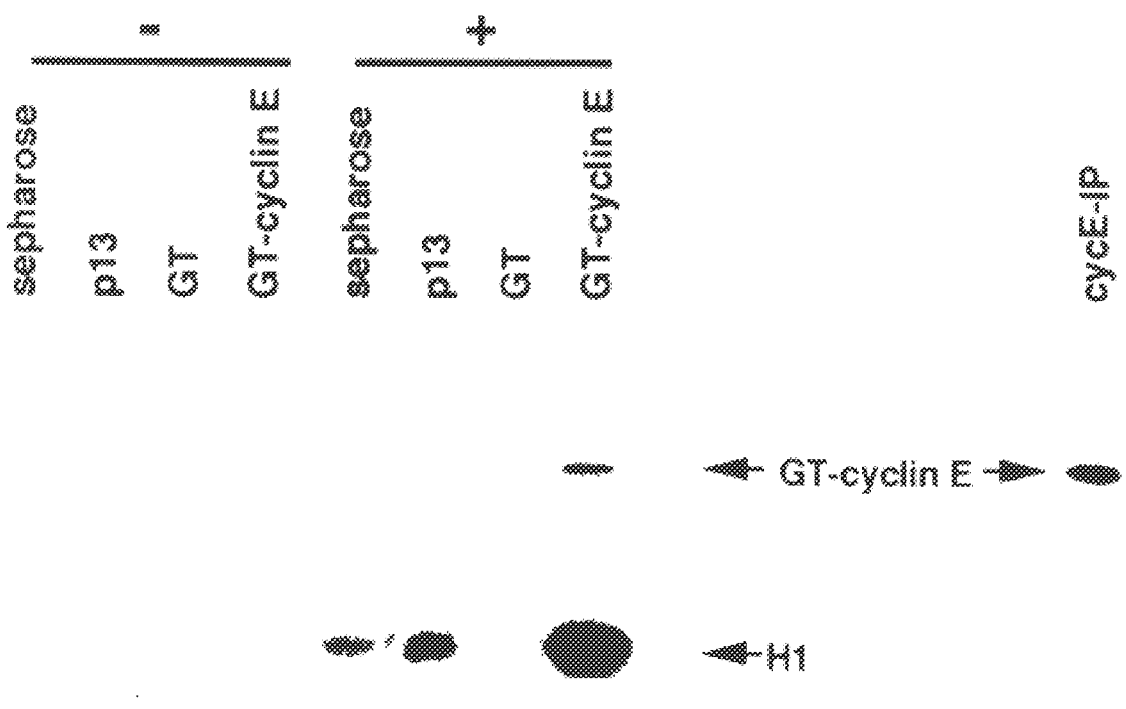

After incubation in the G1 extract the Sepharose beads were assayed for histone H1 kinase activity. Only the GT-cyclin E-Sepharose beads contained histone H1 kinase activity, even though the p13-Sepharose and GT-cyclin E-Sepharose beads bound equal amounts of p34 CDC2 protein (FIG. 7B). We also observed that the cyclin E fusion protein was phosphorylated by the bound kinase. A protein precisely comigrating with the cyclin E fusion protein was phosphorylated during the H1 kinase reaction, and this phosphoprotein was immunoprecipitated by a cyclin E antiserum (FIG. 7B). Cleavage of the phosphorylated GT-cyclin E fusion protein with thrombin showed that the cyclin E portion of the fusion protein was phosphorylated (data not shown). Phosphorylation of the GT-cyclin E fusion protein was probably due to the bound CDC2 kinase (see below), since autophosphorylation of the cyclin subunit is characteristic of cyclin-CDC2 complexes (Draetta & Beach, 1988; Pines & Hunter, 1989).

The experiments described above did not demonstrate directly that the GT-cyclin E-associated kinase was the p34 CDC2 kinase. To test this, we released the GT-cyclin E-associated proteins from the Sepharose beads by incubation with free glutathione. The released p34 CDC2 protein was immunoprecipitated with a C-terminus-specific p34 CDC2 antiserum and shown to have histone H1 kinase activity (FIG. 7C). As a control we showed that no kinase was immunoprecipitated from the protein released from the GT-Sepharose beads (FIG. 7C). We do not know what fraction of the GT-cyclin E-bound kinase could be immunoprecipitated with the p34 CDC2 antiserum and therefore cannot rule out that other kinases (such as CDK2) contributed to the GT-cyclin E-bound kinase activity.

Our results show that cyclin E bound the p34 CDC2 kinase and support the idea that it was activated by cyclin E. The fact that no CDC2 kinase was detected in the initial G1 extract suggests that association of the CDC2 protein with the GT-cyclin E-Sepharose led to activation of previously inactive protein. Since these experiments were done in crude cell extracts, they could not address whether the association of cyclin E with CDC2 protein was sufficient for activation of the CDC2 kinase. Additional modifications of either the CDC2 or cyclin protein may be necessary steps in the activation pathway.

Figure 8A:
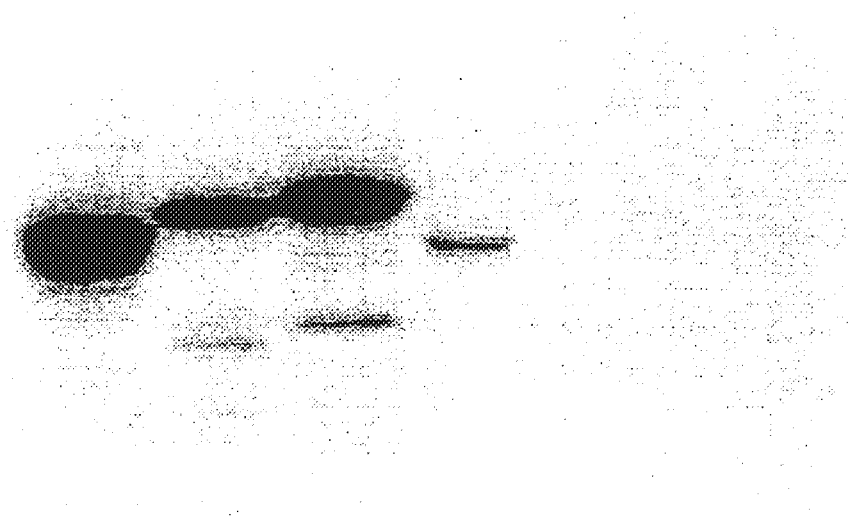
FIG. 8 shows immunoprecipitation of an H1 kinase activity from HeLa cells using anti-cyclin E antibodies: In panel A, an antiserum raised in rabbits against the GT-cyclin E fusion protein was used to immunoprecipitate in vitro translated human cyclins E, A, and B. Lanes 1–3: in vitro translation products of human cyclins E, A, and B respectively. Lanes 4–6: the immunoprecipitates using the cyclin E antiserum of human cyclins E, A, and B respectively. In panel B, extracts from exponentially growing HeLa cells were immunoprecipitated with normal rabbit serum, anti-cyclin E serum, and anti-cyclin A serum. The immunoprecipitates were tested for H1 kinase activity. Note the autophosphorylation of a 45 kDa protein within the cyclin E immunoprecipitates. This protein comigrates with cyclin E protein produced by in vitro transcription/translation of the cyclin E cDNA.
Figure 8B:
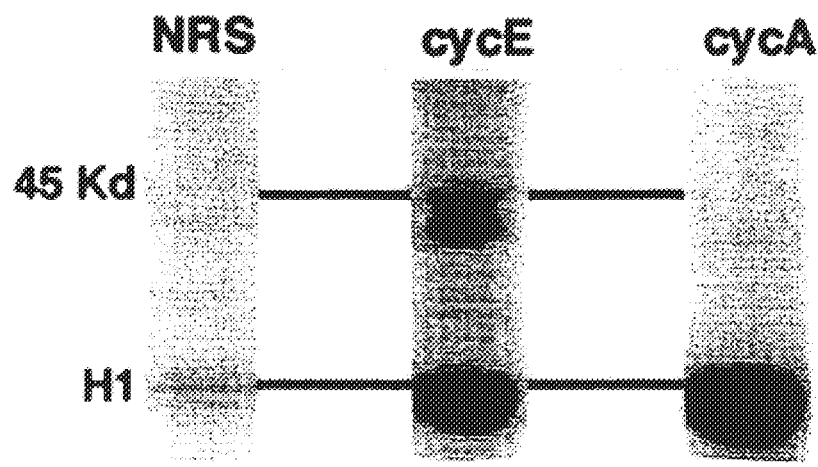

Antibodies were raised in rabbits against the GT-cyclin E fusion protein. These antibodies specifically recognized cyclin E, as they immunoprecipitated in vitro translated cyclin E, but not human cyclin A or B (FIG. 8A). This antiserum immunoprecipitated an H1 kinase activity from HeLa cells (FIG. 8B). This suggested that cyclin E associated with a kinase in vivo, although we do not know which members of the CDC2 family were present in these complexes.

Example 8

Figure 9A:
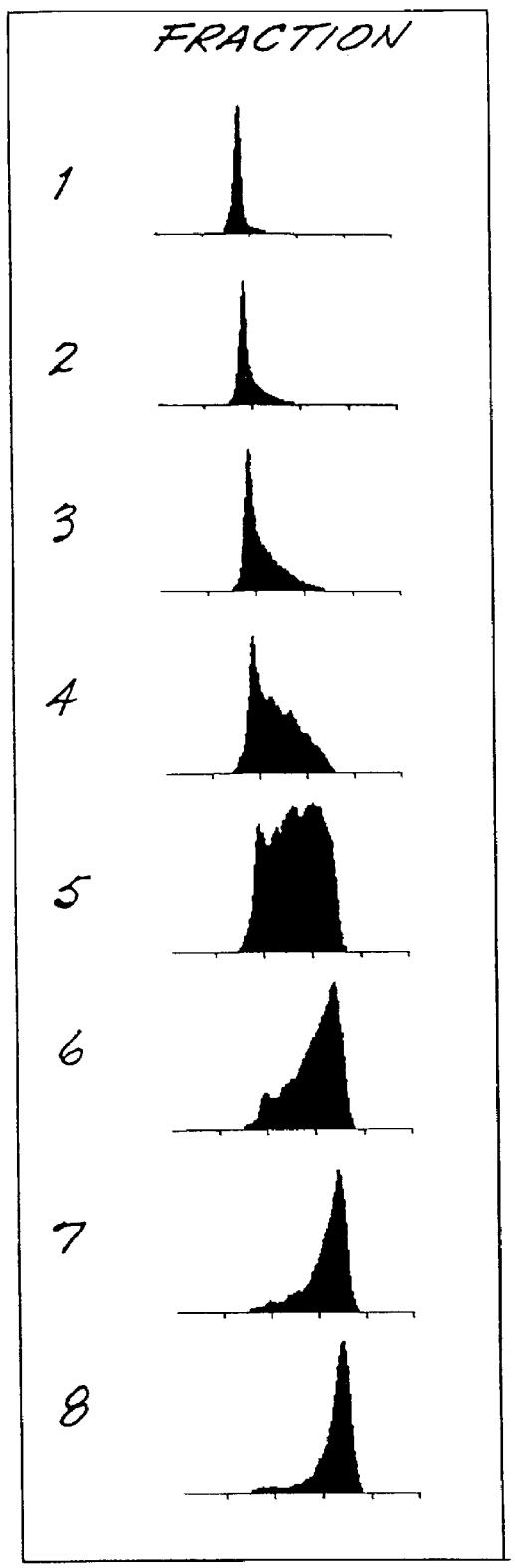
Figure 9B:
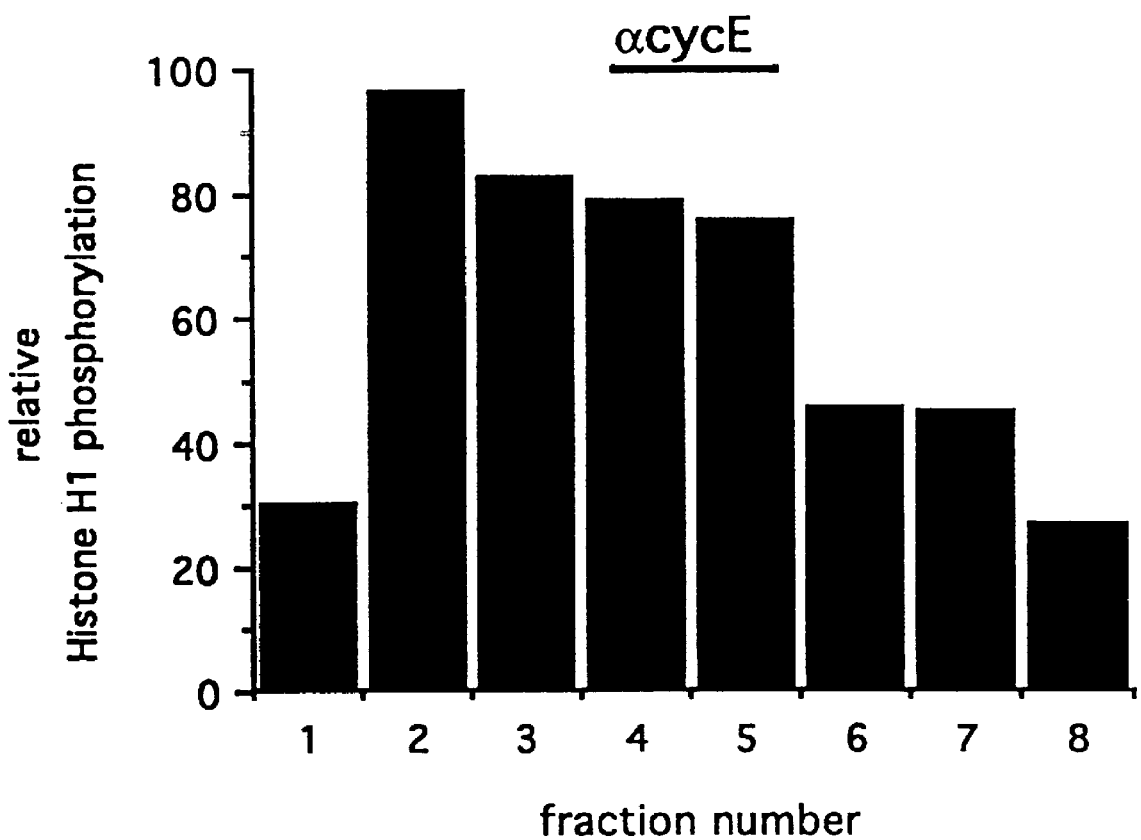

Cell cycle dependent activation of cyclin E and cyclin A-associated protein kinases The previous Examples show that immunoprecipitates of cyclin E from exponentially growing MANCA cells (a human B cell line) contain a cell division kinase. Cyclin E-associated kinase activity during the cell cycle was investigated using centrifugal elutriation to separate exponentially growing MANCA cells into 8 fractions. Centrifugal elutriation physically separates cells into different cell cycle fractions thereby avoiding potential artifacts known to be associated with induced synchronization procedures. We determined the position of an elutriated fraction by measuring the nuclear DNA content by flow cytometric analysis of propidium iodide stained nuclei (FIG. 9A). Cellular extracts from each of the eight different cell cycle fractions were immunoprecipitated using an anti-cyclin E polyclonal antiserum. Pre-immune serum ($\alpha$PI) from the same animal was used as a negative control. For each fraction, the kinase activity in the control immunoprecipitates was subtracted from the activity observed in the specific anti-cyclin E immunoprecipitates. The data, presented in FIG. 9B, show the level of expression of cyclin E-kinase complexes in the elutriated fractions of cells (FIG. 9A) as determined by measuring the level of histone H1 phosphorylation catalyzed by cyclin E-associated H1 kinase activity. Equal numbers of cells from each fraction were lysed, and cyclin E in the lysates was immunoprecipitated with affinity purified anti-cyclin E antibodies ($\alpha$cycE). The results, quantitated by phosphor-imaging, indicate that cyclin E-associated kinase activity was cell-cycle-dependent and, in three experiments, fluctuated during the cell cycle by between 4- and 8-fold. The peak in cyclin E-associated kinase activity corresponded to elutriated fractions of cells having the greatest number of cells in late G1 and early S phase. In some experiments, we also observed a smaller second peak of cyclin E-associated kinase activity in the G2/M fraction of elutriated cells (data not shown).

Figure 9C:
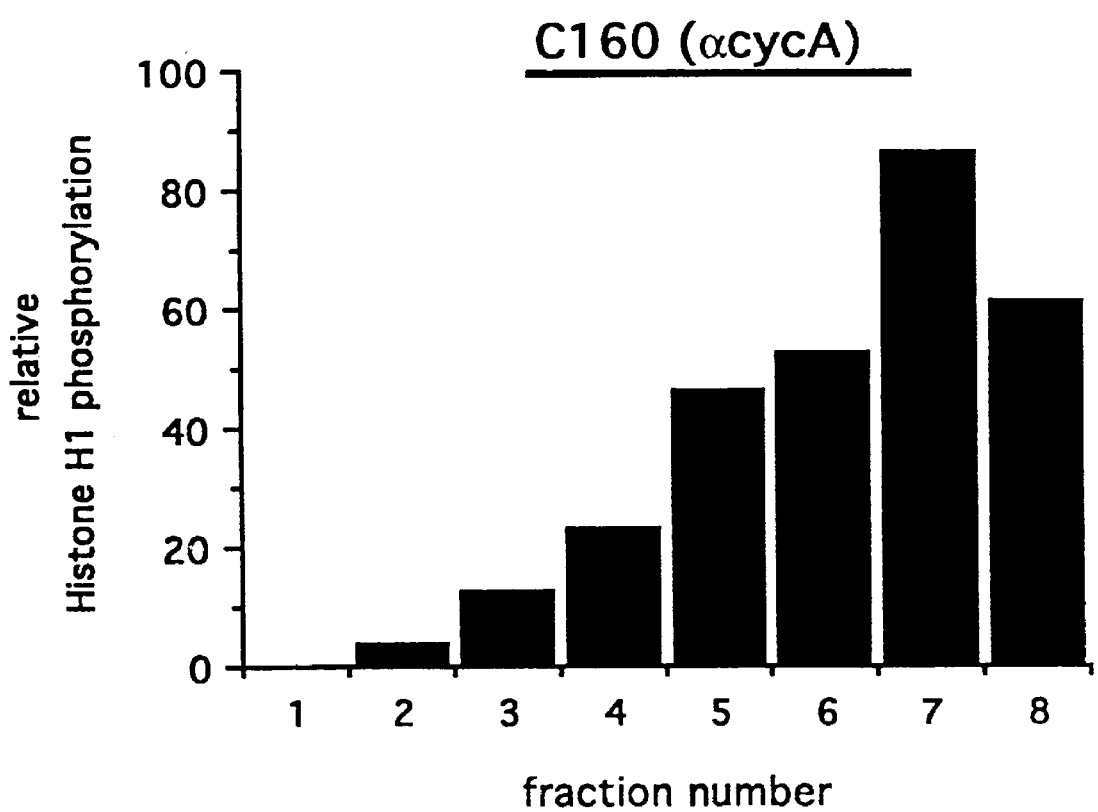

The activity of the cyclin E-associated kinase during the cell cycle is markedly different from the kinases associated with cyclin A. C160 anti-cyclin A monclonal antibodies were used to immunoprecipitate cyclin A and its associated proteins from the same cell extracts that had been used to measure cyclin E-associated kinase activity (FIG. 9C). As previously described, cyclin A-associated kinase activity is first detected at the start of S phase (Pines and Hunter, 1990; Marraccino et al., 1992). In contrast to cyclin E-associated kinase activity, the cyclin A-associated kinase activity continues to rise throughout S phase and peaks in G2. These results also indicate that peak levels of the cyclin A-associated kinase are approximately 5 to 10-fold greater than the peak activity levels of the cyclin E-associated kinase (data not shown). However, the absolute levels may vary since the levels presented here depend upon two antibodies that may have slightly different association constants ($K_a$). These results suggest that a succession of distinct cyclin dependent kinase activities are activated during the cell cycle; kinase activity of cyclin E increases, followed by an increase in cyclin A- then cyclin B-associated kinase activity.

Figure 9D:
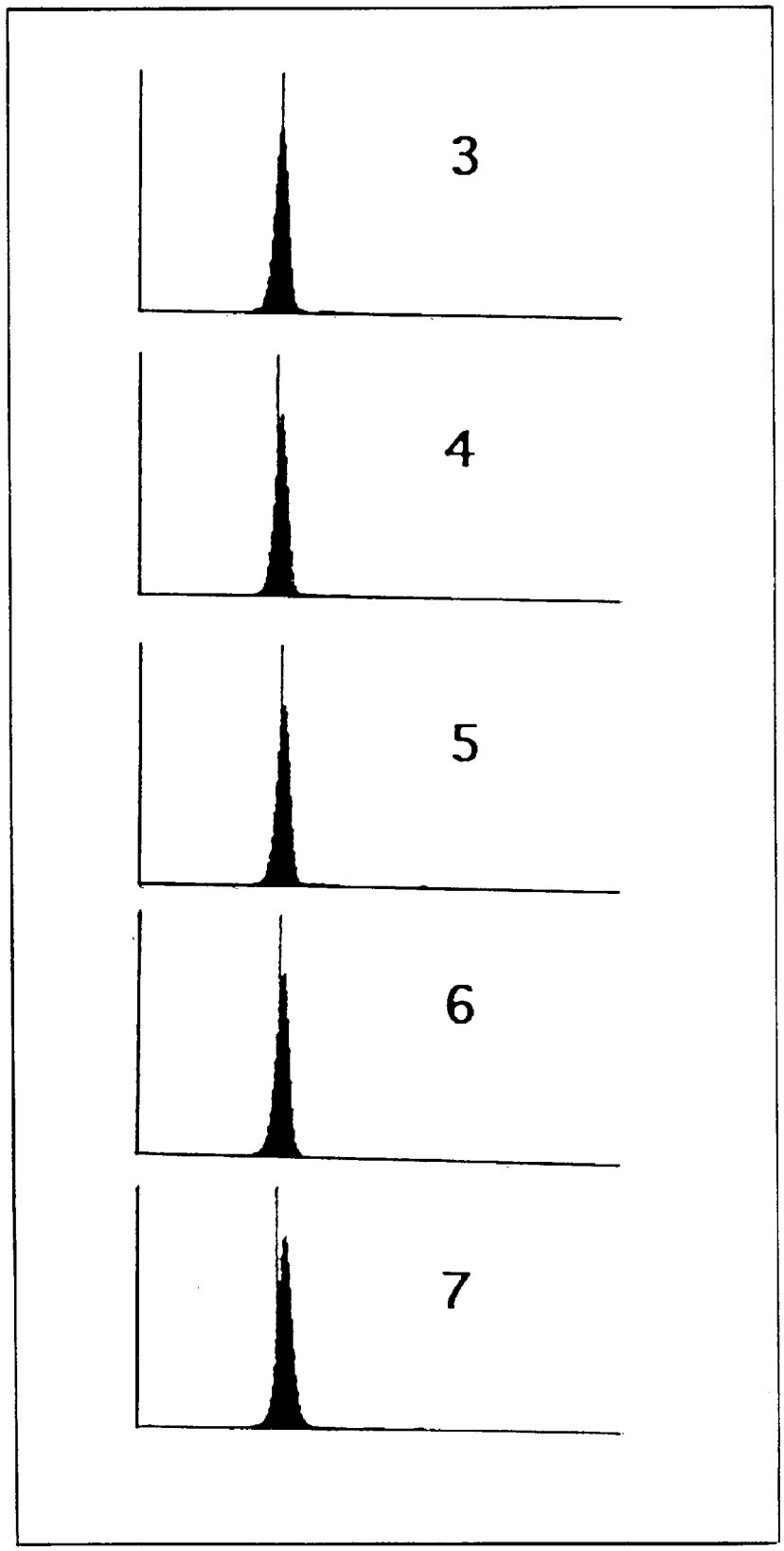

The kinetics with which the cyclin E-associated kinase activity accumulate during the G1 phase of the cell cycle was investigated as a relative measure of the abundance of the enzymatically active cyclin E:kinase complex. MANCA cells were arrested for 3 hours in the metaphase stage of the cell cycle with nocodazole at which time 75% of the cells had completed cytokinesis. Cells seperated from residual mitotic cells by elutriation were then released into the G1 phase of the cell cycle for 3,4,5,6 or 7 hours. They progressed synchronously into S phase after about 6 or 7 hours as determined by both flow cytometric measurement of nuclear DNA content (9D) and tritiated thymidine incorporation into chromosomal DNA (data not shown). Cells were then fractionated into sub-populations in different phases of the cell cycle by centrifugal elutriation. Cyclin E-associated kinase activity was found to be elevated during the G1 period reaching peak activity just as the cells entered S phase (FIG. 9D). In contrast, we found that cyclin A-associated kinases were not present in G1 and were first detected as cells entered S phase (FIG. 9E). In this experiment, cyclin A-associated H1 kinase activity was determined using C160 anti-cyclin A monoclonal antibodies to immunoprecipitate cyclin A-associated kinase activity. The elutriated G1 fraction of cells (fraction 2) was cultured at 32.5° C. to expand the G1 phase of the cell cycle. Aliquots of cells were harvested hourly for measurement of nuclear DNA content, and cyclin A- and cyclin E-associated kinase activities, up to the point where the cells approached and entered S phase.

Figure 10A:
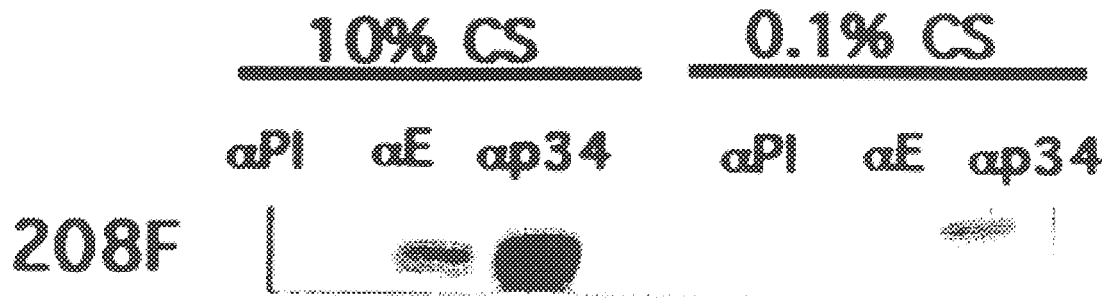
FIGS. 10A–10B, discussed in Example 8, shows the levels of cyclin E, as determined by measuring H1 kinase activity, in immunoprecipitates of quiescent, growing, or differentiating, rat 208F and PC-12 cells.
Figure 10B:

Cyclin E-associated kinase is readily detectable in proliferating rat 208F cells but disappears when they enter quiescence after serum withdrawal (FIG. 10A). Similarly, when rat PC12 cells were induced to differentiate into neurons by exposure to NGF, the cyclin E-associated kinase fell to low levels (FIG. 10B). In these experiments, we assayed H1 kinase activity in lysates from growing and quiescent rat 208F cells, and growing rat PC-12 cells. Immunoprecipates were prepared using affinity-purified antibodies against cyclin E ($\alpha$E), the C-terminus of human p34 CDC2 ($\alpha$p34), or as a control pre-immune anti-cyclin E antiserum ($\alpha$PI). Cells were induced to grow using 10% calf serum (10%CS, FIG. 10A) and to differentiate using NGF (+NGF, FIG. 10B). Quiescent controls were grown in 0.1% calf serum (0.1%CS, FIG. 10A). Nondifferentiating controls were grown in the absence of NGF (–NGF, FIG. 10B). These results demonstrate that cyclin E-associated kinase activity is growth regulated as are the levels of cyclin E expression.

Example 9

Constitutive expression of cyclin E shortens G1

The pattern of cyclin E-associated kinase activity during the cell cycle suggested that the physiological function mediated by cyclin E takes place during the G1 phase of the cell cycle. To test this possibility, stable cell lines were constructed that constitutively expressed human cyclin E from a retroviral LTR promoter. The effects of constitutive cyclin E expression on cells, and on cell cycle kinetics was tested.

Figure 11D:
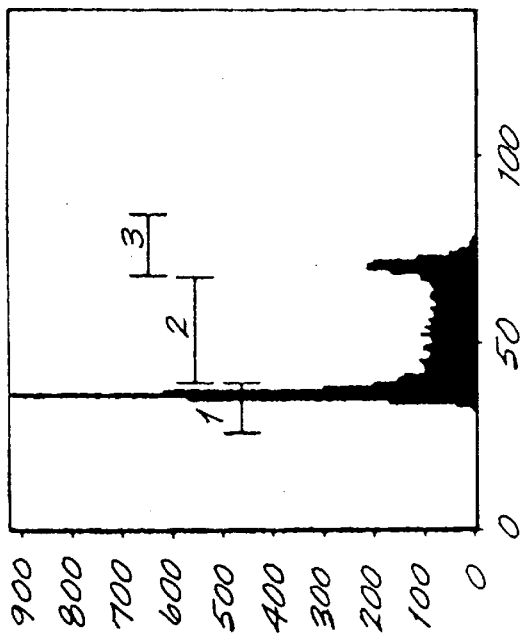
Figure 11C:
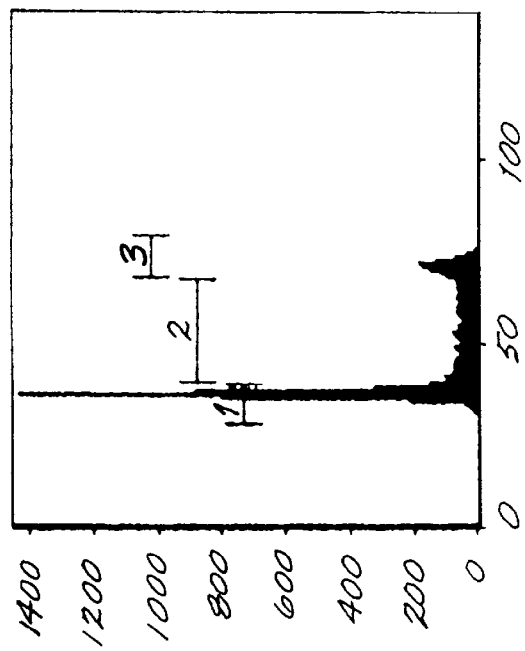
Figure 11E:
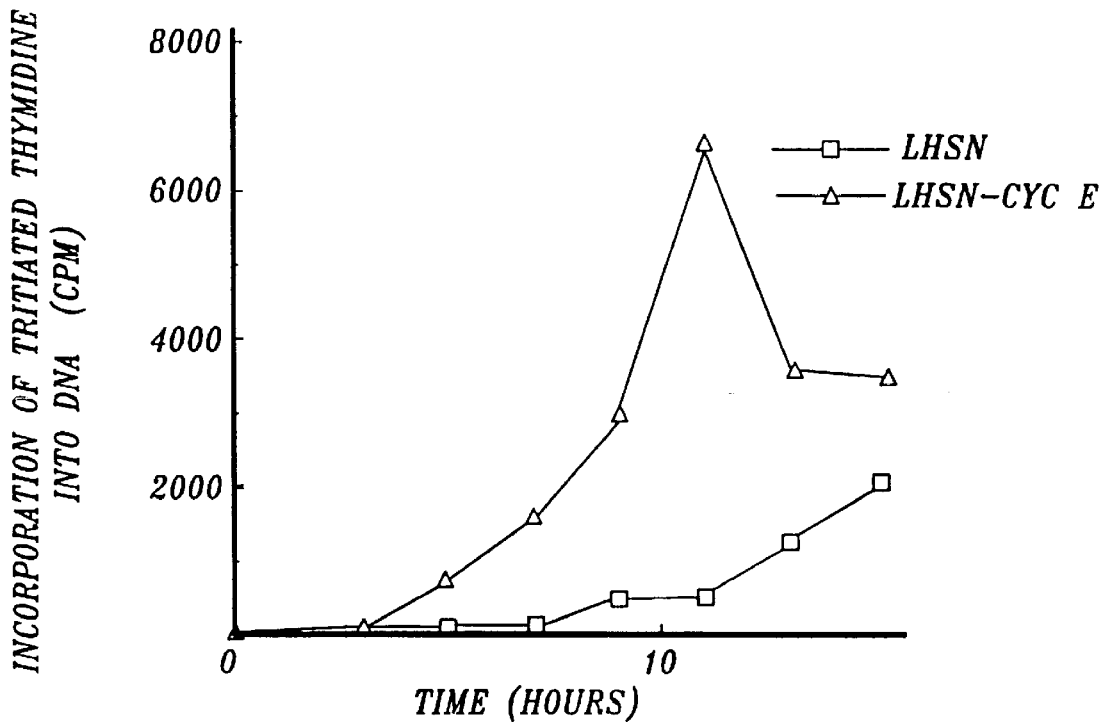

A human cyclin E cDNA was cloned into the retroviral expression vector, LXSN (Miller & Rosman, 1989), which expresses the inserted cDNA from the 5' LTR and contains the neomycin phosphotransferase gene as a selectable marker. The construct permits production of retroviral vector particles having either amphotropic or ecotropic host range specificity. We used an ecotropic stock of vector particles to infect the Rat-1 fibroblast cell line and selected a pool of over ten thousand independently infected cells by growth for 2 weeks in G-418 containing selective media. At the same time, a pool of LXSN control vector-infected cells was generated. Pools of infected cells were studied rather than individual selected cell clones to minimize any possible clonal variation that might be present within the Rat-1 cell line. The results, presented in FIG. 11A, show that the LXSN-cyclin E infected cells contained approximately 5 to 10-fold more cyclin E protein than could be detected in the cells infected with the control LXSN viral vectors. Two cyclin E bands, at 45 kDa (the size of full length cyclin E) and 40 kDa, were specifically expressed in cyclin E transduced cells. Increased cyclin E:kinase activity was also observed in the LXSN-cyclin E transduced cells. The results in FIG. 11B show a 3 to 5-fold increase in the level of cyclin E-associated histone H1 kinase activity in exponentially growing cultures of Rat-1 cells. The lower levels of cyclin E and cyclin E-associated kinase detected in the control cells was presumably due to endogenous rat cyclin E. To evaluate the effects of cyclin E on the cell cycle, exponentially growing LXSN-cyclin E transduced cells were collected by centrifugal elutriation. The distribution of transduced cells within the cell cycle was determined by flow cytometry after DNA staining with propidium iodide (FIG. 11C). Cells transduced with LXSN-cyclin E showed a decrease in the fraction of cells in the G1 phase of the cell cycle in comparison to control cells transduced with the control vector, LXSN. The cyclin E transduced cells also showed an increase in the fraction of cells in the S phase of the cell cycle. These observed changes in the fractions of cyclin E transduced cells in the different phases of the cell cycle are consistent with accelerated transit of the cells through the G1 phase of the cell cycle. This was confirmed by directly measuring the length of the G1 phase in cyclin E infected cells. Cyclin E infected cells were synchronized in pseudometaphase by exposure to nocodazole, and mitotic cells collected. The mitotic cells were returned to culture and entry into S phase was monitored by pulse labeling with BrdU (5-bromodeoxyuridine). The BrdU was detected using immunochemical methods. The results, presented in FIG. 11D, show that the length of the G1 phase in the LXSN⁻ cyclin E infected cells (i.e., from conclusion of mitosis until resumption of DNA synthesis in S-phase) was substantially shorter than in cells transduced with LXSN.

In 5 separate experiments, using two independent pairs of transfected cell populations, the duration of G1 was, on average, 33% shorter in cells infected with the LXSN-cyclin E retroviral vector than in cells infected with the LXSN control vector. Similarly, studies conducted to measure the rate of entry of cyclin E-transduced cells into S phase using immunochemical detection of BUDR incorporated into nuclear DNA confirmed shortening of the S phase in LXSN-cyclin E transduced cells (data not shown). Due to the limited number of cells that can be obtained by mitotic shake-off methods, it was not possible to measure the level of cyclin E-associated kinase activity at each time point during progression from mitosis to S phase in the infected Rat-1 cell populations.

Example 10

Cyclin E-associated proteins

Figure 12:
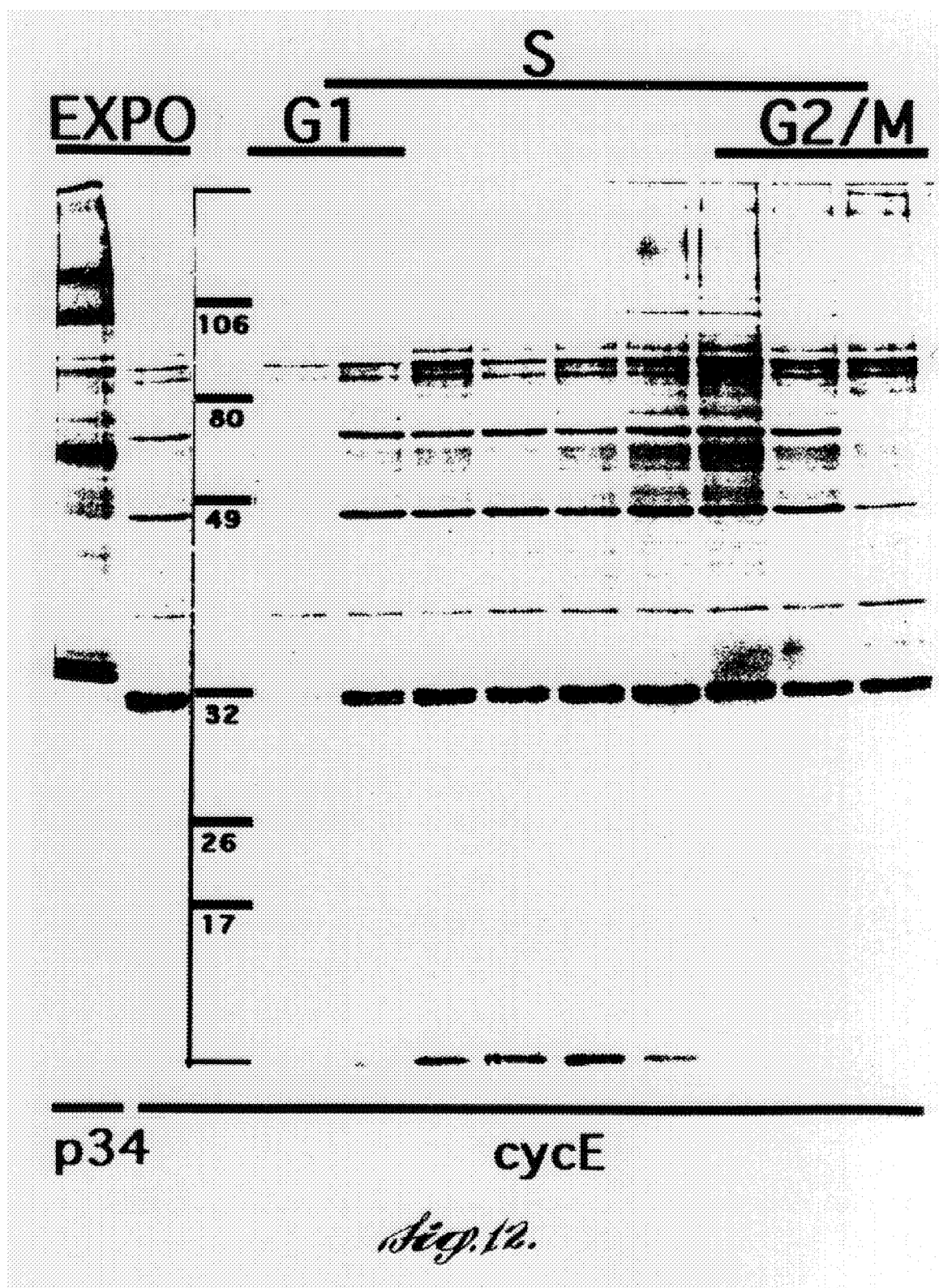
FIG. 12, discussed in Example 10, shows the results of a study analyzing proteins that are associated with cyclin E in exponentially growing MANCA cells at different stages in the cell cycle. The cyclin E-associated proteins were purified by immunoprecipitation with anti-cyclin E antibodies and SDS-PAGE.

Previous Examples have shown that cyclin E can activate human p34 CDC2, and human or Xenopus p33 CDK2, when the proteins are expressed together in budding yeast. Furthermore, the results have shown that cyclin E can bind and activate both human CDC2 and human CDK2 in vitro (i.e., in cell-free systems). The association of kinases with cyclin E was examined in in vivo studies, (i.e., in cells), where cell extracts were prepared from elutriated cell cycle fractions of exponentially growing MANCA cells that were biosynthetically radiolabeled with [$^{35}$S]-methionine for 3 hours. Extracts were prepared in SDS-RIPA buffer and the specific proteins were immunoprecipitated using affinity purified anti-cyclin E antibodies (prepared against GST-cyclin E fusion protein), and an antiserum against the C-terminus of human CDC2 (p34). Immunoprecipitates were collected, washed, and boiled in the SDS buffer prior to separation on 12% SDS-polyacrylamide gels. Detection of radiolabeled polypeptides in the gels was facilitated using sodium salicylate; and the gels were then dried for autoradiography. FIG. 12 shows the p34-associated proteins (Lane 1) and the proteins associated with cyclin E (Lanes 2–11) in exponentially growing cells (Lane 2), during G1-phase (Lane 3), G1/S (Lane 4), S (Lanes 5–8), S/G2 (Lanes 9–10) and M-phase (Lane 11). The molecular weights of the proteins associating with the cyclin E:CDC kinase complexes in the assay of FIG. 12 are summarized in Table 1, below. The 13 Kd polypeptide was associated with the complex during the middle of S-phase; the 17 Kd, throughout the cell cycle; the 32 Kd-doublet, mostly late in G1 and S; the 36 Kd, only in G1 and G2/M; the 70 Kd, predominantly in S; the 85 Kd (i.e., the lowest band in the triplet), throughout the cell cycle; and, the 107 Kd, in S-phase and just before and after S-phase. The difference in the expression pattern of the 32 Kd-double suggested that it was not CDK2 or CDC2, and this was confirmed by mapping the tryptic fragments of CDK2, CDC2, and the 32 kD band, designated band "x", associated with the immunoprecipitated complexes.

TABLE 1

Molecular Sizes of Cyclin E:CDC kinase Accessory Proteins

| Immunoppt.[a] | Cell Cycle Phase[b] | Presence of Band with Apparent Molecular Size (Kd)[c] | | | | | | |
|---|---|---|---|---|---|---|---|---|
| | | 13 | 17 | 32 | 36 | 70 | 85 | 107 |
| anti-p34 | Exponential | +/− | + | − | +/− | − | − | − |
| anti-cyclin E | Exponential | +/− | + | 2+ | +/− | 2+ | + | +/− |
| | G1 | + | + | + | + | + | + | − |
| | G1/S | + | + | 2+ | +/− | 2+ | + | + |
| | S | 2+ | + | 3+ | +/− | 3+ | 3+ | + |
| | S/G2 | 2+ | 2+ | 3+ | +/− | 2+ | 3+ | + |
| | G2/M | + | 2+ | 3+ | 2+ | + | 3+ | +/− |

[a]Immunoppt. = immunoprecipitate prepared with anti-p34 CDC2 or anti-cyclin E;
[b]Cell cycle phase, centrifugal elutriation fractions of cells; and,

TABLE 1-continued

Molecular Sizes of Cyclin E:CDC kinase Accessory Proteins

| Immunoppt.[a] | Cell Cycle Phase[b] | Presence of Band with Apparent Molecular Size (Kd)[c] | | | | | | |
|---|---|---|---|---|---|---|---|---|
| | | 13 | 17 | 32 | 36 | 70 | 85 | 107 |

[c]Molecular size in kilodaltons of polypeptides associated with cyclin E:CDC kinase complexes, 32 kd = middle of doublet, 85 kd = lowest band of triplet; amount indicated on a scale from − to 3+.

Figure 13:
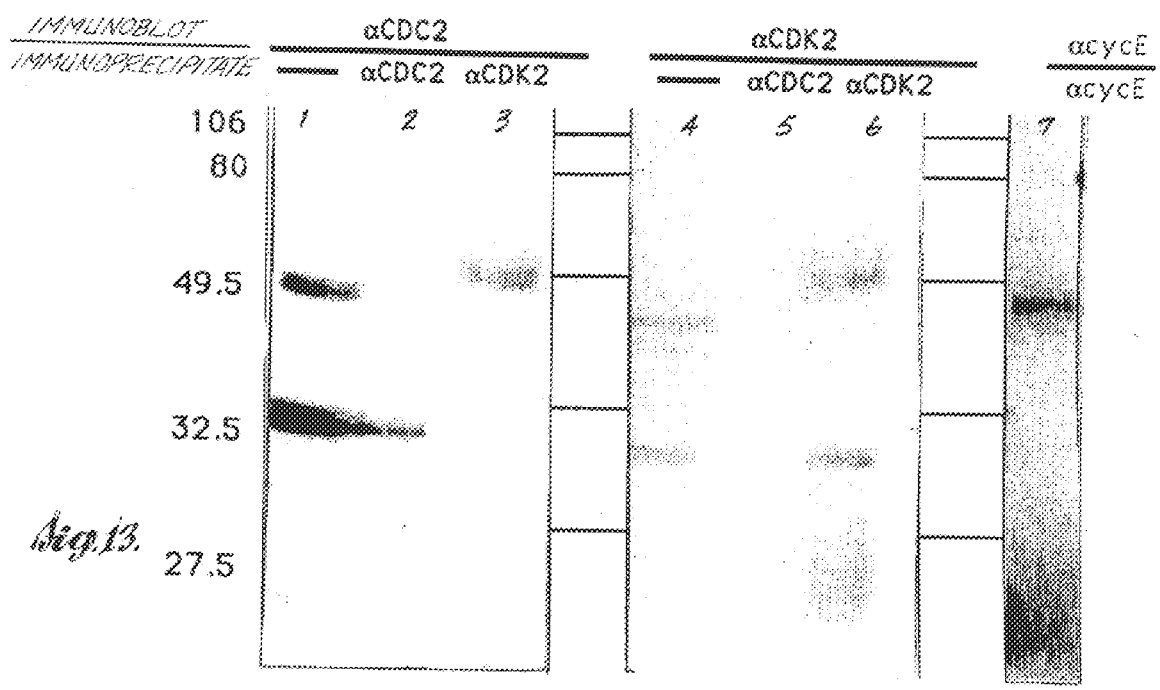
FIG. 13, discussed in Example 10, shows autoradiograms of Western immunoblots prepared following SDS-PAGE of immunoprecipitates prepared from MANCA cell extracts that were immunoprecipitated with anti-CDC2 ("αCDC2"), anti-CDK2 ("αCDK2"), or control serum ("−−") The results show the specificity of the anti-CDC2 and anti-CDK2 antibodies used in FIGS. 9–12 above. The immunoblots were visualized by reacting the gels with anti-CDC2 or anti-CDK2 followed by $^{125}$I-Protein A. The immunoprecipitates in lanes 1 and 2 were prepared using whole cell extracts; those in lane 3 and 4 were control extracts that were precleared of CDC2; those in lanes 5 and 6 were precleared of CDK2; and lane 7 was an extract of MANCA cells arrested at the G1/S boundary. The positions migrated by protein molecular weight standards is as indicated.

A series of control immunoprecipitation reactions were conducted to characterize the specificity of anti-CDC2 and anti-CDK2 antibodies. Lysates from exponentially growing MANCA cells were immunoblotted using affinity purified antibodies directed toward the 7 C-terminal amino acids of human p34 CDC2 (αCDC2) or antiserum directed toward the 15 C-terminal amino acids of human p33 CDK2 (αCDK2). In FIG. 13, lanes 1 and 2 are immunoblots of whole cell extracts; in lanes 3 and 4, whole cell extracts were first immunoprecipitated with affinity purified anti-p34 CDC2 antibodies and then blotted with the indicated antibodies; in lanes 5 and 6, extracts were first immunoprecipitated with an antiserum against the C-terminus of p33 CDK2 and then blotted with the indicated antibodies. Note the presence of a non-specific signal derived from the immunoprecipitating antibody between 50 and 80 kDa. An extract from MANCA cells arrested at the G1/S boundary with aphidicolin was immunoprecipitated using affinity purified antibodies against human cyclin E and then blotted using the same antibodies. A single protein band at 45 kDa was detected. Therefore, the associated proteins in cyclin E immunoprecipitates were most likely bound to cyclin E and were not detected due to nonspecific cross-reactivity with this antibody.

Figure 14A:
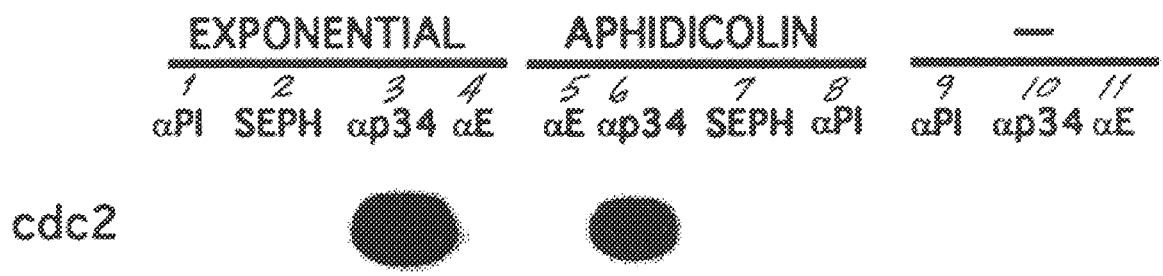
FIGS. 14A–14B described in Example 10, shows Western immunoblots detecting complexes of CDC2 and CDK2 with cyclin E in exponentially growing MANCA cells and cells arrested at the G1/S boundary with aphidicolin by methods described in Example 10.

To confirm these results, immunoblotting was used to examine the association between cyclin E and both p33 CDK2 and p34 CDC2 in extracts prepared from MANCA cells growing exponentially or arrested at the G1/S boundary with aphidicolin. The aphidicolin blocked cells were chosen because the activity of the cyclin E-associated kinase is maximal at the G1 to S phase transition. Cell extracts were immunoprecipitated using affinity-purified anti-cyclin E antibodies and the immunoprecipitates western blotted using both CDC2 and CDK2 specific antisera. For all immunoprecipitations the antibodies had been cross-linked to sepharose. Immunoprecipitations were carried out with preimmune serum ("αPI"), blank sepharose beads ("SEPH"), affinity purified anti-p34 CDC2 C-terminus ("αp34"), and affinity purified anti-cyclin E ("SE") (FIG. 14A). The set of lanes labeled "−" contained no cell extract. Both antisera were raised against peptides corresponding to the C-termini of the respective proteins. The C terminus of the CDC2 related proteins is not highly conserved. The results show that the anti C-terminus CDC2 antiserum recognized CDC2 and not CDK2, and conversely that the anti-C-terminus CDK2 antiserum recognized CDK2 and not CDC2 (FIG. 13).

Immunoblots of whole cell extracts show two forms of CDK2 (Rosenblatt et al., 1992; see also FIG. 14A). In both aphidicolin arrested cells (FIG. 14A) and in exponentially growing cells (not shown; see FIG. 15) cyclin E preferentially associated with a more rapidly migrating form of CDK2. The identification of CDK2 in cyclin E immunoprecipitates has been confirmed using 3 different antisera independently raised against the C-terminus of human CDK2. All three antisera recognize CDK2 and not CDC2 (Rosenblatt et al., 1992; Elledge et al., 1992; FIG. 13). The more rapidly migrating forms of CDK2 are currently believed to be more highly phosphorylated (Rosenblatt et al., 1992). This is consistent with our observation that all the cyclin E-associated isoforms of CDK2 detected in [$^{35}$S]-methionine-labeled cell extracts were also detected in anti-cyclin E immunoprecipitates from [$^{32}$P]-orthophosphate-labeled cell extracts.

Figure 14B:
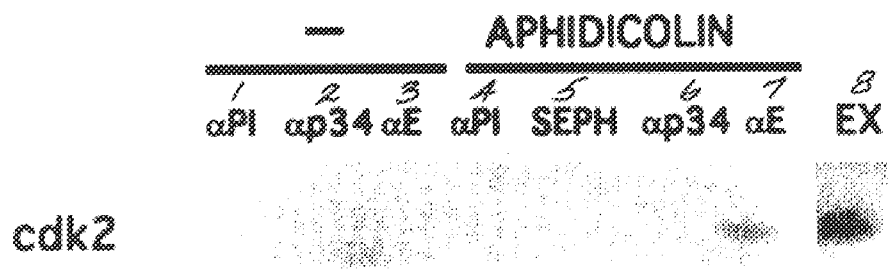

The results show that p34 CDC2 was also detected in the cyclin E immunoprecipitates although its abundance was substantially less than that of CDK2. In exponentially growing cells, a predominantly hypophosphorylated form of p34 CDC2 was detected, while in aphidicolin-arrested cells there were also more highly phosphorylated forms of p34 CDC2 associated with cyclin E (FIG. 14B). In both cases, it was possible to detect only very small amounts of p34 CDC2 associated with cyclin E.

Example 11

Cell cycle dependent formation of a cyclin E:CDK2 complex

Figure 15A:
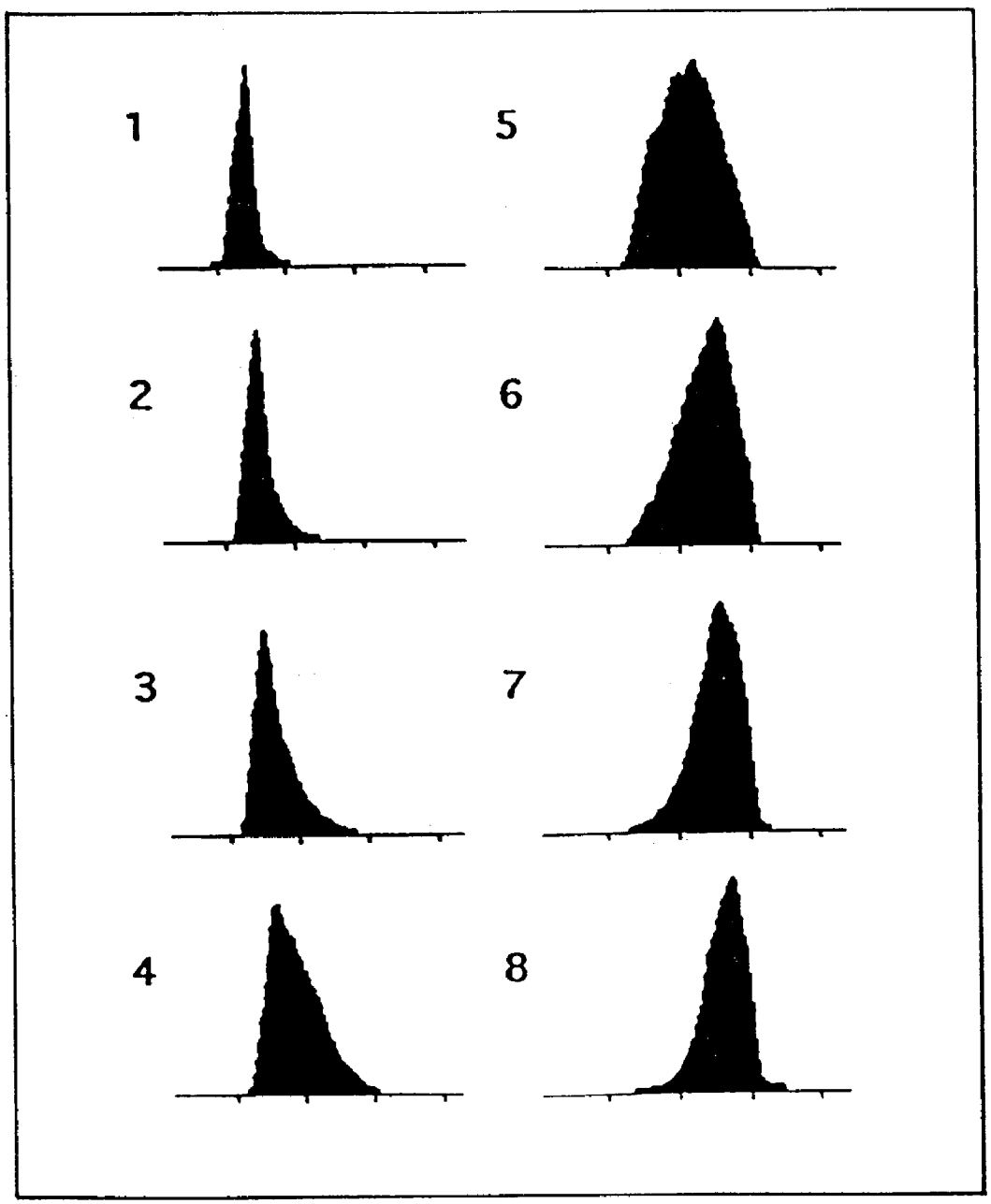
FIGS. 15A–15F, described in Examples 11–12, shows the results of studies designed to determine the level of expression of cyclin E and abundance of the cyclin E:CDK2 complex at different stages in the cell cycle.
Figures 15B, 15C:
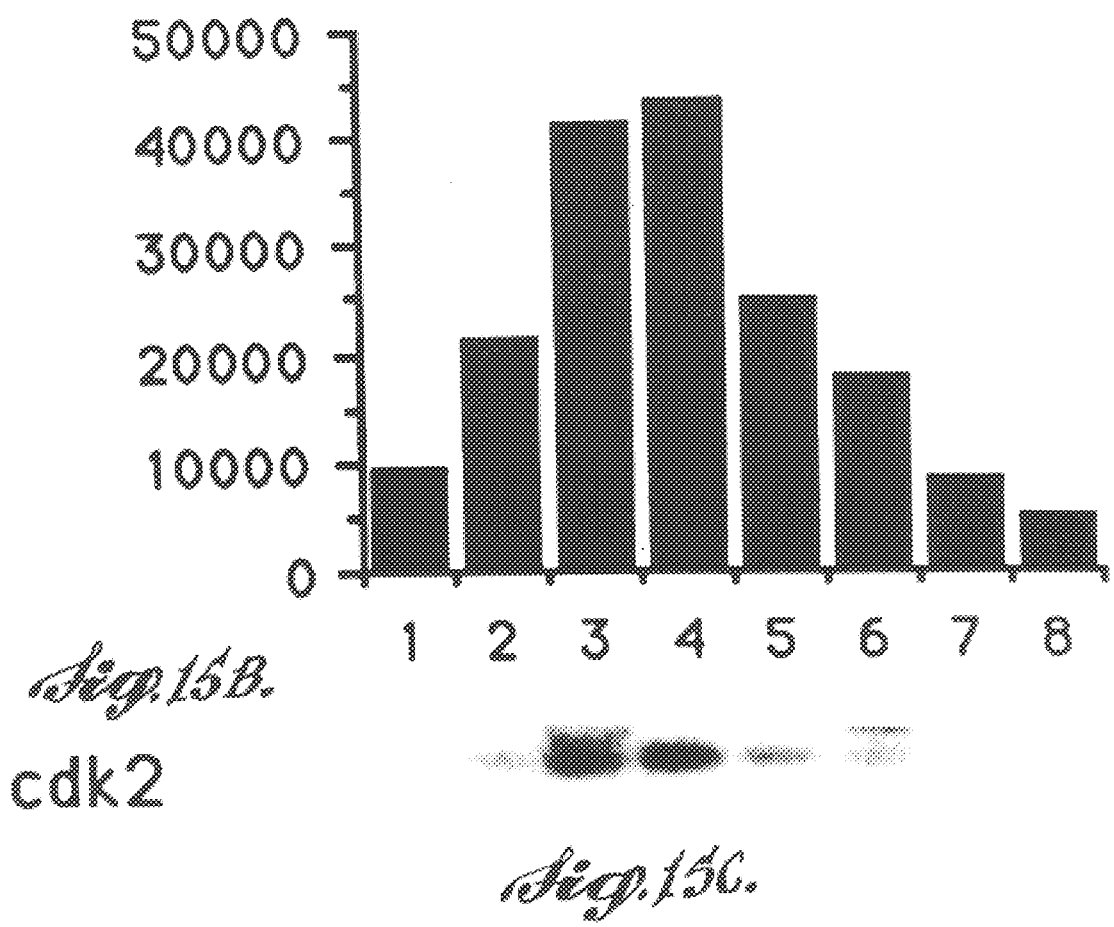
Figures 15D, 15E:
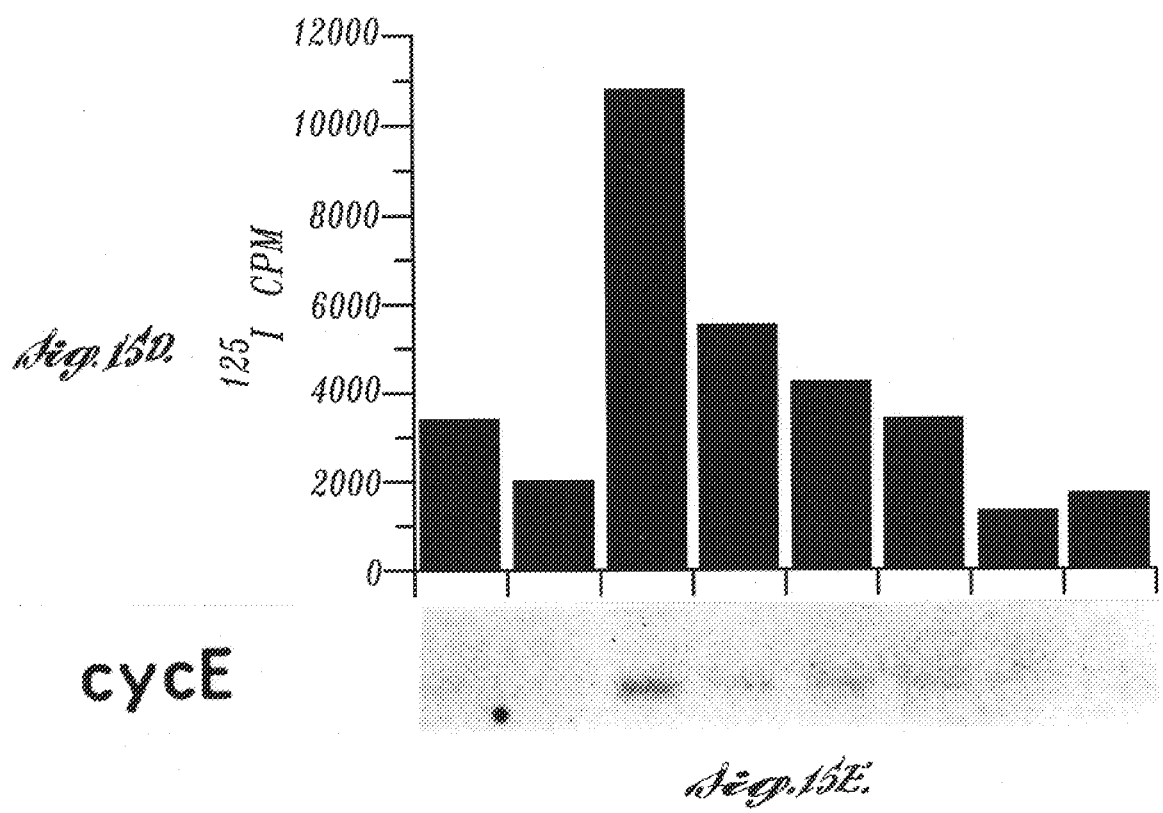

The phase in the cell cycle at which cyclin E and CDK2 form an enzymatically active complex was investigated. Exponentially growing MANCA cells were separated into 8 cell cycle fractions by centrifugal elutriation and cellular extracts prepared. The cell cycle position of the cells in each fraction was determined by flow cytometric measurement of nuclear DNA content (FIG. 15A). Cyclin E and its associated proteins were immunoprecipitated using affinity-purified anti-cyclin E antibodies. We visualized the presence of CDK2 by Western blotting using an antiserum specific for the C-terminus of CDK2 (FIG. 15B–E ). The results show that the level of enzymatically active cyclin E:CDK2 complex peaked during late G1 and early S phase and declined in abundance as cells progressed through the remainder of the cell cycle. The abundance of the cyclin E-CDK2 complex closely corresponded to the cell cycle periodicity of the cyclin E-associated kinase (as described in prior Examples). Furthermore, the present results suggest that in exponentially growing cells, cyclin E:CDK2 complexes did not accumulate in an inactive form prior to their activation in late G1. This pattern of appearance and activation was observed to be similar to the pattern reported for cyclin A-associated kinase activity, i.e., the activity of which reportedly increased in direct proportion to the abundance of cyclin A (Pines and Hunter, 1990; Marracino et al., 1992). However, the present results were different from those obtained with the cyclin B:p34 CDC2 complex in that the cyclin B:CDC2 complex reportedly accumulates during S and G2, inactive and highly phosphorylated, prior to their activation at the onset of mitosis (Gould and Nurse, 1989; Pondaven et al., 1990; Solomon et al., 1990).

Example 12

Abundance of cyclin E is cell cycle regulated

Figure 15F:
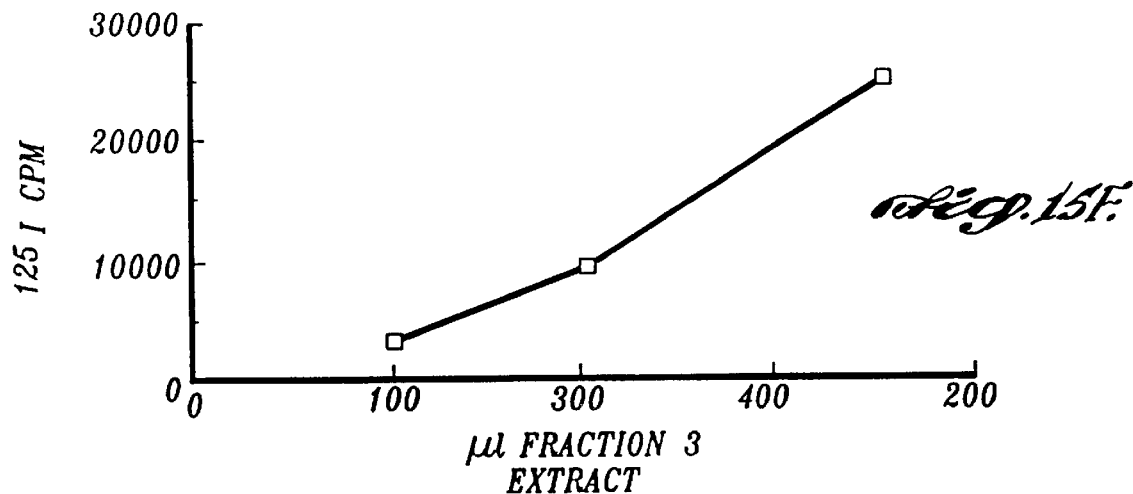

The abundance of the cyclin E protein was determined at different phases of the cell cycle. MANCA cells were separated into fractions representing each stage of the cell cycle by centrifugal elutriation. We analyzed cell lysates from each fraction by immunoprecipitation using affinity-purified anti-cyclin E antibodies which we also used to measure the abundance of cyclin E in the immunoprecipitates. The results showed that cyclin E levels were maximal in late G1 and declined in S, G2 and M (FIG. 15B–E ). The immunoassay procedure was found to accurately reflect the relative levels of cyclin E in each cell cycle fraction since the amount of cyclin E protein detected was linearly dependent on the amount of cell extract used in the immunoprecipitation (FIG. 15F). In sum, these results suggest that the abundance of the cyclin E:CDK2 complex, and hence the periodicity of the cyclin E-associated kinase activity, may be directly regulated by the level of cyclin E.

Example 13

Assembly of cyclin E:CDC2 and cyclin E:CDK2 complexes in vitro

Figure 16A:
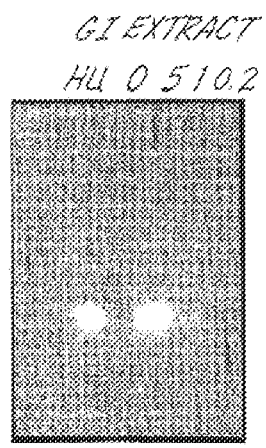
FIGS. 16A–16C described in Example 13, shows the results of studies designed to investigate the molecular association of cyclin E with CDC2 and CDK2; assembly of cyclin E:CDC2 or cyclin E:CDK2 complexes in vitro,; and activation of phosphorylase kinase activity following association of the kinases with cyclin E.
Figure 16B:
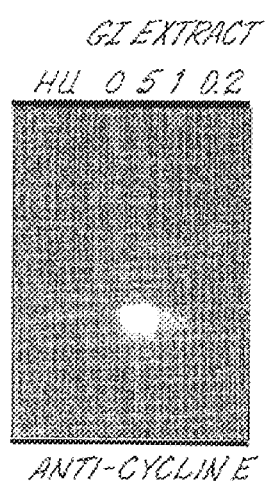
Figure 16C:
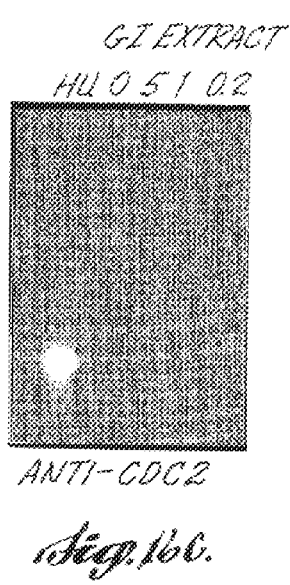

As shown, cyclin E preferentially associates with p33 CDK2 rather than p34 CDC2 in human cells. One possible explanation for this is that the affinity of cyclin E is different for CDK2 than for CDC2. This possibility was evaluated in a cell-free system of recombinant cyclin E and cell extracts containing CDC2 and CDK2 kinases. Cyclin E was expressed in Sf9 insect cells using baculovirus vectors. Cyclin E protein were over-expressed in the transduced insect cells, the intracellular concentrations was approximately 5–10 $\mu$M after 48 hours (Desai et al., 1992), and these cells were harvested and proteins extracted for analysis. The binding between cyclin E, CDC2, and CDK2 was evaluated using diluted insect cell extracts as a source for cyclin E, and extracts from G1 cells as a source of CDC2 and CDK2. To determine cell-cycle-dependent differences in the effects of cyclin E on the CDC2 and CDK2 kinases, cell extracts were prepared from cells whose growth was arrested for 12 hours (i.e., prior to S-phase) in media containing 2 mM hydroxyurea (causing cells in S-phase to stop and all other cells to pile up next to S-phase) followed by release of growth for 3.5 hours to allow all cells to enter S-phase ("HU" FIGS. 16A–16B); as well as, from cells blocked with nocodazole, released for three hours into G1, and then further selected by centrifugal elutriation ("G1", FIGS. 16A and 16B). All cell extracts were prepared in hypotonic buffer. The incubation mixtures were designed to bring the concentration of the three proteins close to the normal physiologic levels at approximately 0.2 $\mu$M. Diluted lysates containing the indicated cyclin E, CDC2, and CDK2 proteins were incubated alone or in combination for 30 minutes at 37° C. under conditions suitable for in vitro replication of SV40 origin containing plasmids (D'Urso et al., 1990). The formation of cyclin E:CDC2 and cyclin E:CDK2 complexes in the incubation mixtures was determined using immunoprecipitation either with antisera to CDC2 (anti-CDC2), the C-terminus of CDK2 (anti-CDK2), or cyclin E (anti-cyclin E) followed by SDS-PAGE, and autoradiography (FIGS. 16A, 16B, 16C). The kinase activity associated with the different respective immunoprecipitates was determined in the H1 kinase assay (as described in the Examples, above).

Figure 17:
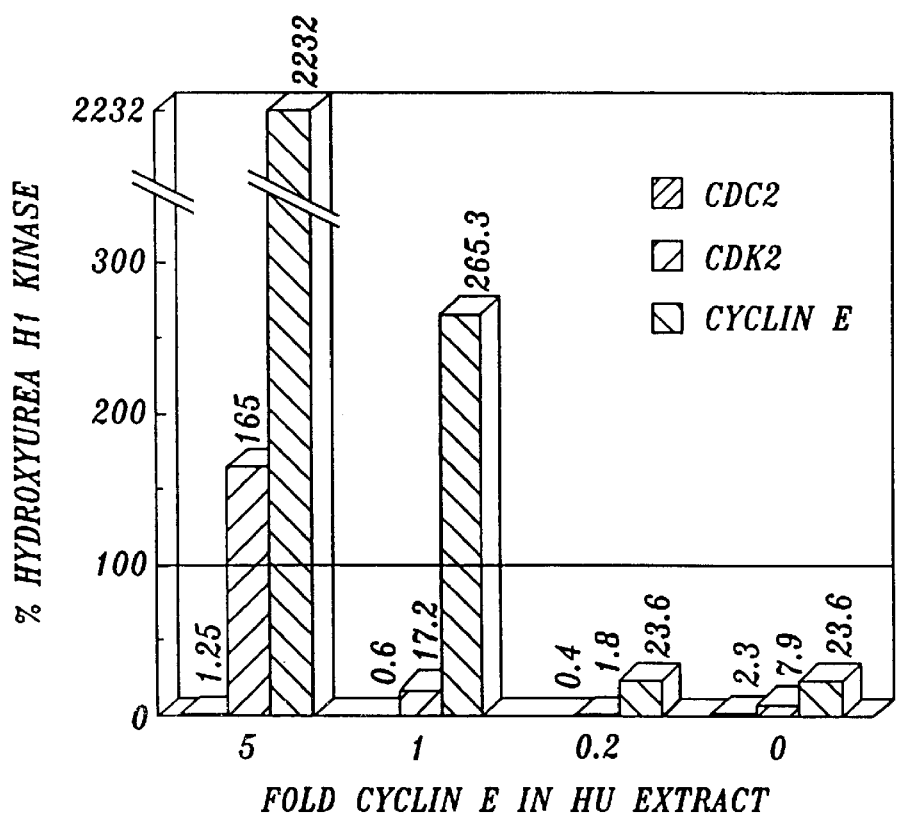
FIG. 17 graphically depicts the results obtained in FIGS. 16A, 16B, and 16C, above. The results obtained with each respective G1 cell extract immunoprecipitate (CDC2, solid/left-most bars in set of three bars; CDK2, hatched bars/middle of each set; or, cyclin E, shaded/right-most bars in each set of three) is expressed as a percentage of the phosphor imaging signal obtained with the kinase in the HU-cell extract immunoprecipitate (i.e., 100%; %hydroxyurea H1 kinase). The numbers at the top of each bar are the maximal value recorded in percent (%). The results show that cyclin E activated a latent CDK2 kinase activity in the G1 cell extracts and the activity of the kinase was dependent upon the amount of cyclin E added (i.e., expressed as the fold-dilution of the cyclin E added to the HU extract; "fold cyclin E in HU extract"). The results indicate that the availability of cyclin E is a factor controlling phosphorylase kinase activity during the G1 phase of the cell cycle.

The immunoprecipitates were tested for their ability to mediate phosphorylation of histone H1 (i.e., H1 kinase activity) by mixing the immunoprecipitates with histone H1 and $\gamma$-$^{32}$P orthophosphate. $^{32}$P-radiolabeled histone H1 was detected by SDS-PAGE and phosphor imaging (FIG. 16A, 16B, 16C). (The phosphor imaging in FIGS. 16A–16C was quantified and the results are graphically presented in FIG. 17.) CDC2 kinase activity, while evident at low levels in immunoprecipitates prepared from HU-arrested cells (FIG. 16C, "HU"), was decreased to nearly undetectable levels during G1-phase (FIG. 16C, G1 extract, "0") and the level of kinase activity was not altered by addition of different amounts of cyclin E to the cell extract (i.e., FIGS. 16A, 16B, 16C, "5, 1, 0.2"). In contrast, CDK2 kinase activity present at low levels in HU-arrested cell extracts (FIG. 16A, "HU"), decreased to undetectable levels in G1 (FIG. 16A, G1 extract, "0"), but when cyclin E was added to the G1 cell extract (FIG. 16A, "5,1,0.2") the CDK2 kinase activity was restored. The results show activation of a latent CDK2 kinase activity in the G1-phase cell extracts following addition of cyclin E, and suggest that kinase activity is regulated by the abundance of cyclin E. Quantitive aspects of these studies are presented in FIG. 17, where the level of cyclin E-mediated activation of CDK2 kinase activity was measured (i.e., using phosphor imaging of the SDS-PAGE gels presented in FIGS. 16A, 16B, and 16C, above) as a function of the amount of cyclin E added to the G1 phase cell extract ("fold cyclin E in HU extract"; FIG. 17). (The differing amounts of Sf9 lysate containing cyclin E in FIG. 17 correspond to the "5, 1, and 0.2 " amounts in FIGS. 16A, 16B, and 16C.) The phosphor imaging data for the kinase activity of each of the CDC2, CDK2, and cyclin E immunoprecipitates was normalized by calculating the activity as a percentage of the activity seen in cell lysates of HU-arrested control cells (i.e., 100%; "%hydroxyurea H1 kinase"; FIG. 17). The results presented in FIG. 17 show that the level of CDK2 kinase activity was dependent upon the amount of cyclin E added to the G1 extract, and that levels of CDK2 kinase activity were achieved which were more than 22-fold greater than those observed in the HU-arrested cell extracts (i.e., cyclin E immunoprecipitate at 5-fold cyclin E; FIG. 17). In addition, the results show that the kinase activity associated with the cyclin E-immunoprecipitates was consistently greater than that associated with CDC2 immunoprecipitates. The results also confirm the previous findings (above) that only low levels of CDC2 activity are present in the G1-phase cell extracts, and that any latent CDC2 that might be present in these extracts is not appreciably activated by the addition of cyclin E.

These combined results suggest activation of kinase activity by cyclin E resulting from formation of a cyclin E:CDK2 complex. In other studies (not shown) the association of cyclin E with CDC2 or CDK2 was verified using molecular-sieve gel chromatography on Superose 12. p34 CDC2 and p33 CDK2 monomers eluted at 30–40 kDa and had negligible histone H1 kinase activity. When insect cell extracts containing recombinant cyclin E were mixed with the CDK2-containing lysate, the majority of the CDK2 protein eluted at an approximate molecular size of 160 kDa, suggesting formation of a cyclin E:CDK2 complex. In contrast, when extracts containing a similar amount of CDC2 were mixed with the cyclin E lysate only a small fraction of CDC2 protein associated in a stable manner with cyclin E. The cyclin E:CDC2 and cyclin E:CDK2 complexes eluted from the molecular sieve column exhibited kinase activity.

Discussion of Examples 8–13

Cyclin E is a G1 Cyclin

The proliferation of eukaryotic cells is primarily regulated by a single decision which occurs during the G1 phase of the cell cycle—either to enter the cell cycle and divide or to withdraw from the cell cycle and enter a quiescent state (reviewed in Baserga, 1985; Pardee, 1989). In yeast, the biochemical process that underlies this cellular decision is the assembly and activation of a complex between the CDC8 protein kinase and the CLN type cyclins (reviewed in Nurse, 1990; Hartwell, 1992). Recent experiments in a variety of model systems support the idea that the role of the CDC2-related kinases have been evolutionarily conserved (D'Urso et al., 1990; Blow & Nurse, 1990; Furakawa et al., 1990; Fang & Newport, 1991). The observations presented here demonstrate that human cyclin E specifically activates a CDC2 related kinase during the late G1 phase of the cell cycle and that cyclin E accumulation is rate-limiting for G1 transit. Therefore, we suggest that in all eukaryotes a critical step in the biochemical pathway that controls cell proliferation is the assembly of a cyclin/CDK complex (the term CDK is used to designate a cyclin dependent kinase in the CDC2 protein family).

The evidence that cyclin E functions during the G1 phase of the human cell cycle can be summarized as follows: Cyclin E can perform the G1 START functions of the yeast CLN proteins since it can complement mutations in the yeast CLN genes (Koff et al., 1991; Lew et al., 1991). Furthermore, we have shown that cyclin E in combination with either human CDC2 or human CDK2 could rescue yeast strains that were doubly mutated for both CLN and CDC28 function (Koff et al., 1991). However, the specificity of the assay was suspect since human cyclin B, which clearly functions during mitosis and not during G1, could also rescue CLN mutations (Koff et al., 1991; Lew et al., 1991; Xiong et al., 1991). As reported here, cyclin E associates with a protein kinase in human cells and this kinase is cell cycle regulated. The activity of the cyclin E-associated protein kinase, as well as the abundance of the cyclin E protein, peaks during late G1 and early S phase, and then declines as cells progress through S, G2 and mitosis. This kinase is also growth regulated, since it is absent from cells that have exited the cell cycle and differentiated or become quiescent. The relative timing of cyclin E and cyclin A activity is significant. Cyclin A protein and cyclin A-associated kinase activity are detectable as soon as S phase starts (Marraccino et al., 1992), and cyclin A function is necessary for S phase to begin (Girard et al., 1991). We have also shown that cyclin E accumulates before cyclin A and that the cyclin E-associated kinase appears earlier in the cell cycle than the kinase associated with cyclin A. This biochemical function of cyclin E during G1 suggested that its physiological function would precede the S phase role of cyclin A. This was directly shown by constitutively expressing human cyclin E in the rat fibroblast cell line, Rat-1. We found that 5 to 10-fold overexpression of cyclin E caused a 3 to 5-fold increase in the level of cyclin E-associated kinase activity. This level of cyclin E overexpression caused a 30–35% decrease in the length of the G1 phase of the cell cycle.

The abundance of the cyclin E protein is normally cell cycle regulated—it shows a sharp peak in late G1. This is probably due to regulation of the cyclin E mRNA level (Lew et-al., 1991) since it fluctuates during the cell cycle in parallel with the level of the cyclin E protein. The mRNA's encoding cyclin E, A and B are cell cycle regulated and predict the pattern of accumulation of the respective cyclin proteins (Pines and Hunter, 1989, 1990). In budding yeast, accumulation of the CLN mRNA's is under positive feedback control and result in a rapid rise in CLN mRNA and protein levels at START (Cross and Tinkelenberg, 1991; Dirick & Nasmyth, 1991). The association of cyclin proteins with transcription factors in mammalian cells may be part of an analogous mechanism that controls the timing of cyclin gene expression during the cell cycle (Bandara et al., 1991; Mudryj et al., 1991; DeVoto et al., 1992; Shirodkar et al., 1992). While cyclin accumulation is in part determined by the levels of the respective mRNA's, cyclin abundance can also be controlled by protein turnover (Murray & Kirschner, 1989; Glotzer et al., 1991). It is not known whether the stability of the cyclin E protein is regulated during the cell cycle, but the protein lacks the consensus sequence recognized by the ubiquitinating enzyme that mediates the mitotic turnover of cyclins A and B (Glotzer et al., 1991).

The Cyclin E:CDK2 complex

The data suggest that the major cyclin E-associated protein kinase is CDK2. Two dimensional gel analyses of $^{32}$P or $^{35}$S-met labelled proteins show that the major CDC2-related protein associated with cyclin E in human cells is CDK2. While there is not direct evidence that the cyclin E:CDK2 complex is an active kinase in vivo, this is the most likely conclusion. The abundance of the cyclin E:CDK2 complex is cell cycle regulated and closely parallels the levels of the cyclin E-associated kinase. Furthermore, the CDK2 protein bound to cyclin E is primarily in the more rapidly migrating of the two forms detectable by one dimensional PAGE. This downward mobility shift is known to correlate with both binding of CDK2 to cyclin and activation of the CDK2 kinase (Rosenblatt et al., 1992). It is thought to be indicative of phosphorylation of threonine 160, which is a prerequisite for activation of the CDK2 kinase (Y. Gu and D. M., unpublished observations). It has also been shown that the cyclin E:CDK2 complex can substitute for the CLN/CDC28 complex in *S. cerevisae* (Koff et al., 1991), and that the cyclin E:CDK2 complex is an active kinase in vitro.

The periodic accumulation of the cyclin E protein in cells appears to match that of the cyclin E:CDK2 complex, whereas the CDK2 protein is present at invariant levels during the cell cycle (Rosenblatt et al., 1992). Therefore, it would seem that the abundance of the cyclin E:CDK2 complex is primarily regulated by the level of the cyclin E protein. However, the phosphorylation state of cyclin E could also control the assembly of the complex.

At least six phosphorylated isoforms of CDK2 are associated with cyclin E. This complexity was surprising since only two of these isoforms had been detected bound to cyclin A. Preliminary evidence indicates that CDK2 is phosphorylated on 3 residues homologous to those phosphorylated in CDC2 (Y. Gu and D. M., unpublished observations)—T14, Y15 and T160. Combinatorial phosphorylation of these sites might account for the six CDK2 isoforms. It seems more likely, however, that other phosphorylation sites are also present since immunoprecipitates with anti-CDK2 antibodies contained two additional phosphorylated isoforms of CDK2, bringing the total number detected to eight (FIG. 11A). One interpretation is that the cyclin E:CDK2 complex integrates the information provided by the many signals that control cell proliferation, e.g., by binding second messengers involved signal transduction. The multiply phosphorylated forms of CDK2 may reflect the influence of diverse mitogenic signals on the activation of the cyclin E:CDK2 complex. The multiple CDK2 phosphates could have both positive and negative effects on CDK2 activity and a particular phosphorylated state may be required for specific functions. The downstream activation of the cyclin A:CDK2 complex, which occurs after commitment to the cell cycle has been made, may be responsive to much fewer factors and therefore biochemically less elaborate.

Other evidence has indicated that CDK2 might play a role during the G1 of S phases of the cell cycle. In cycling cells, CDK2 kinase activity precedes CDC2 kinase activity (Rosenblatt et al., 1992). Our experiments in *S. cerevisae* showed that in certain genetic backgrounds CDK2 can complement the G1/S function of CDC28 and not its G2/M functions (Koff et al., 1991). Also, depletion of CDK2 from extracts of activated Xenopus eggs prevents the start of DNA replication (Fang and Newport, 1991). All these results are consistent with a role for CDK2 in committing the cell to the cell cycle.

The Cyclin E:CDC2 Complex

Cyclin E can interact with both human CDK2 and human CDC2 when the proteins are expressed together in yeast and cyclin E can activate both the CDK2 and CDC2 kinases in vitro (Examples, above). We have shown that although the cyclin E:CDK2 complex is more abundant in human cells, the cyclin E:CDC2 complex is also present. In addition, complexes between cyclin E and other proteins were observed (FIG. 12; Table 1) that may potentially modulate or change cyclin E activity. The pattern of cyclin E-associated kinase activity during the cell cycle showed some differences from the abundance of the cyclin E:CDK2 complex. These differences may be attributable to the cyclin E:CDC2 or the other cyclin E complexes.

The low level of the cyclin E:CDC2 complex in vivo appears to be a consequence of the relatively low affinity of cyclin E for CDC2. The reconstitution experiments presented here show that the cyclin E:CDK2 complex readily formed under conditions where very little cyclin E bound to CDC2. We have found, however, that cyclin E is present in multiple phosphorylated states in vivo. Therefore, another possibility is that only certain relatively rare isoforms of cyclin E can bind to CDC2.

We previously observed that a mutation in the yeast CDC28 gene greatly curtailed the ability of cyclin E, but not cyclin B, to rescue CLN function and, consequently, we suggested that cyclin E might interact with CDC28 differently than cyclin B (Koff et al., 1991). In vitro reconstitution experiments support this idea by showing that cyclin B bound to CDC2 effectively (Desai et al., 1992) while only small amounts of cyclin E:CDC2 complex could be detected.

Other Cyclin E:CDC Complexes

The results presented in FIG. 12 and Table 1, above, may also be interpreted to indicate the possible existence of other cell division kinases, previously unrecognized, that associate with cyclin E. The 32 Kd band "x" protein (Table 1, FIG. 12) is certainly a candidate for such a novel kinase protein, both based on the similarity in size with the known CDC2 and CDK2 kinases, and its apparent association with cyclin E.

G1 Regulation in Mammalian Cells

In 1974 Pardee proposed that the proliferation of mammalian cells is regulated by extracellular mitogenic signals at a point during the G1 phase of the cell cycle called the restriction point (Pardee, 1974). If these signals were not present, or if the cell was incapable of appropriately responding to them (e.g., if protein synthesis is inhibited) then the cell would not traverse the restriction point and entered a quiescent state, called $G_0$ (reviewed in Zetterberg, 1990). While cells can respond to a wide array of extracellular mitogenic signals, one gets the impression that there is much less diversity in the intracellular events triggered by these signals (see Cantley, 1991; Chao, 1992). Indeed, it is not unreasonable to expect that there might be a final common point through which the diverse mitogenic pathways must pass, and that this is the restriction point (Pardee, 1974).

There are few molecular details about restriction point regulation. In normal cells, progression through the restriction point is very sensitive to the rate of protein synthesis (Rossow et al., 1979, Schneiderman et al., 1971; Brooks, 1977). Prior to the restriction point (but not after) small and transient decreases in protein synthesis cause substantially longer increases in the length of G1 (Zetterberg & Larson, 1985). Removal of extracellular mitogenic stimuli and inhibition of cellular protein synthesis, in fact, are thought to deter the same cell cycle event (Pardee et al., 1981). To account for the disproportionately large effect on G1 length by relatively small changes in the rate of protein synthesis, it was proposed that a labile protein must accumulate during G1 in order for the cell to traverse the restriction point (reviewed in Pardee, 1989).

It is appealing to speculate that a cyclin is this labile regulator of the restriction point and that formation and/or activation of a cyclin/CDK complex is a rate-limiting event in G1 progression. The periodic accumulation of cyclin E during the cell cycle indicates that it is a relatively short lived protein, and its G1 peak in abundance may be consistent with a role at the restriction point. Also, the decrease in G1 length by constitutive cyclin E expression suggests that entry into S phase may be limited by the abundance of cyclin E. It is important to remember, however, that not all of G1 is eliminated by constitutive cyclin E expression. Mostly likely, there are some essential G1 events whose duration is not effected by abundance of cyclin E. Examples of this might include chromosome decondensation and nuclear membrane assembly. Furthermore, it has been reported that in some circumstances the G1 restriction point occurs less than one hour before S phase starts (Wynford-Thomas et al., 1985) while in other cases the restriction point can occur much earlier in G1 (Pardee, 1974). Our measurements indicate that the maximal cyclin E-associated kinase levels are reached relatively late in G1. This is particularly apparent in serum stimulated cells where much of G1 is completed before the cyclin E-associated kinase is detected (A. K. and J. R., unpublished observations). Other cyclins, such as cyclin D and cyclin C, may also be expressed during G1 (Matsushime et al., 1991; Motokura et al., 1991; Lew et al., 1991) and it is possible that the sequential formation of multiple cyclin:CDK complexes is required for the cell to traverse G1. In that case, constitutive cyclin E expression might shorten only the latter stages of G1.

In *S. cerevisae* factors that control passage through START can effect CLN function, apparently at multiple levels (Change & Herskowitz, 1990; Cross and Tinkelenberg, 1991). By analogy, we might expect G1 cyclin function in mammalian cells to be controlled by proteins that modulate cell proliferation. For example, it would not be surprising to observe direct interactions between cyclin E and members of the Rb protein family (Bandara et al., 1991; Mudryj et al., 1991; Shirodkar et al., 1992; DeVoto et al., 1992). Also, expression of the cyclin E gene might be regulated by one or more of the oncogenic transcription factors.

Example 14

Growth factor-dependence of cells constitutively expressing cyclin E

The cell division cycle of all normal higher eukaryotic cells is controlled by specific extracellular growth factors that are required for cell division. The families of known growth factors is diverse and includes such proteins as insulin, PDGF, IGF, EGF, GM-CSF, G-CSF, TGF, erythropoeitin, and other stem cell factors. Different cell types display particular growth factor requirements, determined in part by the growth factor receptors expressed on their cell surface and by their state of differentiation. Typically, cells in tissue culture require exogenous growth factors in an animal serum (i.e., fetal bovine serum) to grow; or in chemically defined serum-free medium specific growth factors must be added. In the absence of the requisite growth factor(s), cells stop dividing and arrest in G1. The results presented in the Examples above indicated that the level of cyclin E, and/or the activity of the cyclin E:cell division kinase complex, may be rate-limiting for transit of cells through G1. Therefore, it was reasoned that cell proliferation might be regulated through steps requiring cyclin activation (e.g., increased cyclin gene transcription or translation; or increased cyclin:kinase complex activity) and that growth factors might act upon cells by activating cyclins. Assuming that cyclin activation is required for proliferation two hypotheses were considered: a unitary hypothesis in which a cell at a particular stage of differentiation has a single cyclin that can be triggered by a single growth factor; and a multiform hypothesis, wherein a single growth factor activates multiple cyclins and the combined action of all the cyclins in the cell is required to trigger cell proliferation. It was reasoned that if the simple cause-and-effect logic of the unitary hypothesis held true, then modifying cyclin E levels in a cell might alter the growth factor requirements of the cell for proliferation in vitro; while if the multiform hypothesis held true, then any alteration in a single cyclin might be masked by the action of all the other cyclins in the cell. To test these two hypotheses, cells were transduced with the LXSN-cyclin E vector sequences.

Figure 18A:
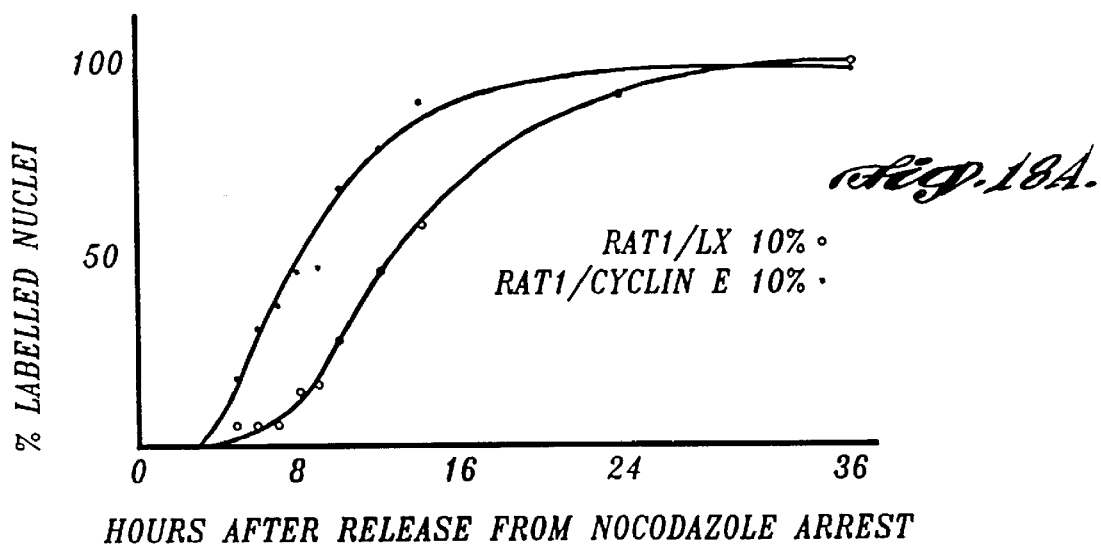
FIGS. 18A–18B described in Example 14, graphically represents the effects of serum growth factors on the rate at which LXSN-cyclin E-transduced Rat- 1 cells and LXSN-transduced control cells initiate DNA synthesis following nocodazole-arrested mitosis. The incorporation of BrdU into nuclear DNA was measured in LXSN-cyclin E-transduced (RAT1/cyclin E) or LXSN-transduced (RAT 1/LX) control cells as a function of time after the nocodazole mitotic block. Only cells synthesizing DNA (i.e., S-phase cells) incorporate BrdU into DNA and scoring the number of nuclei in a cell culture (i.e., % labelled nuclei) can thus be used to evaluate the rate of transition of the cells from G1 into the S-phase.
Figure 18B:
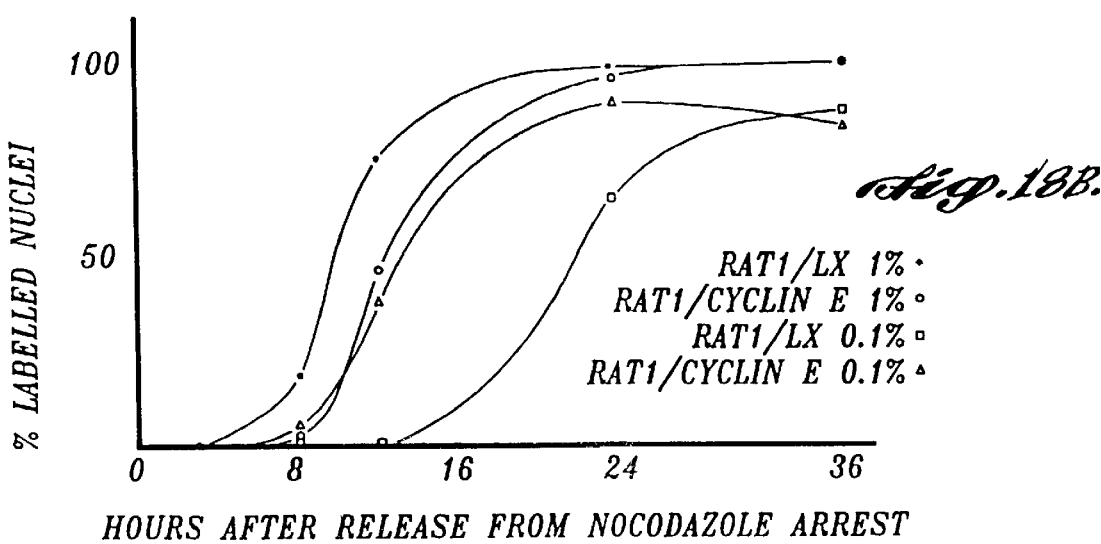

Primary cultures of human fibroblasts and rat Rat-1 cells were infected with LXSN-cyclin E vector particles, or as a control with LXSN (as described in Example 9). The transduced cells were tested for expression of cyclin E (as described above), and LXSN-cyclin E-transduced Rat-1 and human fibroblasts were found to express 3-to 5-fold greater levels of cyclin E protein than the cells from which they were derived (and 3-to 5-fold greater than control LXSN-transduced cells). The growth-factor dependence of LXSN-cyclin E-transduced human cells was determined by measuring tritiated thymidine incorporation into DNA in serum free medium (D-MEM) or medium supplemented with 10%, 1%, 0.1%, or 0.01% (v/v) fetal bovine serum (Table 2) and the growth factor dependence of Rat- 1 cells was determined by measuring BrdU incorporation in 10%, 1.0% or 0.1% serum (FIG. 18A–18B). In the BrdU assay, only cells that are synthesizing DNA (i.e., S-phase cells) incorporate BrdU into DNA and score positive in the assay. Therefore, the rate of accumulation of BrdU positive cells can be taken as a relative measure of the rate at which cells transition from the conclusion of one mitosis through G1-phase and into the next round of DNA synthesis (i.e., S-phase). The results presented in FIGS. 18A and 18B show the percent of the total cell nuclei that were labeled with BrdU in cultures of LXSN-transduced control Rat-1 cells ("RAT1/LX", open circles) and LXSN-cyclin E-transduced cells ("RAT1/cyclin", closed circles) as a function of time after releasing mitotic arrest induced by nocodazole treatment. The growth factor dependence of the cells was evaluated by culturing the cells in 10% bovine calf serum (FIG. 18A) or in 1% or 0.1% serum (FIG. 18B). The results in FIGS. 18A and 18B show that a) irrespective of the percentage of serum in the culture medium, the LXSN-cyclin E-transduced cells initiated DNA synthesis more rapidly than control cells; and, b) the LXSN-cyclin E-transduced cells exhibited increased resistance to low serum (i.e., 0.1%) and initiated DNA synthesis about 10–12 hours sooner than the control cells (FIG. 18B).

In a similar manner, the results presented in Table 2 show that LXSN-cyclin E-transduced human fibroblasts and Rat-1 cells exhibit reduced growth factor requirements for proliferation. In control cells (i.e., LXSN-transduced cells) when serum was reduced from 10% to 0.1% the cells continued to proliferate and incorporate thymidine into DNA, although at a reduced rate, with levels 11% of those observed in the presence of optimal levels of growth factors (i.e., 10% serum). In contrast, the growth of LXSN-cyclin E-transduced cells was reduced to 19% of maximal levels (seen in 10% serum) but this level was more than 2-fold higher than the level observed in the control LXSN-transduced cells. In addition, when PDGF (10 ng/ml) was added to cyclin E-transduced cells growing in 0.1% serum, the levels of proliferation were 50% of the maximal level occuring in the presence of 10% serum (Table 2). In contrast, when PDGF was added to control human fibroblasts growing in 0.1% serum no stimulation of thymidine incorporation was observed.

TABLE 2

Growth Factor Dependence of Vector-Transduced Human Fibroblasts

| Transducing Vector | Serum (%) | PDGF[a] | $^3$H-TdR (CPM)[b] | Percent Max CPM[c] |
|---|---|---|---|---|
| LXSN | 10 | 0 | 524,300 | 100 |
|  | 0.1 | 0 | 59,359 | 11 |
|  | 0.1 | + | 55,788 | 11 |
| LXSN-cyclin E | 10 | 0 | 708,871 | 100 |
|  | 0.1 | 0 | 137,712 | 19 |
|  | 0.1 | + | 356,284 | 50 |

[a]+ = PDGF (10 ng/ml) added to the culture media; 0 = no PDGF;
[b]$^3$H-TdR, tritited thymidine incorporation determined 36 hours after adding 1–2 μCi/ml $^3$H-TdR to culture medium;
[c]Percent Max CPM, % maximal $^3$H-TdR CPM = (CPM in 0.1%)/(CPM in 10% serum)

(Flow cytometric analysis confirmed the continued presence of cycling cells in LXSN-cyclin E-transduced Rat-1 and human fibroblast cells in the presence of 0.1% serum). The combined results show that the LXSN-cyclin E-transduced Rat-1 cells have a reduced growth factor dependence for transitioning the G1 phase of the cell cycle.

These combined results support the hypothesis that over-expression by 3–5 fold of a single cyclin, i.e., cyclin E, can partially (but not completely) restore the ability of cells to proliferate in the absence of growth factors, and fully restore proliferation in the presence of a single growth factor, PDGF. Thus, the results tend to favor a unitary hypothesis in which one cyclin and one growth factor regulate growth of a cell at a particular stage of differentiation; however, this interpretation is not supported by the quantitative aspects of the data, i.e., over-expression did not render the cells completely growth factor independent. Therefore, the possibility also exists that cyclins other than cyclin E are participating in the stimulation of cell proliferation in the presence of PDGF. (The results could thus be interpreted as providing support for a multiform model of cell proliferation where activity of several cyclins and growth factors combines to promote cell proliferation.)

In summary, the results can be interpreted to provide support for either a unitary or multiform model of cell proliferation. Aside from any interpretations, the results are significant for demonstrating that genetic manipulation of a single cyclin in a cell and treatment with a single growth factor is sufficient to dramatically alter the conditions required to grow cell in vitro. It appears from the results that with the proper combination of G1 cyclin expression in a particular cell: a) a cell line may be produced whose proliferation is largely unconstrained in the absence of exogenous growth factors; and b) a cell line may be produced whose proliferation is largely dependent upon one or more selected growth factors. In viewing the potential long-term significance of the present findings it may be worthwhile to recall that it took Sam Hanks nearly 10 years of research to develop Hank's Balanced Salt Solution (HBSS); about an additional 3–5 years for Eagle to develop Eagle's Minimal Essential Medium (MEM); and still longer for Rene Dulbecco to achieve a D-MEM formulation. (Media such as RPMI 1640 and M199 still carry a number that designates how many formulations preceded their development.) The findings described herein are thus highly significant, for showing that simple manipulation of a single protein in a cell is sufficient to promote propagation of the cell in vitro in the near complete absence of serum growth factors.

Materials and Methods

Plasmids and libraries

The human cDNA library was a gift from J. Colicelli and M. Wigler. It was prepared from the human glioblastoma cell line U118 in the vector pADNS (Colicelli et al., 1988). The portion of the library used in these experiments contained cDNA inserts that had been selected to be >2 kb. In the experiments involving isolation of human CDC2 homologs, the cyclin E cDNA was transferred to the vector pMAC. This 2µ-based vector uses the ADH promoter to drive expression of the human cDNA and contains the TRP1 selectable marker. For expression of cyclin E in E. coli a SmaI-PvuII fragment containing the entire cyclin E coding region was cloned into the unique SmaI site in the vector pGEX-3T (Amgen). For in vitro transcription/translation reactions, the SmaI-NotI fragment of cyclin E was cloned into the MscI site in the vector pCITE-1 (Novagen). For in vitro translation of human cyclins A and B, cDNAs with genetically engineered NcoI sites at the initiating methionine were generously provided by Jonathan Pines and Tony Hunter. PCITE vector was cleaved with SalI, blunt-ended with Klenow enzyme and then cleaved at the unique NcoI site. Cyclin cDNAs were isolated by cleavage with EcoRI (for cyclin A) or BamHI (for cyclin B), blunt-ended with Klenow and then cleaved with NcoI. The Xenopus CDK2 clone, pEMBLYe30/2, has been described previously (Paris et al., 1991). For some assays in yeast, the cyclin A, B, and E cDNAs were subcloned into the vector pADANS, which is identical to pADNS except that the first 10 amino acids of the ADH protein are fused to the expressed protein.

Antibodies

The peptide YLDNQIKKM (SEQ. ID. NO. 3), corresponding to the C terminus of human CDC2, was synthesized chemically and covalently coupled to BSA via the tyrosine residue for injection into rabbits. For affinity purification, rabbit serum was precipitated with 50% ammonium sulfate, resuspended in 10 mM sodium phosphate (pH 8.0) and dialyzed extensively with 10 mM sodium phosphate, 0.15M NaCl, pH7.2 (PBS). Affinity columns were prepared by coupling the peptide to CNBr-activated Sepharose using conditions recommended by Pharmacia. The dialysate was applied to the affinity column equilibrated in PBS. The follow-through was subsequently reloaded twice. The column was washed with 10 column volumes of PBS+2M KCl, and protein subsequently was eluted with 10 column volumes of 5M NaI+1 mM sodium thiosulfate (made fresh before use). Fractions containing immunoglobulin were determined by absorbence at 290, pooled, and dialyzed extensively against PBS. The peptide CEGVP-STAIREISLLKE (SEQ. ID. NO. 4), corresponding to the conserved "PSTAIRE" domain of the CDC2 gene family, was synthesized chemically and coupled to keyhole limpet hemocyanin (KLH) via the cysteine residue, and antibodies were prepared in rabbits and affinity purified as described above. The peptide YDEAEKEAQKKPAESQKIERE (SEQ. ID. NO. 5), corresponding to residues 104–123 of human cyclin A, was synthesized chemically and coupled to BSA, and antibodies were prepared in rabbits and affinity purified as described above.

Antibodies directed against CDK2 were raised against a peptide corresponding to the 15 C-terminal amino acids of human CDK2 coupled to keyhole limpet hemocyanin. Two other antisera against the 9-C-terminal amino acids of human CDK2 were also used in the course of these experiments (Elledge et al., 1992; Rosenblatt et al., 1992). The polyclonal anti-cyclin E antisera has been described (Koff et al., 1991).

For preparation of cyclin E antibodies, E. coli containing GEX-cycE (see below) were grown to an $OD_{600}$ of 0.4–0.6, and fusion protein expression was induced with 10 mM IPTG. After 3 hours of additional growth at 30° C, the E. coli were pelleted, washed once with PBS, and again with GEX buffer A (60 mM Tris-HCl pH 8.0, 25% sucrose, 10 mM EDTA) and stored at −75° C. Cells were resuspended in 1/30 the original culture volume in GEX buffer A containing 1 mM phenylmethylsulfonyl fluoride (PMSF), 10 µg/ml leupeptin, 100 µg/ml soybean trypsin inhibitor (SBTI), and 10 µg/ml N-tosyl-L-phenylalanine chloromethyl ketone (TPCK). Protease inhibitors were used in all subsequent steps. SDS was added to 0.03% and cells were lysed by sonication. Lysates were clarified by centrifugation at 13,000×g and added to a 1:1 slurry of Sepharose CL4B in GEX buffer C (0.02M HEPES-KOH (pH 7.6), 100 mM KCl, 1.2 mM EDTA, 20% glycerol, and 1 mM DTT) with 0.03% SDS, incubated for one hour at 4° C., and the Sepharose removed by low speed centrifugation. Cleared lysates were incubated with glutathione-agarose beads (SIGMA #G4510) (approximately 360 µg of GEX-cyclin E per ml of glutathione-agarose beads) for 1 hour at 4° C. The agarose beads were pelleted and washed 5 times with 10 volumes of GEX buffer C with 0.03% SDS, and the cyclin E fusion protein (GEX-E) eluted with buffer C with 0.03% SDS plus 5 mM glutathione. Fractions containing GEX-E were identified by SDS-PAGE electrophoresis and Coomassie blue staining. Rabbits were injected with 400 µg of total GEX-E protein in complete Freund's adjuvant; 320 µg was injected subcutaneously and 80 µg intramuscularly. Rabbits were boosted every 3 weeks with an identical regimen except incomplete Freund's adjuvant was used. Bleeds were obtained 7 days postinjection and analyzed by their ability to immunoprecipitate cyclin E produced in a rabbit reticulocyte lysate (Promega).

The specificity of the cyclin E antiserum was demonstrated by immunoprecipitation of in vitro translated cyclin E, A, and B. In vitro translated cyclins were made according to manufacturer's directions. Briefly, plasmids were linearized with either NheI (cyclin B/cyclin E) or PstI (cyclin A). Cyclin A was subsequently blunt ended with the Klenow enzyme before the transcription reaction. Transcription was carried out using the T7 RNA polymerase, and RNA was isolated by ethanol precipitation. Rabbit reticulocyte lysates were programmed with the RNA and incubated for 2 hours at 30° C. Programmed lysate (5 µl) was incubated with 10 µl of cyclin E antisera in 500 µl of 50 mM Tris-HCl pH 7.4, 250 mM NaCl, and 0.1% NP-40 for 1 hour at 4° C. Protein A-Sepharose was added and incubation continued for 1 hour. Protein A beads were pelleted and washed 4 times with 50 mM Tris-HCl, pH 7.4, 10 mM $MgCl_2$, 1 mM DTT, and 0.1 mg/ml BSA. The immunoprecipitates were resuspended in sample buffer and run on 12% SDS-PAGE gels. The gels were fixed and enhanced with 1M sodium salicylate before drying and autoradiography.

Cyclin E antibodies were affinity purified on columns of GST-cyclin E fusion protein. Approximately 100 ml of rabbit sera was precipitated with 50% ammonium sulfate. The precipitate was collected at 8,000×g and resuspended in 10 mM sodium phosphate pH 8.0 and dialyzed against PBS. The dialysate was adjusted to 10% glycerol and pre-cleared over a glutathione-S-transferase (GST) column. Flow through fractions were collected and the column regenerated by washing with 0.2M glycine pH 2.2. The column was re-equilibrated with PBS and this process was repeated 3 times.

Cleared sera was subsequently applied to a GST-cyclin E column. Following adsorption, the column was washed first with PBS and then with 2M KCl-PBS, and bound antibody was eluted with NaI-sodium thiosulfate as described (Koff et al., 1991). The eluate was dialyzed against coupling buffer (0.1M NaHCO$_3$ pH 8.3, 0.5M NaCl) and concentrated 5 to 10-fold using Centricon 10 concentrators (Amicon).

DNA Sequencing

Nested deletions of the cyclin E cDNA were sequenced on both strands using dideoxy chain termination methods.

Kinase assays

GEX-cyclin E (GEX-E) was purified as described up to the washing of the GEX-E bound to glutathione-agarose. For this experiment the beads were washed 3 times with 5 volumes of GEX buffer C with 0.03% SDS, 5 times with 10 volumes of buffer C with 0.5% Triton X-100, 5 times with 10 volumes of buffer D (30 mM HEPES-KOH pH 7.6, 7 mM MgCl$_2$, 100 mM NaCl, 1 mM DTT). 100 µl of GT-cyclin E-Sepharose beads, p13-Sepharose (5 mg of p13 per ml Sepharose), GT-Sepharose, or blank Sepharose were incubated with 100 µg of S-100 extract from human MANCA G1 cells (Roberts & D'Urso, 1988) in conditions used for in vitro replication of SV40 DNA (buffer D plus 3 µg creatine phosphokinase, 40 mM phosphocreatine, 0.25 mM dNTPs, 0.5 mM CTP, UTP, and GTP, 3 mM ATP). The beads were then pelleted and washed 5 times in kinase buffer (50 mM Tris-HCl pH 7.4, 10 mM MgCl$_2$, 1 mM DTT) plus 0.1 mg/ml BSA. For kinase assays the beads were resuspended in 50 µl kinase buffer +30 µM ATP, 5 µCi γ-$^{32}$P-ATP, and 1 µg histone H1, and incubated at 37° C. for 30 minutes. Products were analyzed by SDS-PAGE followed by autoradiography.

For studying the kinase bound to the SDS-GT-cyclin E-Sepharose beads, the GT-cyclin E beads and GT beads were prepared and incubated with G1 extracts and washed as described. Incubation of the beads at 37° C. for 30 minutes in TNT (25 mM Tris-HCl pH 7.5, 150 mM NaCl, 0.05% Tween-20) and 5 mM glutathione (reduced form) was sufficient to release the proteins bound to the beads by interaction with glutathione. The supernatant was transferred to a fresh tube and immunoprecipitated with affinity-purified antisera directed against the C-terminus of p34 cdc2. The immunoprecipitates (with Protein A-Sepharose) were washed three times in TNT and used in a histone H1 kinase assay as described.

To show phosphorylation of the GT-cyclin E protein by the bound CDC2 kinase, GT-cyclin E beads were prepared and incubated with G1 extracts and used in a kinase assay as described previously for histone H1; however histone H1 was not included in the assay. After incubation the pellet is washed with H1 kinase buffer +0.1 mg/ml BSA, then with 30 mM HEPES-KOH pH 7.5, 7 mM MgCl$_2$, 1 mM DTT, 0.1 mg/ml BSA, 0.2M NaCl, and finally with TNT. The beads were then incubated with 1 ml of TNT and 5 mM glutathione (pH 7.5) at 37° C. for 30 minutes to release the GT-cyclin E fusion protein. The supernatant was then collected and immunoprecipitated with antisera directed against cyclin E. Immune complexes were subsequently collected by adherence to Protein A-Sepharose. Immunoprecipitates were washed 3 times with TNT and products analyzed on 12% SDS-PAGE gels followed by autoradiography.

For immunoprecipitation of cyclin E from HeLa cell extracts, 2×10$^6$ cells were lysed in 50 mM Tris-HCl pH 7.4, 250 mM NaCl, and 0.1% NP-40 and clarified by ultracentrifugation at 100,000×g for 30 minutes. Samples were immunoprecipitated using Protein A-sepharose with 15 µl of normal rabbit sera or sera generated against the cyclin E fusion protein. Immunoprecipitates were washed with kinase buffer and 0.1 mg/ml BSA, and the kinase assay was performed as described above.

T-peptide kinase assays were performed as described previously (D'Urso et al., 1990).

Yeast strains

Yeast strains used were isogenic with strain YH110 (Richardson et al., 1989). Unmarked deletions of CLN1, CLN2, and CLN3 were constructed in this strain background. These deletions removed significant portions of the cyclin homology in CLN1 and CLN2 (Hadwiger et al., 1989; Cross & Tinklenberg, 1991) and completely deleted the CLN3 coding sequence (Cross, 1990). All the deletion alleles were null alleles by the assays described previously (Richardson et al., 1989). These deletion alleles were unmarked, unlike the originally described cln disruptions (Richardson et al., 1989), and therefore were compatible with the plasmid transformation experiments performed here. The cln-deficient strain was kept alive by the GAL-CLN3 plasmid described previously (Cross, 1990). The cdc28-13 allele in this isogenic strain background was provided by D. Lew and was combined with the three cln deletions by mating and tetrad analysis.

Yeast transfections

Transfections were performed using the lithium acetate procedure according to the method of Schiestl and Gietz (1989). Yeast cells grown in galactose were transfected with 2 µg of library DNA in each of 50 independent aliquots. Transformants were selected on galactose for leucine prototrophy and typically numbered 1000–2000 per plate. Colonies were grown for 2 days and then replica plated onto YEP-glucose. Colonies that grew on glucose were patched onto FOA medium (Boeke et al., 1984) to identify colonies that could grow without the GAL-CLN3 plasmid. Plasmid DNA was rescued into E. coli by electroporation from colonies surviving this screen and minipreps were retransfected into 589-5 strain yeast cells to confirm plasmid-dependent complementation of the triple cln deletion. For the screen identifying human CDC2 homologs, colonies growing on glucose were tested for cosegregation of glucose growth and retention of the transfected plasmids.

Construction of cyclin E retroviral vector

The cyclin E retroviral vector (LXSN-cyclin E) was constructed by inserting a blunt-ended HindIII fragment of the human cyclin E cDNA HU4 (Koff et al., 1991) (which contains the entire open reading frame) into the HpaI site of LXSN, a murine retrovirus-based vector (Mill and Rosman, 1989), in the sense orientation.

Cells

MANCA cells were maintained at 2–5×10$^5$ cells/ml in RPMI plus 10% calf serum in an atmosphere containing 5% CO$_2$. Cells were fractionated from exponentially growing populations by centrifugal elutriation (Marraccino et al., 1992). For synchronization at the G1/S boundary approximately 1×10$^8$ G1 cells were collected from exponentially growing populations of MANCA cells by elutriation and inoculated into RPMI containing 10% calf serum and 5 µg/ml aphidicolin and allowed to grow for 8 hours. Flow cytometric measurement of cellular DNA content was used to demonstrate the synchrony of the cell population. MANCA cells synchronized in G1 were prepared exactly as described previously (Marraccino et al., 1992).

Rat PC-12 cells were maintained in DMEM containing 5% fetal calf serum and 10% horse serum in an atmosphere containing 10% $CO_2$. To induce neuronal differentiation confluent cells were split 1:20 and on the second day the media was replaced with serum free medium. Cells were incubated in serum free media for 24 h and the medium was then changed to complete medium containing 50 ng/ml NGF. NGF is added every two days and cells were harvested after 4–5 days.

Rat 208F cells were maintained in DMEM plus 10% calf serum in an atmosphere containing 5% $CO_2$. To generate quiescent cells, the cells were washed twice with PBS and subsequently grown in DMEM with 0.1% calf serum for 48 hours.

To measure G1 length in Rat-1 cells, the cells were synchronized in pseudometaphase by the addition of nocodazole at 100 ng/ml for 4 hours. The mitotic cells were collected by gentle pipetting. Cells were then rinsed with DMEM and plated at $2 \times 10^4/35$ mm dish with DMEM plus 10% bovine calf serum. Cells were pulsed labelled with tritiated thymidine (80 Ci/mmole; 2 µCi/ml) for 30 minutes at each time point. Incorporation of thymidine into DNA was measured as described (Roberts & D'Urso, 1988).

Rat-1 cells that constitutively expressed cyclin E were produced as described (Miller and Rosman, 1989). PA317 amphotropic retrovirus packaging cells were plated at $5 \times 10^5$ cells per 60 mm dish on day 1. On day 2, 1 µg of LXSN-cyclin E, or the control DNA LXSN, was transfected into cells using a modification of the calcium phosphate procedure (Ohtsubo et al., 1991). On day 3, the culture medium was replaced with fresh medium and PE501 ecotropic packaging cells were plated 105 cells per 60 mm dish. On day 4, PE501 cells were fed with 4 ml of fresh medium containing polybrene. Virus was harvested from the PA317 cells and 5 µl to 1 ml of this material were used to infest PE501 cells. On day 5 the PE501 cells were trypsinized and plated in 10 cm dishes in medium containing 0.8 mg/ml G-418. Dishes with small numbers of colonies were used for isolation of individual clones by using cloning rings. These clonal lines were then analyzed by Southern blot analysis and assayed for vector titer and suitable clonal lines containing unrearranged retroviral genomes propagated as virus-producing cell lines. The LXSN and LXSN-cyclin E viruses were used to infect Rat-1 cells and G-418 resistant cell populations used for further studies.

Preparation of GST and GST-E columns

*E. coli* containing the plasmids pGEX-2T or pGEX-2TcycE (GEN-cyclin E) were grown to $OD_{600} = 0.4$ and induced with 0.4 mM IPTG for 4 h at 30° C. Cells were harvested and washed once in PBS and stored at −70° C. GST encoded by pGEX-2T was prepared as described previously (Koff et al., 1991). Fusion protein GT-cyclin E (GT-cycE) encoded by pGEX-2TcycE was prepared using a modification of the method of Glotzer et al. (1991). The cell pellet from a 500 ml culture was sonicated in 7 ml of 10 mM Tris-HCl pH 7.4, 0.1M NaCl, 1 mM $MgCl_2$, 5 mM DTT with protease inhibitors. The extract was clarified by centrifugation at 13,000×g and the supernatant discarded. The pellet was resuspended in 7 ml TND buffer (0.2M Tris-HCl pH 8.2, 0.5M NaCl, 5 mM DTT) and pelleted again. After discarding the supernatant the pellet was resuspended in 8M urea containing 5 mM DTT and mixed gently at 4° C. for 4 hours. The resulting extract was clarified at 13,000×g for 10 minutes and the supernatant dialyzed against TN buffer (i.e., TND buffer containing 1 mM DTT instead of 5 mM DTT).

At least 2.5 mg of either GT or GT-cycE were incubated with 1 ml of glutathione agarose beads for 2 hours at 4° C., and subsequently collected at 1000×g and washed 3 times with TN buffer containing 1 mM DTT. Coupling of the GT or GT fusion protein to the glutathione agarose support was carried out using the following protocol. The support was transferred to a column and washed with 0.1M borate buffer pH 8.0 followed by 0.2M triethanolamine pH 8.2. Dimethylpimelimidate (DMP) cross linker (40 mM DMP, 0.2M triethanolamine pH 8.2) was run into the column leaving just a meniscus. Coupling was continued for 1 hour at room temperature. After coupling, the column was moved to 4° C. and washed with 40 mM ethanolamine pH 8.2, followed by 0.1M borate buffer pH 8.0. To elute uncoupled protein, the column was washed with PBS containing 20 mM glutathione pH 7.5 and subsequently stored in PBS containing 0.5% azide.

H1 kinase assays $8.3 \times 10^6$ cells were lysed by sonication in 100 µl of H1 lysis buffer (50 mM Tris-HCl pH 7.4, 0.25M NaCl, 0.5% NP40) containing protease inhibitors (1 mM PMSF, 20 1µg/ml TPCK, 20 µg/ml SBTI, 10 µg/ml leupeptin). Sonicated lysates were clarified at 13,000×g for 10 minutes at 4° C. and the supernatant transferred to a fresh tube and diluted two-fold with fresh H1 lysis buffer.

50 µl of extract was immunoprecipitated with a 2 µl of polyclonal antisera against cyclin E, or the C-terminus of p34 CDC2 for 1 hour. For cyclin A immunoprecipitations, lysates were incubated with 5 µl of the C160 monoclonal antibody for 30 minutes and for an additional 30 minutes after addition of 2 µl of rabbit anti-mouse antibody. Immune complexes were collected on Protein A sepharose, washed 2×with lysis buffer and 4×with H1 kinase buffer (20 mM Tris-HCl pH 7.4, 7.5 mM $MgCl_2$, 1 mM DTT). H1 kinase reactions were performed as described previously (Koff et al., 1991).

Preparation of lysates for immunoprecipitation-Western blot analysis

Cells ($8.3 \times 10^6/100$ µl) were lysed by sonication in SDS-RIPA (1% deoxycholate, 1% Triton X-100, 0.1% SDS, 50 mM Tris-HCl pH 8.0, 0.3M NaCl, 0.1 mM orthovanadate, 50 mM NaF) containing protease inhibitors. In these experiments, approximately 1 mg of affinity purified antibody, or 1 ml of cyclin E pre-immune sera was coupled to 1 ml of CNBr-activated sepharose according to the manufacturers recommendations. In the experiments using cells arrested at the G1/S boundary, immunoprecipitations were carried out with affinity purified antibodies coupled to CNBr-activated sepharose using $2.5 \times 10^7$ cells and 100 µl of antibody linked sepharose. For studies of cell cycle fractions obtained by centrifugal elutriation we used $1 \times 10^7$ cells with 30 µl of anti-cyclin E sepharose.

Immune complexes were allowed to form for 3 hours at 4° C. and were then washed twice with SDS-RIPA containing 5 mg/ml BSA and 3 times with SDS-RIPA. Samples were suspended in Laemmli sample buffer and separated on 12% PAGE gels. Gels were transferred to nitrocellulose by semi-dry electroblotting and the membranes blocked with either 2% milk in TNT (25 mM Tris-HCl pH 7.5, 150 mM NaCl, 0.05% Tween-20) for CDC2 or CDK2, or 1% gelatin in TNT for cyclin E. Blots were probed overnight at room temperature with either a 1:300 dilution of affinity purified anti-CDC2, or 1:1000 dilution of anti CDK2 serum, or a

Citations

Amon, A., Surana, U., Muroff, I., and Nasmyth (1992) Regulation of p34 CDC28 tyrosine phosphorylation is not required for entry into mitosis in *S. cerevisae*. Nature 355:368–371.

Arion, D., Meijer, L., Brizuela, L., and Beach, D. (1988). cdc2 is a component of the M phase-specific histone H1 kinase: evidence for identity with MPF. Cell 55, 371–378.

Bandara, L., Adamczewski, J., Hunter, T., and LaThanghe, N. (1991). Cyclin A and the retinoblastoma gene product complex with a common transcription factor. Nature 352:249–251.

Baserga, R. (1985). The biology of cell reproduction. Cambridge, Mass. Harvard University Press.

Beach, D., Durkacz, B., and Nurse, P. (1982). Functionally homologous cell cycle control genes in fission yeast and budding yeast. Nature 300, 706–709.

Blow, J. J., and Nurse, P. (1990). A cdc2-like protein is involved in the initiation of DNA replication in Xenopus egg extracts. Cell 62, 855–862.

Boeke, J. D., LaCroute, F., and Fink, G. R. (1984). A positive selection for mutants lacking 5'-phosphate decarboxylase activity in yeast: 5-fluoro-orotic acid resistance. Mol. Gen. Genet. 197, 345–346.

Booher, R., and Beach, D. (1987). Interaction between cdc13$^+$ and cdc2 in the control of mitosis in fission yeast; dissociation of the $G_1$ and $G_2$ roles of the cdc2$^+$ protein kinase. EMBO J. 6, 3441–3447.

Booher, R. N., Alfa, C. E., Hyams, J. S., and Beach, D. H. (1989). The fission yeast cdc2/cdc13/suc1 protein kinase: regulation of catalytic activity and nuclear localization. Cell 58, 485–497.

Brooks, R. (1977). Continuous protein synthesis is required to maintain the probability of entry into S phase. Cell 12:311–317.

Broek, D., Bartlett, R., Crawford, K., and Nurse, P. (1990). Involvement of p34$^{cdc2}$ in establishing the dependency of S phase on mitosis. Nature 349, 388–393.

Cantley, L., Auger, K., Carpenter, C., Duckworth, B., Graziani, A., Kapeller, R., and Soltoff, S. (1991). Oncogenes and signal transduction. Cell 64:281–302.

Chang, F., and Herskowitz, I. (1990). Identification of a gene necessary for cell cycle arrest by a negative growth factor of yeast: FAR1 is an inhibitor of a G1 cyclin, CLN2. Cell 63:999–1011.

Chao, M. (1992). Growth factor signalling: where is the specificity? Cell 68:995–997.

Colicelli, J., Birchmeier, C., Michaeli, T., O'Neill, K., Riggs, M., and Wigler, M. (1989). Isolation and characterization of a mammalian gene encoding in high-affinity cAMP phosphodiesterase. Proc. Natl. Acad. Sci. USA 86, 3599–3603.

Cross, F. (1988). DAF1, a mutant gene affecting size control, pheromone arrest, and cell cycle kinetics of *Saccharomyces cerevisiae* Mol. Cell. Biol. 8, 4675–4684.

Cross, F. (1990). Cell cycle arrest caused by CLN gene deficiency in *Saccharomyces cerevisiae* resembles START-1 arrest and is independent of the mating-pheromone signalling pathway. Molec. Cell. Biol. 10, 6482–6490.

Cross, F. R., and Tinkelenberg, A. H. (1991). A potential positive feedback loop controlling CLN1and CLN2 gene expression at the start of the yeast cell cycle. Cell 65, 875–883.

Cross, F., Roberts, J., and Weintraub, J. (1989). Simple and complex cell cycles. Ann. Rev. Cell Biol. 5:341–395.

Dirick, L., and Nasmyth, K. (1991). Positive feedback in the activation of G1 cyclins in yeast. Nature 351:754–757.

Desai, D., Gu, Y., and Morgan, D. (1992). Activation of human cyclin-dependent kinases in vitro. Molec. Biol. of the Cell, in press.

DeVoto, S., Mudryj, M., Pines, J., Hunter, T., and Nevins, J. (1992). A cyclin A-protein kinase complex possesses sequence-specific DNA binding activity: p33 CDK2 is a component of the E2F-cyclin A complex. Cell 68:167–176.

Draetta, G., and Beach, D. (1988). Activation of cdc2 protein kinase during mitosis in human cells: cell cycle-dependent phosphorylation and subunit rearrangement. Cell 54, 17–26.

Draetta, G., Luca, F., Westendorf, J., Brizuela, L., Ruderman, J., and Beach, D. (1989). cdc2 protein kinase is complexed with both cyclin A and B: evidence for proteolytic inactivation of MPF. Cell 56, 829–838.

Dunphy, W. G., Brizuela, L., Beach, D., and Newport, J. (1988). The Xenopus cdc2 protein is a component of MPF, a cytoplasmic regulator of mitosis. Cell 54, 423–431.

D'Urso, G., Marraccino, R. L., Marshak, D. R., and Roberts, J. M. (1990). Cell cycle control of DNA replication by a homologue from human cells of the $p_{34}^{cdc2}$ protein kinase. Science 250, 786–791.

Enoch, T., and Nurse, P. (1990). Mutation of fission yeast cell cycle control genes abolishes dependence of mitosis on DNA replication. Cell 60:665–673.

Elledge, S. J., and Spottswood, M. R. (1991). A new human p34 protein kinase, CDK2, identified by complementation of a CDC28 mutation in *S. cerevisiae*, is a homolog of Xenopus Eg 1. EMBO J 10:2653–2659.

Elledge, S., Richman, R., Hall, F., Williams, F., Lodgson, N., and Harper, W. (1992). CDK2 encodes a 33-kDaa cyclin A-associated protein kinase and is expressed before CDC2 in the cell cycle. Proc. Nat. Acad. Sci. USA, in press.

Evans, T., Rosenthal, E. T., Youngblom, J., Disten, D., and Hunt, T. (1983). Cyclin: a protein specified by maternal mRNA in sea urchin egg that is destroyed at each cleavage division. Cell 33:389–396.

Fang, F., and Newport, J. (1991). Evidence that the G1-S and G2-M transitions are controlled by different CDC2 proteins in higher eukaryotes. Cell 66:731–742.

Furakawa, Y., Piwnica-Worms, H., Ernst, T. J., Kanakura, Y., and Griffin, J. D. (1990). cdc2 gene expression at the $G_1$ to S transition in human T lymphocytes. Science 250, 805–808.

Gautier, J., Norbury, C., Lohka, M., Nurse, P., and Maller J. L. (1988). Purified maturation-promoting factor contains the product of a Xenopus homolog of the fission yeast cell cycle control gene cdc2$^+$. Cell 54, 433–439.

Gautier, J., Minshull, J., Lohka, M., Glotzer, M., Hunt, T., and Mailer, J. L. (1990). Cyclin is a component of maturation-promoting factor from Xenopus. Cell 60, 487–494.

Ghiara, J. B., Richardson, H. E., Sugimoto, K., Henze, M., Lew, D. J., Wittenberg, C., and Reed, S. I. (1991). A cyclin B homolog in *S. cerevisiae*: chronic activation of the CDC28 protein kinase by cyclin prevents exit from mitosis. Cell 65, 163–174.

Giordano, A., Lee, J., Scheppler, J., Herrmann, C., Harlow, E., Deuschle, U., Beach, D., and Franza, R. (1991). Cell cycle regulation of histone H1 kinase activity associated with the adenoviral protein E1A. Science 253:1271–1275.

Giordano, A., Whyte, P., Harlow, E., Franza, Jr., B. R., Beach, D., and Draetta, G. (1989). A 60 kDa cdc2-associated polypeptide complexes with the E1A proteins in adenovirus-infected cells. Cell 58, 981–990.

Girard, F., Strausfeld, U., Fernandez, A., and Lamb, N. (1991). Cyclin A is required for the onset of DNA replication in mammalian fibroblasts. Cell 67:1169–1179.

Glotzer, M., Murray, A. W., and Kirschner, M. W. (1991). Cyclin is degraded by the ubiquitin pathway. Nature 349, 132–138.

Gould, K. L., and Nurse, P. (1989). Tyrosine phosphorylation of the fission yeast cdc2$^+$ protein kinase regulates entry into mitosis. Nature 342, 39–45.

Hadwiger, J. A., Wittenberg, C., Richardson, H. E., Lopes, M. dB., and Reed, S. I. (1989). A family of cyclin homologs that control the $G_1$ phase in yeast. Proc. Natl. Acad. Sci. USA 86, 6255–6259.

Hagan, I., Hayles, J., and Nurse, P. (1988). Cloning and sequencing of the cyclin related cdc13 gene and a cytological study of its role in fission yeast mitosis. J. Cell Sci. 91, 587–595.

Hartwell, L. J., Mortimer, R. K., Culotti, J., and Culotti, M. (1973). Genetic control of the cell division cycle in yeast. V. Genetic analysis of cdc mutants. Genetics 74, 267–286.

Hartwell, L. H., Culotti, J., Pringle, J. R., and Reid, B. J. (1974). Genetic control of the cell division cycle in yeast. Science 183, 46–51.

Hartwell, L. (1991). Twenty-five years of cell cycle genetics. Genetics 129:975–980.

Hindley, J., and Phear, G. A. (1984). Sequence of the cell division gene cdc2 from *Schizosaccharomyces pombe*: pattern of splicing and homology to protein kinases. Gene31, 129–134.

Hunt, T. (1989). Maturation promoting factor, cyclin and the control of M-phase. Curr. Opin. Cell Biol. 1, 268–274.

Hunter, T., and Pines, J. (1991). Cyclins and Cancer. Cell 66:1071–1074.

Krek, W., and Nigg, E. A. (1991). Differential phosphorylation of vertebrate p34$^{cdc2}$ kinase at the G1/S and G2/M transitions of the cell cycle: identification of major phosphorylation sites. EMBO J. 10, 305–316.

Labbe, J. C., Lee, M. G., Nurse, P., Picard, A., and Doree, M. (1988). Activation at M-phase of a protein kinase encoded by a starfish homologue of the cell cycle gene cdc2. Nature 335, 251–254.

Labbe, J. C., Capony, J. P., Caput, D., Cavadore, J. C., Derancourt, J., Kaghad, M., Lelias, J. M., Picard, A., and Doree, M. (1989a). MPF from starfish oocytes at first meiotic metaphase is a heterodimer containing one molecule of cdc2 and one molecule of cyclin B. EMBO J. 8, 3053–3058.

Labbe, J. C., Picard, A., Peaucellier, G., Cavadore, J. C., Nurse, P., and Doree, M. (1989b). Purification of MPF from starfish: identification as the H1 histone kinase p34$^{cdc2}$ and a possible mechanism for its periodic activation. Cell 57, 253–263.

Lahue, E., Smith, A., and Orr-Weaver, T. (1991). A novel cyclin gene from Drosophila complements CLN function in yeast. Genes and Dev. 5:2166–2175.

Lamb, N., Fernandez, A., Watrin, A., Labbe, J., and Cavadore, J. (1990). Microinjection of the p34 CDC2 kinase induces marked changes in cell shape, cytoskeletal organization and chromatin structure in mammalian fibroblasts. Cell 60:151–165.

Lehner, C., and O'Farrell, P. (1989). Expression and function of Drosophila cyclin A during embryonic cell progression. Cell 56:957–968.

Lee, M. G., and Nurse, P. (1987). Complementation used to clone a human homologue of the fission yeast cell cycle control gene cdc2. Nature 327, 31–35.

Lee, M. G., Norbury, C. J., Spurr, N. K., and Nurse, P. (1988). Regulated expression and phosphorylation of a possible mammalian cell-cycle control protein. Nature 333, 676–678.

Leopold, P., and O'Farrell, P. (1991). An evolutionarily conserved cyclin homolog from Drosophila rescues yeast deficient in G1 cyclins. Cell 66:1207–1216.

Lew, D. J., Dulic, V., Reed, S. I. (1991). Isolation of three novel human cyclins by rescue of G1 cyclin (Cln) function in yeast. Cell, in press.

Lohka, F., and Masui, Y. (1983). Formation in vitro of sperm pronuclei and mitotic chromosomes induced by amphibian ooplasmic components. Science 220:719–721.

Lorincz, A. T., and Reed, S. I. (1984). Primary structure homology between the product of the yeast cell cycle control gene CDC28 and vertebrate oncogenes. Nature 307, 183–185.

Maller, J. (1991). Mitotic control. Curr. Op. in Cell Biol. 3:269–275.

Marraccino, R., Firpo, E., and Roberts, J. (1992). Activation of the p34 CDC2 protein kinase at the start of S phase in the human cell cycle. Molec. Biol. of the cell, in press.

Marshak, D. R., Vandenberg, M. T., Bae, Y. S., and Yu, I. J. (1991). Characterization of synthetic peptide substrates for p34 cdc2 protein kinase. J. Cell. Biochem. 45, 391–400.

Masui, Y., and Markert, C. (1971). Cytoplasmic control of nuclear behavior during meiotic maturation of frog oocytes. J. Exp. Zool. 177:129–146.

Matsushime, H., Roussel, M. F., Ashumun, R. A., and Sherr, C. J. (1991). Colony-stimulating factor 1 regulates novel cyclins during the G1 phase of the cell cycle. Cell 65, 701–713.

Meijer, I., Arion, D., Golsteyn, R., Pines, J., Brizuela, L., Hunt, T., and Beach, D. (1989). Cyclin is a component of the sea urchin egg M-phase specific histone H1 kinase. EMBO J. 8, 2275–2282.

Mendenhall, M. D., Jones, C. A., and Reed, S. I. (1987). Dual regulation of the yeast CDC28-p40 protein kinase complex: cell cycle, pheromone, and nutrient limitation effects. Cell 50, 927–935.

Miller, A. D., and Rosman, G. (1989). Improved retroviral vectors of gene transfer and expression. BioTechniques 7, 980–990.

Minshull, J., Blow, J. J., and Hunt, T. (1989). Translation of cyclin mRNA is necessary for extracts of activated Xenopus eggs to enter mitosis. Cell 56, 947–956.

Moreneo, S., Hayles, J., and Nurse, P. (1989). Regulation of p34$^{cdc2}$ protein kinase during mitosis. Cell 58, 361–372.

Motokura, T., Bloom, T., Kim, H. G., Juppner, H., Ruderman, J. V., Kronenberg, H. M., and Arnold, A. (1991). A BCL1-linked candidate oncogene which is rearranged in parathyroid tumors encodes a novel cyclin. Nature 350, 512–515.

Mudryj, M., DeVoto, S., Hiebert, S., Hunter, T., Pines, J., and Nevins, J. (1991). Cell cycle regulation of the E2F transcription factor involves an interaction with cyclin A. Cell 65:1243–1253.

Murray, A. W., and Kirschner, M. W. (1989). Cyclin synthesis drives the early embryonic cell cycle. Nature 339, 275–280.

Nash, R., Tokiwa, G., Anand, S., Erickson, K., and Futcher, A. B. (1988). The WHI gene of *Saccharomyces cerivisiae* tethers cell division to cell size and is a cyclin homolog. EMBO J. 7, 4335–4346.

Nurse, P. (1990). Universal control mechanism regulating onset of M-phase. Nature 344, 503–508.

Nurse, P. and Bisset, Y. (1981). Gene required in G1 for commitment to cell cycle and in G2 for control of mitosis in fission yeast. Nature 292, 558–560.

Ohtsubo, M., Yoshida, T., Seino, H., Nishitani, H., Clark, K., Sprague, K., Frasch, M., and Nishimoto, T. (1991). Mutation of the hamster cell cycle gene RCC! is complemented by the homologous genes of Drosophila and S. cerevisiae. EMBO J. 10, 1265–1273.

Osmani, A., McGuire, S., and Osmani, S. (1991). Parallel regulation of the NIMA and p34CDC2 cell cycle-regulated protein kinases is required to initiate mitosis in A. nidulans. Cell 67:283–291.

Pardee, A. B. (1974). A restriction point for control of normal animal cell proliferation. Proc. Natl. Acad. Sci. USA 71, 1286–1290.

Pardee, A. B. (1989). G1 events and regulation of cell proliferation. Science 246, 603–608.

Pardee, A., Medrano, E., and Rossow, P. (1981). A labile protein model for growth control of mammalian cells in The biology of normal human growth, Ritzen et al., eds. Raven Press.

Paris, S., Le Guellec, R., Couturier, A., Le Guellec, K., Omilli, F., Camonis, J., MacNeill, S., and Philippe, M. (1991). Cloning by differential screening of a Xenopus cDNA coding for a protein highly homologous to cdc2. Proc. Natl. Acad. Sci. USA 88, 1029–1043.

Piggot, J. R., Rai, R., and Carter, B. L. A. (1982). A bifunctional gene product involved in two phases of the yeast cell cycle. Nature 298, 391–393.

Pines, J., and Hunter, T. (1987). Molecular cloning and characterization of the mRNA for cyclin from sea urchin eggs. EMBO J. 6:2987–2995.

Pines J., and Hunter, T. (1989). Isolation of a human cyclin cDNA: evidence for cyclin mRNA and protein regulation in the cell cycle and for interaction with $p_{34}^{cdc}2$ Cell 58, 833–846.

Pines, J., and Hunter, T. (1990). Human cyclin A is adenovirus E1A-associated protein p60 and behaves differently from cyclin B. Nature 346, 760–763.

Pondaven, P., Meijer, L., and Beach, D. (1990). Activation of M-phase specific histone H1 kinase by modification of the phosphorylation of its p34 CDC2 and cyclin components. Genes and Dev. 4:9–17.

Rao, P. N., and Johnson, R. T. (1970). Mammalian cell fusion: studies on the regulation of DNA synthesis and mitosis. Nature 225, 159–164.

Reed, S. I., and Wittenberg, C. (1990). Mitotic role for the Cdc28 protein kinase of Saccharomyces cerevisiae. Proc. Natl. Acad. Sci. USA 87, 5697–5701.

Riabowol, K., Draetta, G., Brizuela, L., Vandre, D., and Beach, D. (1989). The cdc2 kinase is a nuclear protein that is essential for mitosis in mammalian cells. Cell 57, 393–401.

Richardson, H. E., Wittenberg, C., Cross, F., and Reed, S. I. (1989). An essential G1 function for cyclin-like proteins in yeast. Cell 59, 1127–1133.

Roberts, J. M., and D'Urso, G. (1988). An origin unwinding activity regulates initiation of DNA replication during mammalian cell cycle. Science 241, 1486–1489.

Rogers, S., Wells, R., and Rechsteiner, M. (1986). Amino acid sequences common to rapidly degraded proteins: the PEST hypothesis. Science 234, 364–368.

Rosenblatt, J., Gu, Y., and Morgan, D. (1992). Human cyclin dependent kinase 2 (CDK2) is activated during the S and G2 phases of the cell cycle and associates with cyclin A. Proc. Nat. Acad. Sci. USA, in press.

Rosenthal, E. T., Hunt, T., and Ruderman, J. V. (1980). Selective translation of mRNA controls the pattern of protein synthesis during early development of the surf clam, Spisula solidissima. Cell 20, 487–494.

Rossow, P., Riddle, B., and Pardee, A. (1979). Synthesis of labile, serum-dependent protein in early G1 controls animal cell growth. Proc. Nat. Acad. Sci. USA, 76:4446–4450.

Schiestl, R. H., and Gietz, R. D. (1989). High efficiency transformation of intact yeast cells using single stranded nucleic acids as a carrier. Current Genetics 16, 339–346.

Schneiderman, M., Dewey, W., and Highfield, D. (1971). Inhibition of DNA synthesis in synchronized Chinese hamster cells treated in G1 with cycloheximide. Exp. Cell Re. 67:147–155.

Shirodkar, S., Ewen, M., DeCaprio, J., Morgan, J., Livingston, D., and Chittenden, T. (1992). The transcription factor E2F interacts with the retinoblastoma product and a p107-cyclin A complex in a cell cycle regulated manner. Cell 68:157–166.

Simanis, V., and Nurse, P. (1986). The cell cycle control gene cdc2$^+$ of fission yeast encodes a protein kinase potentially regulated by phosphorylation. Cell 45, 261–268.

Smith, L., and Ecker, R. (1971). The interactions of steroids with R. pipien oocytes in the induction of maturation. Dev. Bio. 25:233–247.

Soloman, M., Booher, R., Kirschner, M., and Beach, D. (1988). Cyclin in fission yeast. Cell 54, 738–739.

Soloman, M., Glotzer, M., Lee, T. H., Phillippe, M., and Kirschner, M. W. (1990). Cyclin activation of $p34^{cdc2}$. Cell 63, 1013–1024.

Solomon, M., Lee, T., and Kirschner, M. (1992). Role of phosphorylation in p34 CDC2 activation: identification of an activating kinase. Molec. Biol. of the Cell 3:13–27.

Sorger, P., and Murray, A. (1992). S-phase feedback control in budding yeast independent of tyrosine phosphorylation of p34 CDC28. Nature 355:365–368.

Sudbery, P. E., Goodey, A. R., and Carter, B. L. (1980). Genes which control cell proliferation in the yeast Saccharomyces cerevisiae. Nature (London) 288, 401–404.

Surana, U., Robitsch, H., Price, C., Schuster, T., Fitch, I., Futcher, A. B., and Hasmyth, K. (1991). The role of CDC28 and cyclins during mitosis in the budding yeast S. cerevisiae. Cell 65, 145–161.

Swenson, K. I., Farrell, K. M., and Ruderman, J. V. (1986). The clam embryo protein cyclin A induces entry into M phase and the resumption of meiosis in Xenopus oocytes. Cell 47, 861–870.

Th'ng, J. P. H., Wright, P. S., Hamaguchi, J., Lee, M. G., Norbury, C. J., Nurse, P., and Bradbury, E. M. (1990). The FT210 cell line is a mouse G2 phase mutant with a temperature-sensitive CDC2 gene product. Cell 63, 313–324.

Tsai, L., Harlow, E., and Meyerson, M. (1991). Isolation of the human CDK2 gene that encodes the cyclin-A and adenovirus E1A-associated p33 kinase. Nature 353:174–177.

Wang, J., Chenivesse, X., Henglein, B., and Brechot, C. (1990). Hepatitis B virus integration in a cyclin A gene in a hepatocellular carcinoma. Nature 343, 555–557.

Westendorf, J., Sweson, K., and Ruderman, J. (1989). The role of cyclin B in meiosis I. J. Cell Biol. 108:1431–1444.

Wittenberg, C., and Reed, S. I. (1989). Conservation of function and regulation within the Cdc28/cdc2 protein kinase family: Characterization of the human Cdc2HS protein kinase in Saccharomyces cerevisiae. Mol. Cell Biol. 4064–4068.

Wittenberg, C., Sugimoto, K., and Reed, S. I. (1990). G1-specific cyclins of *S. cerevisiae*: cell cycle periodicity, regulation by mating pheromone, and association with the p34$^{CDC28}$ protein kinase. Cell 62, 225–237.

Wynford-Thomas, D., LaMontagne, A., Marin, G., and Prescott, D. (1985). Location of the isoleucine arrest point in CHO and 3T3 cells. Exp. Cell. Res. 158, 525–532.

Xiong, Y., Connolly, T., Futcher, B., and Beach, D. (1991). Human D-type cyclin. Cell 65, 691–699.

Zetterberg, A. (1990). Control of mammalian cell proliferation. Curr. Opin. Cell Biol. 2, 296–300.

Zetterberg, A., and Larson, O. (1985). Kinetic analysis of regulatory events in G1 leading to proliferation of quiescence of Swiss 3T3 cells. Proc. Natl. Acad. Sci. USA 82, 5365–5369.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. An isolated nucleic acid molecule of at least about 10–15 nucleotides in length capable of specifically hybridizing under stringent conditions to the nucleotide sequence residing between positions 58 and 1242 of the human cyclin E cDNA sequence shown in SEQ. ID. NO:1 or to its complementary strand.

2. The isolated nucleic acid molecule of claim 1, encoding a cyclin E polypeptide.

3. The isolated nucleic acid molecule of claim 2, wherein the cyclin E polypeptide is capable of binding and activating a cell division kinase.

4. The isolated nucleic acid molecule of claim 3, wherein the cell division kinase is selected from the group consisting of CDC2, CDC28, CDK2-XL, CDC2-HS, and CDK2-HS.

5. The isolated nucleic acid molecule of claim 2, wherein the cyclin E polypeptide is capable of shortening the G1 phase of the eukaryotic cell cycle.

6. The isolated nucleic acid molecule of claim 1, encoding a polypeptide capable of binding to an antibody that binds to the cyclin E polypeptide shown in FIG. 2.

7. A recombinant expression vector comprising the isolated nucleic acid molecule of claim 1 operably linked to suitable control sequences.

8. Cells transfected or transduced with the recombinant expression vector of claim 7.

9. A method of producing a polypeptide capable of activating a cell division kinase whereby the activated kinase results in a shortening of the G1 phase of the cell cycle, comprising culturing the cells of claim 8 to produce the polypeptide encoded by said isolated nucleic acid molecule.

10. A method of shortening the cell cycle in a mammalian cell in vitro, comprising transfecting or transducing the cell with the recombinant expression vector of claim 7.

11. The isolated nucleic acid molecule of claim 1, encoding a polypeptide having an activity that is greater or less than the activity of the cyclin E encoded by the cDNA sequence shown in FIG. 2, wherein the activity is selected from the group consisting of binding affinity of the polypeptide or cyclin E to a CDK2 kinase polypeptide, enzyme activity of the CDK2 kinase when the polypeptide or the cyclin E and the CDK2 are resident together in a polypeptide or cyclin E:CDK2 complex, and altered stability of the polypeptide:CDK2 complex as compared to the cyclin E:CDK2 complex.

12. The method of claim 9, wherein the cultured cells exhibit reduced growth factor dependence for transitioning the G1 phase of the cell cycle.

* * * * *